(12) United States Patent
Zhang et al.

(10) Patent No.: US 12,221,488 B2
(45) Date of Patent: Feb. 11, 2025

(54) APJ ANTIBODY, FUSION PROTEIN THEREOF WITH ELABELA, AND PHARMACEUTICAL COMPOSITIONS AND USE THEREOFUS01

(71) Applicant: GMAX BIOPHARM LLC, Hangzhou (CN)

(72) Inventors: Cheng Zhang, Hangzhou (CN); Lei Sun, Hangzhou (CN); Rongzhu Wang, Hangzhou (CN); Chenjiang Yao, Hangzhou (CN); Xiaofeng Wang, Hangzhou (CN); Hua Zhang, Hangzhou (CN); Shuqian Jing, Hangzhou (CN)

( * ) Notice: Subject to any disclaimer, the term of this patent is extended or adjusted under 35 U.S.C. 154(b) by 1031 days.

(21) Appl. No.: 17/251,663

(22) PCT Filed: Jun. 13, 2019

(86) PCT No.: PCT/CN2019/091090
§ 371 (c)(1),
(2) Date: Dec. 11, 2020

(87) PCT Pub. No.: WO2019/238093
PCT Pub. Date: Dec. 19, 2019

(65) Prior Publication Data
US 2021/0163614 A1 Jun. 3, 2021

(30) Foreign Application Priority Data

Jun. 13, 2018 (CN) .......................... 201810606914.0

(51) Int. Cl.
*C07K 16/28* (2006.01)
*C07K 14/47* (2006.01)
*C07K 14/72* (2006.01)

(52) U.S. Cl.
CPC ...... *C07K 16/2869* (2013.01); *C07K 14/4705* (2013.01); *C07K 14/723* (2013.01); *C07K 2317/24* (2013.01); *C07K 2317/92* (2013.01); *C07K 2319/00* (2013.01)

(58) Field of Classification Search
CPC .......................... C07K 16/28; C07K 16/2863; C07K 2317/56; C07K 2317/565; C07K 2317/24; C07K 2317/92; C07K 16/2869; C07K 14/723; A61K 2039/505; A61K 39/3955
See application file for complete search history.

(56) References Cited

U.S. PATENT DOCUMENTS

| | | | |
|---|---|---|---|
| 2005/0075275 A1 | 4/2005 | Albrecht et al. | |
| 2014/0170134 A1 | 6/2014 | Schneewind et al. | |
| 2014/0328850 A1 | 11/2014 | Lu et al. | |
| 2017/0146518 A1 | 5/2017 | Gavard et al. | |
| 2017/0224779 A1 | 8/2017 | Gong et al. | |

FOREIGN PATENT DOCUMENTS

| | | |
|---|---|---|
| CN | 1283228 A | 2/2001 |
| CN | 104371019 A | 2/2015 |
| CN | 105026423 A | 11/2015 |
| CN | 105916881 A | 8/2016 |
| CN | 106659774 A | 5/2017 |
| CN | 107646039 A | 1/2018 |
| DE | 10138569 A1 | 4/2003 |
| JP | 2017500018 A | 1/2017 |
| WO | WO 1999/033976 A1 | 7/1999 |
| WO | 2005/106493 A1 | 11/2005 |
| WO | WO 2006/023893 A2 | 3/2006 |
| WO | WO 2012/102363 A1 | 8/2012 |
| WO | 2015/077491 A1 | 5/2015 |
| WO | WO 2015/140296 A2 | 9/2015 |
| WO | WO 2016/061141 A1 | 4/2016 |
| WO | WO-2019/040390 A1 * | 2/2019 |

OTHER PUBLICATIONS

Zhiyu Ouyang, Guoping Tian, "Research Progress of Apelin/APJ System in Heart Failure", Journal of Community Medicine. vol. 13, Issue 23: 78-80, Dec. 10, 2015.
"Drug Re-evaluation for APJ Receptor and Cobisistat Alleviates Apelin-mediated Platelet Aggregation", China Master's Theses Full-text Database, Medicine/Hygiene, Issue 4, the whole document, Apr. 15, 2018.
Genbank, AAO73022.1: anti-meningococcal polysaccharide group C monoclonal antibody 1922.2 immunoglobulin light chain, partial [Mus musculus], title, Protein, CDS, Origin, Jul. 25, 2016.
Genbank, AGN91363.1: immunoglobulin heavy chain variable region, partial [Mus musculus] title, Protein, CDS, Origin, Aug. 31, 2014.
Bridget A. Puffer et al., Expression and coreceptor function of APJ for primate immunodeficiency viruses, Virology, vol. 276, Issue 02: 435-444, Oct. 25, 2000.
Zhi Wang et al., Elabela-Apelin Receptor Signaling Pathway is Functional in Mammalian Systems, Scientific Reports, Issue 05, No. 8170, Feb. 2, 2015.
Product Datasheet "Function AntiAPJ Receptor antibody ab97464 Product name AntiAPJ Receptor antibody", Nov. 1, 2013, XP055171775.
"Function AntiAPJ Receptor antibody ab97452 AntiAPJ Receptor antibody images Product Datasheet", Nov. 1, 2013, XP055171768.
Perez De La Lastra et al, "Epitope mapping of 10 monoclonal antibodies against the pig analogue of human membrane cofactor protein (MCP)", Immunology, vol. 96 No. 4, Apr. 1, 1999, pp. 663-670, XP055572134, GB, ISSN: 0019-2805, DOI: 10.1046/j.1365-2567.1999.00732.x.

(Continued)

*Primary Examiner* — Bridget E Bunner
(74) *Attorney, Agent, or Firm* — Jun He Law Offices P.C; James J. Zhu

(57) ABSTRACT

Provided herein are an apelin receptor (APJ) antibody and its fusion protein with Elabela. Also provided herein is a pharmaceutical composition of a fusion protein with APJ antibody and Elabela, and use thereof in treating, preventing, or alleviating one or more symptoms of pulmonary arterial hypertension, pulmonary hypertension or one or more symptoms of heart failure.

12 Claims, 5 Drawing Sheets
Specification includes a Sequence Listing.

(56) References Cited

OTHER PUBLICATIONS

Christian Klein et al "Epitope interactions of monoclonal antibodies targeting CD20 and their relationship to functional properties" MABS, vol. 5 No. 1, Jan. 1, 2013, pp. 22-33, XP055117097, ISSN: 1942-0862, DOI: 10.4161/mabs.22771.
The office action for the corresponding European application 19819592.7 issued on Aug. 7, 2023.
Chng, Serene C., et al. "Elabela: a hormone essential for heart development signals via the apelin receptor." Developmental cell 27.6 (2013): 672-680.

* cited by examiner

```
SEQUENCE LISTING

<160> NUMBER OF SEQ ID NOS: 173

<210> SEQ ID NO 1
<211> LENGTH: 11
<212> TYPE: PRT
<213> ORGANISM: Mus musculus

<400> SEQUENCE: 1

His Ala Ser Gln Asn Ile His Val Trp Leu Ser
1               5                   10

<210> SEQ ID NO 2
<211> LENGTH: 7
<212> TYPE: PRT
<213> ORGANISM: Mus musculus

<400> SEQUENCE: 2

Lys Ala Ser Asn Leu His Thr
1               5

<210> SEQ ID NO 3
<211> LENGTH: 9
<212> TYPE: PRT
<213> ORGANISM: Mus musculus

<400> SEQUENCE: 3

Gln Gln Gly His Ser Tyr Pro Leu Thr
1               5

<210> SEQ ID NO 4
<211> LENGTH: 16
<212> TYPE: PRT
<213> ORGANISM: Mus musculus

<400> SEQUENCE: 4

Arg Ser Ser Gln Ser Leu Ile Tyr Thr Asn Gly Asn Thr Tyr Leu His
1               5                   10                  15

<210> SEQ ID NO 5
<211> LENGTH: 7
<212> TYPE: PRT
<213> ORGANISM: Mus musculus
```

```
<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Ser Gln Asn Thr His Val Pro Leu Thr
1               5

<210> SEQ ID NO 7
<211> LENGTH: 16
<212> TYPE: PRT
<213> ORGANISM: Mus musculus

<400> SEQUENCE: 7

Arg Ser Ser Gln Asn Leu Val His Ser Gly Asn Thr His Leu Asp
1               5                   10                  15

<210> SEQ ID NO 8
<211> LENGTH: 7
<212> TYPE: PRT
<213> ORGANISM: Mus musculus

<400> SEQUENCE: 8

Lys Val Ser Asp Arg Leu Ser
1               5

<210> SEQ ID NO 9
<211> LENGTH: 9
<212> TYPE: PRT
<213> ORGANISM: Mus musculus

<400> SEQUENCE: 9

Phe Gln Ala Ser His Val Pro Leu Thr
1               5

<210> SEQ ID NO 10
<211> LENGTH: 16
<212> TYPE: PRT
<213> ORGANISM: Mus musculus

<400> SEQUENCE: 10

Arg Ser Asp Gln Ser Leu Val His Arg Thr Gly Asn Thr His Leu Asp
1               5                   10                  15

<210> SEQ ID NO 11
<211> LENGTH: 9
<212> TYPE: PRT
<213> ORGANISM: Mus musculus

<400> SEQUENCE: 11

Phe Gln Ala Ser His Ile Pro Phe Thr
1               5

<210> SEQ ID NO 12
<211> LENGTH: 10
<212> TYPE: PRT
<213> ORGANISM: Mus musculus

<400> SEQUENCE: 12
```

```
Gly Phe Pro Phe Asn Ile Asn Ala Met Asn
1               5                  10

<210> SEQ ID NO 13
<211> LENGTH: 19
<212> TYPE: PRT
<213> ORGANISM: Mus musculus

<400> SEQUENCE: 13

Arg Ile Arg Ser Lys Ser Asn Asn Tyr Ala Thr Tyr Tyr Ala Asp Ser
1               5                  10                  15

Val Lys Asp

<210> SEQ ID NO 14
<211> LENGTH: 9
<212> TYPE: PRT
<213> ORGANISM: Mus musculus

<400> SEQUENCE: 14

Gly Pro Tyr Leu Tyr Ala Met Asp Tyr
1               5

<210> SEQ ID NO 15
<211> LENGTH: 10
<212> TYPE: PRT
<213> ORGANISM: Mus musculus

<400> SEQUENCE: 15

Gly Phe Ser Leu Thr Asn Tyr Gly Val Thr
1               5                  10

<210> SEQ ID NO 16
<211> LENGTH: 16
<212> TYPE: PRT
<213> ORGANISM: Mus musculus

<400> SEQUENCE: 16

Val Val Trp Gly Asp Gly Thr Thr Ser Ser His Ser Thr Leu Met Ser
1               5                  10                  15

<210> SEQ ID NO 17
<211> LENGTH: 8
<212> TYPE: PRT
<213> ORGANISM: Mus musculus

<400> SEQUENCE: 17

Ser Asn Trp Gly Ser Phe Thr Tyr
1               5

<210> SEQ ID NO 18
<211> LENGTH: 10
<212> TYPE: PRT
<213> ORGANISM: Mus musculus

<400> SEQUENCE: 18

Gly Phe Thr Phe Ser Ser Tyr Ala Met Ser
1               5                  10

<210> SEQ ID NO 19
<211> LENGTH: 16
<212> TYPE: PRT
<213> ORGANISM: Mus musculus

<400> SEQUENCE: 19
```

```
Ser Ile Ser Ser Gly Gly Ser Ile Tyr Tyr Pro Glu Ser Val Lys Gly
1               5                   10                  15

<210> SEQ ID NO 20
<211> LENGTH: 11
<212> TYPE: PRT
<213> ORGANISM: Mus musculus

<400> SEQUENCE: 20

Gly Arg Gly Gly Ser Gln Ala Trp Phe Ala Tyr
1               5                   10

<210> SEQ ID NO 21
<211> LENGTH: 16
<212> TYPE: PRT
<213> ORGANISM: Mus musculus

<400> SEQUENCE: 21

Ser Ile Ser Ser Gly Gly Ser Ile Tyr Leu Pro Asp Ser Leu Lys Gly
1               5                   10                  15

<210> SEQ ID NO 22
<211> LENGTH: 11
<212> TYPE: PRT
<213> ORGANISM: Mus musculus

<400> SEQUENCE: 22

Gly Arg Gly Asn Ser Ser Ala Trp Phe Ala Tyr
1               5                   10

<210> SEQ ID NO 23
<211> LENGTH: 380
<212> TYPE: PRT
<213> ORGANISM: Homo sapiens

<400> SEQUENCE: 23

Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
                20                  25                  30

Ala Ile Tyr Met Leu Val Phe Leu Leu Gly Thr Thr Gly Asn Gly Leu
            35                  40                  45

Val Leu Trp Thr Val Phe Arg Ser Ser Arg Glu Lys Arg Arg Ser Ala
    50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
                100                 105                 110

Met Tyr Ala Ser Val Phe Cys Leu Thr Gly Leu Ser Phe Asp Arg Tyr
            115                 120                 125

Leu Ala Ile Val Arg Pro Val Ala Asn Ala Arg Leu Arg Leu Arg Val
    130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
```

```
            180                 185                 190
Ser Trp Ala Trp Glu Val Gly Leu Gly Val Ser Ser Thr Thr Val
    195                 200                 205
Gly Phe Val Pro Phe Thr Ile Met Leu Thr Cys Tyr Phe Ile
    210                 215                 220
Ala Gln Thr Ile Ala Gly His Phe Arg Lys Glu Arg Ile Glu Gly Leu
225                 230                 235                 240
Arg Lys Arg Arg Leu Leu Ser Ile Ile Val Val Leu Val Val Thr
                    245                 250                 255
Phe Ala Leu Cys Trp Met Pro Tyr His Leu Val Lys Thr Leu Tyr Met
                260                 265                 270
Leu Gly Ser Leu Leu His Trp Pro Cys Asp Phe Asp Leu Phe Leu Met
            275                 280                 285
Asn Ile Phe Pro Tyr Cys Thr Cys Ile Ser Tyr Val Asn Ser Cys Leu
            290                 295                 300
Asn Pro Phe Leu Tyr Ala Phe Phe Asp Pro Arg Phe Arg Gln Ala Cys
305                 310                 315                 320
Thr Ser Met Leu Cys Cys Gly Gln Ser Arg Cys Ala Gly Thr Ser His
                    325                 330                 335
Ser Ser Ser Gly Glu Lys Ser Ala Ser Tyr Ser Ser Gly His Ser Gln
                340                 345                 350
Gly Pro Gly Pro Asn Met Gly Lys Gly Gly Glu Gln Met His Glu Lys
            355                 360                 365
Ser Ile Pro Tyr Ser Gln Glu Thr Leu Val Val Asp
            370                 375                 380

<210> SEQ ID NO 24
<211> LENGTH: 380
<212> TYPE: PRT
<213> ORGANISM: Rhesus macaque

<400> SEQUENCE: 24

Met Glu Glu Gly Gly Asp Phe Asp Asn Tyr Tyr Gly Ala Asp Asn Gln
1               5                   10                  15
Ser Glu Cys Glu Tyr Thr Asp Trp Lys Ser Ser Gly Ala Leu Ile Pro
                20                  25                  30
Ala Ile Tyr Met Leu Val Phe Leu Leu Gly Thr Thr Gly Asn Gly Leu
                35                  40                  45
Val Leu Trp Thr Val Phe Arg Ser Ser Arg Glu Lys Arg Arg Ser Ala
        50                  55                  60
Asp Ile Phe Ile Ala Ser Leu Ala Val Ala Asp Leu Thr Phe Val Val
65                  70                  75                  80
Thr Leu Pro Leu Trp Ala Thr Tyr Thr Tyr Arg Asp Tyr Asp Trp Pro
                85                  90                  95
Phe Gly Thr Phe Ser Cys Lys Leu Ser Ser Tyr Leu Ile Phe Val Asn
                100                 105                 110
Met Tyr Ala Ser Val Phe Cys Leu Thr Gly Leu Ser Phe Asp Arg Tyr
            115                 120                 125
Leu Ala Ile Val Arg Pro Val Ala Asn Ala Arg Leu Arg Leu Arg Val
        130                 135                 140
Ser Gly Ala Val Ala Thr Ala Val Leu Trp Val Leu Ala Ala Leu Leu
145                 150                 155                 160
Ala Met Pro Val Met Val Phe Arg Thr Thr Gly Asp Leu Glu Asn Thr
                165                 170                 175
```

```
Thr Lys Val Gln Cys Tyr Met Asp Tyr Ser Met Val Ala Thr Val Ser
            180                 185                 190

Ser Asp Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
                260                 265                 270

Leu Gly Ser Leu Leu His Trp Pro Cys Asp Phe Asp Leu Phe Leu Met
            275                 280                 285

Asn Val Phe Pro Tyr Cys Thr Cys Ile Ser Tyr Val Asn Ser Cys Leu
        290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
                340                 345                 350

Gly Pro Gly Pro Asn Met Gly Lys Gly Gly Glu Gln Met His Glu Lys
            355                 360                 365

Ser Ile Pro Tyr Ser Gln Glu Thr Leu Val Val Asp
            370                 375                 380

<210> SEQ ID NO 25
<211> LENGTH: 377
<212> TYPE: PRT
<213> ORGANISM: Rattus norvegicus

<400> SEQUENCE: 25

Met Glu Asp Asp Gly Tyr Asn Tyr Tyr Gly Ala Asp Asn Gln Ser Glu
1               5                   10                  15

Cys Asp Tyr Ala Asp Trp Thr Pro Ser Gly Ala Leu Ile Pro Ala Ile
                20                  25                  30

Tyr Ile Leu Val Phe Leu Leu Gly Thr Thr Gly Asn Gly Leu Val Leu
            35                  40                  45

Trp Thr Val Phe Trp Ser Ser Arg Glu Lys Arg Arg Ser Ala Asp Ile
    50                  55                  60

Phe Ile Ala Ser Leu Ala Val Ala Asp Leu Thr Phe Val Val Thr Leu
65                  70                  75                  80

Pro Leu Trp Ala Thr Tyr Thr Tyr Arg Glu Phe Asp Trp Pro Phe Gly
                85                  90                  95

Thr Phe Ser Cys Lys Leu Ser Ser Tyr Leu Ile Phe Val Asn Met Tyr
                100                 105                 110

Ala Ser Val Phe Cys Leu Thr Gly Leu Ser Phe Asp Arg Tyr Leu Ala
            115                 120                 125

Ile Val Arg Pro Val Ala Asn Ala Arg Leu Arg Leu Arg Val Ser Gly
        130                 135                 140

Ala Val Ala Thr Ala Val Leu Trp Val Leu Ala Ala Leu Leu Ala Val
145                 150                 155                 160

Pro Val Met Val Phe Arg Ser Thr Asp Ile Pro Glu Asn Ser Thr Lys
                165                 170                 175
```

-continued

Thr Gln Cys Tyr Met Asp Tyr Ser Met Val Ala Thr Ser Asn Ser Glu
              180                 185                 190

Trp Ala Trp Glu Val Gly Leu Gly Val Ser Ser Thr Ala Val Gly Phe
          195                 200                 205

Val Val Pro Phe Ile Ile Met Leu Thr Cys Tyr Phe Phe Ile Ala Gln
      210                 215                 220

Thr Ile Ala Gly His Phe Arg Lys Glu Arg Ile Glu Gly Leu Arg Lys
225                 230                 235                 240

Arg Arg Arg Leu Leu Ser Ile Ile Val Val Leu Val Val Thr Phe Ala
              245                 250                 255

Leu Cys Trp Met Pro Tyr His Leu Val Lys Thr Leu Tyr Met Leu Gly
              260                 265                 270

Asn Leu Leu His Trp Pro Cys Asp Phe Asp Ser Phe Leu Met Asn Val
              275                 280                 285

Phe Pro Tyr Cys Thr Cys Ile Ser Tyr Val Asn Ser Cys Leu Asn Pro
          290                 295                 300

Phe Leu Tyr Ala Phe Phe Asp Pro Arg Phe Arg Arg Ala Cys Thr Ser
305                 310                 315                 320

Met Leu Cys Cys Asp Gln Ser Gly Cys Lys Gly Ser Pro His Ser Ser
                  325                 330                 335

Ser Ala Glu Lys Ser Ala Ser Tyr Ser Ser Gly His Ser Gln Gly Pro
              340                 345                 350

Gly Pro Asn Met Cys Lys Gly Gly Glu Pro Met His Glu Lys Ser Ile
              355                 360                 365

Pro Tyr Ser Gln Glu Thr Leu Val Asp
          370                 375

<210> SEQ ID NO 26
<211> LENGTH: 377
<212> TYPE: PRT
<213> ORGANISM: Mus musculus

<400> SEQUENCE: 26

Met Glu Asp Asp Gly Tyr Asn Tyr Tyr Gly Ala Asp Asn Gln Ser Glu
1               5                   10                  15

Cys Asp Tyr Ala Asp Trp Lys Pro Ser Gly Ala Leu Ile Pro Ala Ile
              20                  25                  30

Tyr Met Leu Val Phe Leu Leu Gly Thr Thr Gly Asn Gly Leu Val Leu
          35                  40                  45

Trp Thr Val Phe Arg Thr Ser Arg Glu Lys Arg Arg Ser Ala Asp Ile
      50                  55                  60

Phe Ile Ala Ser Leu Ala Val Ala Asp Leu Thr Phe Val Val Thr Leu
65                  70                  75                  80

Pro Leu Trp Ala Thr Tyr Thr Tyr Arg Glu Phe Asp Trp Pro Phe Gly
              85                  90                  95

Thr Phe Ser Cys Lys Leu Ser Ser Tyr Leu Ile Phe Val Asn Met Tyr
          100                 105                 110

Ala Ser Val Phe Cys Leu Thr Gly Leu Ser Phe Asp Arg Tyr Leu Ala
      115                 120                 125

Ile Val Arg Pro Val Ala Asn Ala Arg Leu Arg Leu Arg Val Ser Gly
          130                 135                 140

Ala Val Ala Thr Ala Val Leu Trp Val Leu Ala Ala Leu Leu Ala Val
145                 150                 155                 160

Pro Val Met Val Phe Arg Ser Thr Asp Ala Ser Glu Asn Gly Thr Lys

```
                165                 170                 175
Ile Gln Cys Tyr Met Asp Tyr Ser Met Val Ala Thr Ser Asn Ser Glu
            180                 185                 190

Trp Ala Trp Glu Val Gly Leu Gly Val Ser Ser Thr Ala Val Gly Phe
        195                 200                 205

Val Val Pro Phe Thr Ile Met Leu Thr Cys Tyr Phe Phe Ile Ala Gln
210                 215                 220

Thr Ile Ala Gly His Phe Arg Lys Glu Arg Ile Glu Gly Leu Arg Lys
225                 230                 235                 240

Arg Arg Arg Leu Leu Ser Ile Ile Val Leu Val Val Thr Phe Ala
                245                 250                 255

Leu Cys Trp Met Pro Tyr His Leu Val Lys Thr Leu Tyr Met Leu Gly
            260                 265                 270

Ser Leu Leu His Trp Pro Cys Asp Phe Asp Ile Phe Leu Met Asn Val
        275                 280                 285

Phe Pro Tyr Cys Thr Cys Ile Ser Tyr Val Asn Ser Cys Leu Asn Pro
290                 295                 300

Phe Leu Tyr Ala Phe Phe Asp Pro Arg Phe Arg Gln Ala Cys Thr Ser
305                 310                 315                 320

Met Leu Cys Cys Asp Gln Ser Gly Cys Lys Gly Thr Pro His Ser Ser
                325                 330                 335

Ser Ala Glu Lys Ser Ala Ser Tyr Ser Ser Gly His Ser Gln Gly Pro
            340                 345                 350

Gly Pro Asn Met Gly Lys Gly Gly Glu Gln Met His Glu Lys Ser Ile
        355                 360                 365

Pro Tyr Ser Gln Glu Thr Leu Val Asp
370                 375

<210> SEQ ID NO 27
<211> LENGTH: 33
<212> TYPE: DNA
<213> ORGANISM: Mus musculus

<400> SEQUENCE: 27
catgccagtc agaacattca tgtttggtta agc                              33

<210> SEQ ID NO 28
<211> LENGTH: 21
<212> TYPE: DNA
<213> ORGANISM: Mus musculus

<400> SEQUENCE: 28
aaggcttcca acttgcacac a                                           21

<210> SEQ ID NO 29
<211> LENGTH: 27
<212> TYPE: DNA
<213> ORGANISM: Mus musculus

<400> SEQUENCE: 29
caacagggtc acagttatcc tctgacg                                     27

<210> SEQ ID NO 30
<211> LENGTH: 48
<212> TYPE: DNA
<213> ORGANISM: Mus musculus

<400> SEQUENCE: 30
```
agatctagtc agagccttat atacactaat ggaaacacct atttacat                48

<210> SEQ ID NO 31
<211> LENGTH: 21
<212> TYPE: DNA
<213> ORGANISM: Mus musculus

<400> SEQUENCE: 31
aaagtttcca accgattttc t                                             21

<210> SEQ ID NO 32
<211> LENGTH: 27
<212> TYPE: DNA
<213> ORGANISM: Mus musculus

<400> SEQUENCE: 32
tctcaaaata cacatgttcc tctcacg                                       27

<210> SEQ ID NO 33
<211> LENGTH: 48
<212> TYPE: DNA
<213> ORGANISM: Mus musculus

<400> SEQUENCE: 33
agatctagtc agaatcttgt tcatagtagt ggaaacaccc atttagat                48

<210> SEQ ID NO 34
<211> LENGTH: 21
<212> TYPE: DNA
<213> ORGANISM: Mus musculus

<400> SEQUENCE: 34
aaagtttccg accgactttc t                                             21

<210> SEQ ID NO 35
<211> LENGTH: 27
<212> TYPE: DNA
<213> ORGANISM: Mus musculus

<400> SEQUENCE: 35
tttcaagctt ctcatgttcc actcacg                                       27

<210> SEQ ID NO 36
<211> LENGTH: 48
<212> TYPE: DNA
<213> ORGANISM: Mus musculus

<400> SEQUENCE: 36
agatctgatc agagtcttgt acatagaact ggaaataccc atttagac                48

<210> SEQ ID NO 37
<211> LENGTH: 27
<212> TYPE: DNA
<213> ORGANISM: Mus musculus

<400> SEQUENCE: 37
tttcaagctt cacatattcc attcaca                                       27

<210> SEQ ID NO 38
<211> LENGTH: 48
<212> TYPE: DNA
<213> ORGANISM: Mus musculus

<400> SEQUENCE: 38
cggtccgacc agtctctggt gcacaggacc ggcaacacac acctggat                48

<210> SEQ ID NO 39
<211> LENGTH: 21
<212> TYPE: DNA
<213> ORGANISM: Mus musculus

<400> SEQUENCE: 39
aaggtgagca ataggttctc c                                            21

<210> SEQ ID NO 40
<211> LENGTH: 27
<212> TYPE: DNA
<213> ORGANISM: Mus musculus

<400> SEQUENCE: 40
tttcaggcca gccacatccc attcacc                                      27

<210> SEQ ID NO 41
<211> LENGTH: 30
<212> TYPE: DNA
<213> ORGANISM: Mus musculus

<400> SEQUENCE: 41
ggattcccct tcaatatcaa tgccatgaac                                   30

<210> SEQ ID NO 42
<211> LENGTH: 57
<212> TYPE: DNA
<213> ORGANISM: Mus musculus

<400> SEQUENCE: 42
cgcataagaa gtaaaagtaa taattacgca acatattatg ccgattcagt gaaagac     57

<210> SEQ ID NO 43
<211> LENGTH: 27
<212> TYPE: DNA
<213> ORGANISM: Mus musculus

<400> SEQUENCE: 43
ggcccatatt tatatgctat ggactac                                      27

<210> SEQ ID NO 44
<211> LENGTH: 30
<212> TYPE: DNA
<213> ORGANISM: Mus musculus

<400> SEQUENCE: 44
gggttctcat tgaccaacta tggtgtgacc                                   30

<210> SEQ ID NO 45
<211> LENGTH: 48
<212> TYPE: DNA
<213> ORGANISM: Mus musculus

<400> SEQUENCE: 45
gtggtatggg gtgacgggac cacaagttct cattcaactc tcatgtcc               48

<210> SEQ ID NO 46
<211> LENGTH: 24
<212> TYPE: DNA
<213> ORGANISM: Mus musculus

<400> SEQUENCE: 46
tccaactggg ggtcatttac ttat                                           24

<210> SEQ ID NO 47
<211> LENGTH: 30
<212> TYPE: DNA
<213> ORGANISM: Mus musculus

<400> SEQUENCE: 47
ggattcactt tcagtagcta tgccatgtct                                     30

<210> SEQ ID NO 48
<211> LENGTH: 48
<212> TYPE: DNA
<213> ORGANISM: Mus musculus

<400> SEQUENCE: 48
tccattagta gtggtggaag tatctactat ccagagagtg tgaagggc                 48

<210> SEQ ID NO 49
<211> LENGTH: 33
<212> TYPE: DNA
<213> ORGANISM: Mus musculus

<400> SEQUENCE: 49
ggccgggggg gcagccaggc ctggtttgct tac                                 33

<210> SEQ ID NO 50
<211> LENGTH: 48
<212> TYPE: DNA
<213> ORGANISM: Mus musculus

<400> SEQUENCE: 50
tctattagta gtggtggtag tatctacctt ccagacagtt tgaagggc                 48

<210> SEQ ID NO 51
<211> LENGTH: 33
<212> TYPE: DNA
<213> ORGANISM: Mus musculus

<400> SEQUENCE: 51
ggccggggaa atagctccgc ctggtttgct tac                                 33

<210> SEQ ID NO 52
<211> LENGTH: 30
<212> TYPE: DNA
<213> ORGANISM: Mus musculus

<400> SEQUENCE: 52
ggcttcacct ttagctccta cgccatgagc                                     30

<210> SEQ ID NO 53
<211> LENGTH: 48
<212> TYPE: DNA
<213> ORGANISM: Mus musculus

<400> SEQUENCE: 53
tctatctcta gcggcggcag catctacctg cctgactccc tgaagggc                 48

<210> SEQ ID NO 54
<211> LENGTH: 33
<212> TYPE: DNA
<213> ORGANISM: Mus musculus

<400> SEQUENCE: 54

| ggcagaggca attcctctgc ctggtttgcc tat | 33 |

<210> SEQ ID NO 55
<211> LENGTH: 1140
<212> TYPE: DNA
<213> ORGANISM: Homo sapiens

<400> SEQUENCE: 55

| atggaggaag gtggtgattt tgacaactac tatggggcag acaaccagtc tgagtgtgag | 60 |
| tacacagact ggaaatcctc gggggccctc atccctgcca tctacatgtt ggtcttcctc | 120 |
| ctgggcacca cgggcaacgg tctggtgctc tggaccgtgt tcggagcag ccgggagaag | 180 |
| aggcgctcag ctgatatctt cattgctagc ctggcggtgg ctgacctgac cttcgtggtg | 240 |
| acgctgcccc tgtgggctac ctacacgtac cgggactatg actggccctt gggaccttc | 300 |
| ttctgcaagc tcagcagcta cctcatcttc gtcaacatgt acgccagcgt cttctgcctc | 360 |
| accggcctca gcttcgaccg ctacctggcc atcgtgaggc cagtggccaa tgctcggctg | 420 |
| aggctgcggg tcagcggggc cgtggccacg gcagttcttt gggtgctggc cgccctcctg | 480 |
| gccatgcctg tcatggtgtt acgcaccacc ggggacttgg agaacaccac taaggtgcag | 540 |
| tgctacatgg actactccat ggtggccact gtgagctcag agtgggcctg ggaggtgggc | 600 |
| cttggggtct cgtccaccac cgtgggcttt gtggtgccct tcaccatcat gctgacctgt | 660 |
| tacttcttca tcgcccaaac catcgctggc cacttccgca aggaacgcat cgagggcctg | 720 |
| cggaagcggc gccggctgct cagcatcatc gtggtgctgg tggtgacctt gccctgtgc | 780 |
| tggatgccct accacctggt gaagacgctg tacatgctgg gcagcctgct gcactggccc | 840 |
| tgtgactttg acctcttcct catgaacatc ttcccctact gcacctgcat cagctacgtc | 900 |
| aacagctgcc tcaaccccctt cctctatgcc tttttcgacc cccgcttccg ccaggcctgc | 960 |
| acctccatgc tctgctgtgg ccagagcagg tgcgcaggca cctcccacag cagcagtggg | 1020 |
| gagaagtcag ccagctactc ttcggggcac agccaggggc ccggcccaa catgggcaag | 1080 |
| ggtggagaac agatgcacga gaaatccatc ccctacagcc aggagaccct tgtggttgac | 1140 |

<210> SEQ ID NO 56
<211> LENGTH: 1140
<212> TYPE: DNA
<213> ORGANISM: Rhesus macaque

<400> SEQUENCE: 56

| atggaggaag gtggtgattt tgacaactac tatggggcag acaaccagtc tgagtgtgag | 60 |
| tacacagact ggaaatcctc gggggccctc atccctgcca tctacatgtt ggtcttcctc | 120 |
| ctgggcacca cgggcaacgg tctggtgctc tggaccgtgt tcggagcag ccgggagaag | 180 |
| aggcgctcgg ctgatatctt catcgccagc ctggcagtgg ctgacctgac cttcgtggtg | 240 |
| acgctgcccc tgtgggctac ctacacgtac cgggactatg actggccctt gggaccttc | 300 |
| tcctgcaagc tcagcagcta cctcatctttt gtcaacatgt acgccagtgt cttctgcctc | 360 |
| accggcctca gcttcgaccg ctacctggcc atcgtgaggc cagtggccaa cgctcggctg | 420 |
| aggctgcggg tcagcggggc cgtggccacg gcggtcctgt gggtgctggc cgccctcctg | 480 |
| gccatgcctg tcatggtgtt ccgcaccacc ggggacctgg agaacaccac caaggtgcag | 540 |
| tgctacatgg actactccat ggtggccact gtgagctcgg attgggcctg ggaggtgggc | 600 |

```
ctgggggtct cgtccaccac cgtgggcttc gtggtgccct tcaccatcat gctgacctgt        660
tacttcttca tcgcccaaac catcgctggc cacttccgca aggagcgcat cgagggcctg        720
cggaagcggc gccggctgct cagcatcatc gtggtgctgg tggtgacatt tgccctgtgc        780
tggatgccct accacctggt gaagacgctg tacatgctgg gcagtctgct gcactggccc        840
tgtgactttg acctcttcct catgaacgtc ttccccact gcacctgcat cagctacgtc         900
aacagctgcc tcaaccctt cctctatgcc ttcttcgatc cccgcttccg ccaggcctgc         960
acctccatgc tctgctgtgg ccagagcaga tgtgcgggca cctcccacag cagcagtggg       1020
gagaagtcag ccagctactc ttcggggcac agccaggggc ctggccccaa catgggcaag       1080
ggtggagaac agatgcacga gaaatccatc ccctacagcc aggagaccct tgtggttgac       1140
```

<210> SEQ ID NO 57
<211> LENGTH: 1131
<212> TYPE: DNA
<213> ORGANISM: Rattus norvegicus

<400> SEQUENCE: 57

```
atggaagatg atggttacaa ctactacggg gctgacaacc agtctgaatg tgactacgca         60
gactggacgc cctctggagc tctcatccct gccatctaca ttctggtttt ccttctaggc        120
accacaggca atggcctggt gctctggacc gtgttttgga gcagccgaga aaagagacgc        180
tcagctgaca tcttcattgc cagcctggct gtggctgact tgacctttgt ggtgactttg        240
ccactgtggg ccacttatac ctaccgggag tttgactggc cttttggaac cttctcttgc        300
aagctcagca gctacctcat ctttgtcaac atgtacgcca gtgtcttttg cctcaccggc        360
ctcagctttg accgatacct ggccattgtc aggccagtgg ctaacgctcg actaaggctg        420
cgagtcagcg gggccgtggc cacagcagtc ttgtgggtgc tggctgccct tctagctgtg        480
cccgtcatgg tgttccgttc cactgacatc ccggaaaaca gcaccaagac ccagtgctac        540
atggactact ctatggtggc cacttcaaac tcagagtggg cctgggaggt gggccttggg       600
gtgtcctcca ctgctgtggg ctttgtggtg cccttcatca tcatgctgac ctgttacttc       660
ttcattgccc aaaccatcgc tggccatttc gaaaggagc gcatcgaggg cctgcggaag        720
aggcgccggc tgctgagcat catcgtggtg ctggtggtga ccttgccct gtgctggatg        780 ccttaccacc tggtgaagac tctctacatg ctgggcaatt gctgcactg gccctgtgac        840 tttgacagct tcctcatgaa tgtctttccc tattgcacct gcatcagtta cgtcaacagc        900
tgcctcaacc cttcctcta tgccttctt gaccccgat ttcgccgagc tgcacctcc           960 atgctctgct gtgaccagag cggggtgcaaa ggcagccctc acagcagcag tgcagagaaa     1020
tctgccagtt attcttctgg gcacagccag ggccccggcc caacatgtg caagggagga       1080 gaaccgatgc atgagaaatc tatcccctat agccaagaaa cccttgtgga c              1131
```

<210> SEQ ID NO 58
<211> LENGTH: 1131
<212> TYPE: DNA
<213> ORGANISM: Mus musculus

<400> SEQUENCE: 58

```
atggaagatg atggttacaa ctactatggg gctgacaacc agtctgaatg cgactacgca         60
gactggaagc cctctggagc gctcattcct gccatctaca tgttggtttt tcttctaggc        120
accacaggca atggcctggt gctctggacc gtgtttcgaa ccagccgcga aaagagacgc        180
tcagctgaca tcttcattgc cagcctggca gtggctgact tgacctttgt ggtgactttg        240
```

```
ccactgtggg ccacttatac ctaccgggag tttgactggc cttttggaac cttctcttgc    300
aagctcagca gctacctcat ctttgtcaac atgtacgcca gtgtcttttg cctcaccggc    360
ctcagctttg accgatacct ggccattgtc aggccgtgg ccaatgctcg gctaaggctg     420
cgagtcagcg gggccgtggc cacagcagtc ttatgggtgc tggctgccct tctagctgtg    480
cctgtcatgg tgttccgttc acagacgcc tcggaaaatg caccaagat ccagtgctac      540
atggactact ctatggtggc cacttcaaac tcagagtggg cctgggaggt gggccttggg    600
gtgtcctcca ctgccgtggg ctttgtggtg cccttcacca tcatgctgac atgttacttc    660
ttcattgccc aaaccatcgc tggccatttc gaaaggagc gcattgaggg cctgcggaag     720
aggcgccggc tgctcagcat tatcgtggtg cttgtagtga cctttgccct gtgctggatg    780
ccttaccacc tggtgaagac tctctacatg ctgggcagtt tgctgcactg gcctgtgac     840
tttgacatct tcctcatgaa tgtctttccg tactgcacct gcatcagtta tgtcaacagc    900
tgcctcaacc cctttctcta tgccttcttt gaccccgat ttcgccaagc ctgcacctcc     960
atgctctgct gtgatcagag cgggtgcaaa ggcaccctc acagcagtag tgccgagaag    1020
tcagccagtt attcttccgg gcacagccag ggccctggcc ccaacatggg aaagggagga   1080
gagcagatgc atgagaaatc gattccctat agtcaagaaa cccttgtgga c            1131
```

<210> SEQ ID NO 59
<211> LENGTH: 108
<212> TYPE: PRT
<213> ORGANISM: Mus musculus

<400> SEQUENCE: 59

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile His Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly His Ser Tyr Pro Leu
                85                  90                  95

Thr Phe Gly Gly Gly Thr Lys Leu Glu Ile Lys Arg
            100                 105

<210> SEQ ID NO 60
<211> LENGTH: 113
<212> TYPE: PRT
<213> ORGANISM: Mus musculus

<400> SEQUENCE: 60

Asp Val Val Met Thr Gln Thr Pro Phe Ser Leu Pro Val Ser Leu Gly
1               5                   10                  15

Asp Gln Ala Ser Met Ser Cys Arg Ser Ser Gln Ser Leu Ile Tyr Thr
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Val Gly Ser Gly Ser Gly Thr Asp Phe Thr Leu Thr Ile
65                  70                  75                  80

Ser Arg Val Glu Ala Glu Asp Leu Gly Val Tyr Phe Cys Ser Gln Asn
                85                  90                  95

Thr His Val Pro Leu Thr Phe Gly Ala Gly Thr Lys Leu Glu Leu Lys
            100                 105                 110

Arg

<210> SEQ ID NO 61
<211> LENGTH: 113
<212> TYPE: PRT
<213> ORGANISM: Mus musculus

<400> SEQUENCE: 61

Asp Val Leu Met Thr Gln Thr Pro Leu Ser Leu Thr Val Ser Leu Gly
1               5                   10                  15

Asp Gln Ala Ser Ile Ser Cys Arg Ser Ser Gln Asn Leu Val His Ser
            20                  25                  30

Ser Gly Asn Thr His Leu Asp Trp Tyr Leu Gln Lys Pro Gly Gln Ser
        35                  40                  45

Pro Lys Leu Leu Ile Tyr Lys Val Ser Asp Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Lys Val Glu Ala Glu Asp Leu Gly Val Tyr Tyr Cys Phe Gln Ala
                85                  90                  95

Ser His Val Pro Leu Thr Phe Gly Gly Gly Thr Lys Leu Glu Leu Lys
            100                 105                 110

Arg

<210> SEQ ID NO 62
<211> LENGTH: 113
<212> TYPE: PRT
<213> ORGANISM: Mus musculus

<400> SEQUENCE: 62

Asp Val Leu Met Thr Gln Thr Pro Leu Ser Leu Pro Val Ser Leu Gly
1               5                   10                  15

Asp Gln Ala Ser Ile Ser Cys Arg Ser Asp Gln Ser Leu Val His Arg
            20                  25                  30

Thr Gly Asn Thr His Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser His Ile Pro Phe Thr Phe Gly Ser Gly Thr Lys Leu Glu Ile Lys
            100                 105                 110

Arg

<210> SEQ ID NO 63
<211> LENGTH: 113
<212> TYPE: PRT
<213> ORGANISM: Artificial Sequence
<220> FEATURE:
<223> OTHER INFORMATION: synthetic construct

<400> SEQUENCE: 63

Asp Val Leu Met Thr Gln Ser Pro Leu Ser Leu Pro Val Thr Leu Gly
1               5                   10                  15

Gln Pro Ala Ser Ile Ser Cys Arg Ser Asp Gln Ser Leu Val His Arg
            20                  25                  30

Thr Gly Asn Thr His Leu Asp Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Ile Pro Phe Thr Phe Gly Gln Gly Thr Lys Val Glu Ile Lys
            100                 105                 110

Arg

<210> SEQ ID NO 64
<211> LENGTH: 120
<212> TYPE: PRT
<213> ORGANISM: Mus musculus

<400> SEQUENCE: 64

Glu Val Gln Leu Ile Glu Thr Gly Gly Gly Leu Val Gln Pro Thr Gly
1               5                   10                  15

Ser Leu Gln Leu Ser Cys Ala Ala Ser Gly Phe Pro Phe Asn Ile Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Ser Ala Met Tyr
                85                  90                  95

Phe Cys Val Arg Gly Pro Tyr Leu Tyr Ala Met Asp Tyr Trp Gly Gln
            100                 105                 110

Gly Thr Ser Val Thr Val Ser Ser
        115                 120

<210> SEQ ID NO 65
<211> LENGTH: 116
<212> TYPE: PRT
<213> ORGANISM: Mus musculus

<400> SEQUENCE: 65

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val Thr Trp Leu Arg Gln Pro Pro Gly Lys Gly Leu Glu Trp Leu
        35                  40                  45

Gly Val Val Trp Gly Asp Gly Thr Thr Ser Ser His Ser Thr Leu Met
    50                  55                  60

Ser Arg Leu Ser Leu Ser Arg Asp Thr Ser Lys Asn Gln Val Phe Leu
65                  70                  75                  80

Asn Leu Asn Ser Leu Gln Thr Asp Asp Thr Ala Thr Tyr Tyr Cys Ala
                85                  90                  95

Arg Ser Asn Trp Gly Ser Phe Thr Tyr Trp Gly Gln Gly Thr Leu Val
            100                 105                 110

Thr Val Ser Ala
        115

<210> SEQ ID NO 66
<211> LENGTH: 119
<212> TYPE: PRT
<213> ORGANISM: Mus musculus

<400> SEQUENCE: 66

Glu Val Lys Leu Val Glu Ser Gly Gly Asn Leu Val Lys Pro Gly Gly
1               5                   10                  15

Ser Gln Lys Leu Ser Cys Ser Ala Ser Gly Phe Thr Phe Ser Ser Tyr
            20                  25                  30

Ala Met Ser Trp Val Pro Gln Thr Pro Lys Lys Arg Leu Glu Trp Val
        35                  40                  45

Ala Ser Ile Ser Ser Gly Gly Ser Ile Tyr Tyr Pro Glu Ser Val Lys
    50                  55                  60

Gly Arg Phe Thr Ile Ser Arg Asp His Ala Arg Asn Ile Leu Tyr Leu
65                  70                  75                  80

Gln Met Ser Ser Leu Arg Ser Glu Asp Thr Ala Met Tyr Phe Cys Ala
                85                  90                  95

Arg Gly Arg Gly Gly Ser Gln Ala Trp Phe Ala Tyr Trp Gly Gln Gly
            100                 105                 110

Thr Leu Val Thr Val Ser Ala
        115

<210> SEQ ID NO 67
<211> LENGTH: 119
<212> TYPE: PRT
<213> ORGANISM: Mus musculus

<400> SEQUENCE: 67

Glu Ile Lys Leu Val Glu Ser Gly Gly Gly Leu Val Lys Pro Arg Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Ser Ile Tyr Leu Pro Asp Ser Leu Lys
    50                  55                  60

Gly Arg Phe Thr Ile Ser Arg Asp Asn Ala Trp Asn Ile Leu Tyr Leu
65                  70                  75                  80

Gln Met Asn Ser Leu Lys Ser Glu Asp Thr Ala Met Tyr Tyr Cys Thr
                85                  90                  95

Arg Gly Arg Gly Asn Ser Ser Ala Trp Phe Ala Tyr Trp Gly Gln Gly
            100                 105                 110

Thr Leu Val Thr Val Ser Ala
        115

<210> SEQ ID NO 68

-continued

<211> LENGTH: 119
<212> TYPE: PRT
<213> ORGANISM: Artificial Sequence
<220> FEATURE:
<223> OTHER INFORMATION: synthetic construst

<400> SEQUENCE: 68

Glu Ile Gln Leu Val Glu Ser Gly Gly Gly Leu Val Lys Pro Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Ile Tyr Leu Pro Asp Ser Leu Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Thr
                85                  90                  95

Arg Gly Arg Gly Asn Ser Ser Ala Trp Phe Ala Tyr Trp Gly Gln Gly
            100                 105                 110

Thr Leu Val Thr Val Ser Ser
        115

<210> SEQ ID NO 69
<211> LENGTH: 324
<212> TYPE: DNA
<213> ORGANISM: Mus musculus

<400> SEQUENCE: 69
gacatccaga tgaaccagtc tccatccagt ctgtctgcat cccttggaga cacaattacc    60
atcacttgcc atgccagtca gaacattcat gtttggttaa gctggtacca gcagaaacca   120
ggaaacattc ctaaactatt gatctataag gcttccaact tgcacacagg cgtcccatca   180
aggtttagtg gcagtgggtc tggaacaggt ttcacattaa ccatcagcag cctgcagcct   240
gaagacattg ccacttacta ctgtcaacag ggtcacagtt atcctctgac gttcggtgga   300
ggcaccaagc tggaaatcaa acgg                                          324

<210> SEQ ID NO 70
<211> LENGTH: 339
<212> TYPE: DNA
<213> ORGANISM: Mus musculus

<400> SEQUENCE: 70
gatgttgtga tgacccaaac tccattctcc ctgcctgtca gtcttggaga tcaagcctcc    60
atgtcttgca gatctagtca gagccttata tacactaatg gaaacaccta tttacattgg   120
tacctgcaga agccaggcca gtctccaaag ctcctgatct acaaagtttc caaccgattt   180
tctggggtcc cagacaggtt cgttggcagt ggatcaggga cagatttcac tctcacgatc   240
agccgagtgg aggctgagga tctgggagtt tatttctgct ctcaaaatac acatgttcct   300
ctcacgttcg gtgctgggac caagctggag ctgaaacgg                          339

<210> SEQ ID NO 71
<211> LENGTH: 339
<212> TYPE: DNA
<213> ORGANISM: Mus musculus

<400> SEQUENCE: 71

```
gatgttttga tgacccaaac tccactctcc ctgactgtca gtcttggaga tcaagcctcc    60
atctcttgca gatctagtca gaatcttgtt catagtagtg aaacaccca tttagattgg    120 tacctgcaga aaccaggcca gtctccaaag ctcctgatct acaaagtttc cgaccgactt   180
tctggggtcc cagacaggtt cagtggcagt ggatcaggga catatttcac actcaagatc   240
agcaaagtgg aggctgagga tctgggagtt tattactgct ttcaagcttc tcatgttcca   300
ctcacgttcg gtggtgggac caagctggag ctgaaacgg                          339
```

<210> SEQ ID NO 72
<211> LENGTH: 339
<212> TYPE: DNA
<213> ORGANISM: Mus musculus

<400> SEQUENCE: 72

```
gatgttttga tgacccaaac tccactctcc ctgcctgtca gtcttggaga tcaagcctcc   60
atctcttgca gatctgatca gagtcttgta catagaactg aaataccca tttagactgg    120 tacctgcaga agccaggcca gtctccaaag ctcctgatct acaaagtttc caaccgattt   180
tctggggtcc cagacaggtt cagtggcagt ggctcaggga cagatttcac actcaagatt   240
agtagagtgg aggctgagga tttgggagtt tattactgct ttcaagcttc acatattcca   300
ttcacattcg gctcggggac aaagttggaa ataaaacgg                          339
```

<210> SEQ ID NO 73
<211> LENGTH: 339
<212> TYPE: DNA
<213> ORGANISM: Artificial Sequence
<220> FEATURE:
<223> OTHER INFORMATION: synthetic construct

<400> SEQUENCE: 73

```
gacgtgctga tgacccagtc tcccctgagc ctgcctgtga cactgggaca gccagccagc   60
atctcctgcc ggtccgacca gtctctggtg cacaggaccg gcaacacaca cctggattgg   120
taccagcaga ggccaggaca gtccccaaga ctgctgatct ataaggtgag caataggttc   180
tccggcgtgc ctgaccgctt ttctggcagc ggctccggca ccgatttcac actgaagatc   240
tctcgggtgg aggccgagga tgtgggcgtg tactattgtt ttcaggccag ccacatccca   300 ttcaccttg gccagggcac aaaggtggag atcaagcgt                           339
```

<210> SEQ ID NO 74
<211> LENGTH: 360
<212> TYPE: DNA
<213> ORGANISM: Mus musculus

<400> SEQUENCE: 74

```
gaggtgcagc ttattgagac tggtggagga ttggtgcagc ctacagggtc attgcaactc   60
tcatgtgcag cctctggatt cccccttcaat atcaatgcca tgaactgggt ccgccaggct   120
ccaggaaagg gtttggaatg ggttgcccgc ataagaagta aaagtaataa ttacgcaaca   180
tattatgccg attcagtgaa agacaggttc accatctcca gagatgattc acaaagcata   240
ctctatctgc aaatgaacaa cttgaaaact gaggactcag ccatgtattt ctgtgtgaga   300
ggcccatatt tatatgctat ggactactgg ggtcaaggaa cctcagtcac cgtctcctca   360
```

<210> SEQ ID NO 75
<211> LENGTH: 348
<212> TYPE: DNA

<213> ORGANISM: Mus musculus

<400> SEQUENCE: 75

```
caggtgcagt tgaaggagtc aggacctggc ctggtggcgc cctcacagag cctgtccatc    60
acatgcactg tctcagggtt ctcattgacc aactatggtg tgacctggct tcgccagcct   120
ccagggaagg gtctggaatg gctgggagtg gtatggggtg acgggaccac aagttctcat   180
tcaactctca tgtccagact gagcctcagc agggatacct ccaagaacca agttttctta   240
aaccttaaca gtctgcagac tgatgacaca gccacgtact actgtgccag atccaactgg   300
gggtcattta cttattgggg ccaagggact ctggtcactg tctctgcc                348
```

<210> SEQ ID NO 76
<211> LENGTH: 357
<212> TYPE: DNA
<213> ORGANISM: Mus musculus

<400> SEQUENCE: 76

```
gaagtgaagc tggtggagtc tgggggaaac ctagtgaagc ctggagggtc ccaaaaactc    60
tcctgttcag cctctggatt cactttcagt agctatgcca tgtcttgggt tccccaaact   120
ccaaaaaaaa ggctggagtg gtcgcatcc attagtagtg gtggaagtat ctactatcca   180
gagagtgtga agggccgatt caccatctcc agagatcatg ccaggaacat cctgtacctg   240
caaatgagca gtctgaggtc tgaggacacg gccatgtatt tctgtgcaag aggccggggg   300
ggcagccagg cctggtttgc ttactggggc caagggactc tggtcactgt ctctgca      357
```

<210> SEQ ID NO 77
<211> LENGTH: 357
<212> TYPE: DNA
<213> ORGANISM: Mus musculus

<400> SEQUENCE: 77

```
gaaattaaac tggtggagtc tgggggaggc ttagtgaagc ctagagggtc cctgaaactc    60
tcctgtgcag cctctggatt cactttcagt agctatgcca tgtcttgggt tcgtcagact   120
ccagagaaga ggctggagtg gtcgcatct attagtagtg gtggtagtat ctaccttcca   180
gacagtttga agggccgatt taccatctcc agagataatg cctggaacat cctgtacctg   240
caaatgaaca gtctgaagtc tgaagacacg gccatgtatt actgtacaag aggccgggga   300
aatagctccg cctggtttgc ttactggggc caagggactc tggtcactgt ctctgca      357
```

<210> SEQ ID NO 78
<211> LENGTH: 357
<212> TYPE: DNA
<213> ORGANISM: Artificial Sequence
<220> FEATURE:
<223> OTHER INFORMATION: synthetic construct

<400> SEQUENCE: 78

```
gagatccagc tggtggagtc tgaggaggga ctggtgaagc aggaggatc tctgaggctg    60
agctgcgccg cctccggctt cacctttagc tcctacgcca tgagctgggt gaggcaggca   120
ccaggcaagg gactgagtg gtggcctct atctctagcg gcggcagcat ctacctgcct   180
gactccctga agggcaggtt cacaatctct cgcgataacg ccaagaatag cctgtatctg   240
cagatgaact ccctgagggc agaggacacc gccgtgtact attgtacacg gggcagaggc   300
aattcctctg cctggtttgc ctattggggc cagggcaccc tggtgacagt gagctcc      357
```

```
<210> SEQ ID NO 79
<211> LENGTH: 106
<212> TYPE: PRT
<213> ORGANISM: Mus musculus

<400> SEQUENCE: 79

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 80
<211> LENGTH: 106
<212> TYPE: PRT
<213> ORGANISM: Homo sapiens

<400> SEQUENCE: 80

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 81
<211> LENGTH: 106
<212> TYPE: PRT
<213> ORGANISM: Homo sapiens

<400> SEQUENCE: 81

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80
```

```
Ser His Arg Ser Tyr Ser Cys Gln Val Thr His Glu Gly Ser Thr Val
                85                  90                  95
Glu Lys Thr Val Ala Pro Thr Glu Cys Ser
            100                 105

<210> SEQ ID NO 82
<211> LENGTH: 324
<212> TYPE: PRT
<213> ORGANISM: Mus musculus

<400> SEQUENCE: 82

Ala Lys Thr Thr Pro Pro Ser Val Tyr Pro Leu Ala Pro Gly Ser Ala
1               5                   10                  15
Ala Gln Thr Asn Ser Met Val Thr Leu Gly Cys Leu Val Lys Gly Tyr
            20                  25                  30
Phe Pro Glu Pro Val Thr Val Thr Trp Asn Ser Gly Ser Leu Ser Ser
        35                  40                  45
Gly Val His Thr Phe Pro Ala Val Leu Gln Ser Asp Leu Tyr Thr Leu
    50                  55                  60
Ser Ser Ser Val Thr Val Pro Ser Ser Pro Arg Pro Ser Glu Thr Val
65                  70                  75                  80
Thr Cys Asn Val Ala His Pro Ala Ser Ser Thr Lys Val Asp Lys Lys
                85                  90                  95
Ile Val Pro Arg Asp Cys Gly Cys Lys Pro Cys Ile Cys Thr Val Pro
            100                 105                 110
Glu Val Ser Ser Val Phe Ile Phe Pro Pro Lys Pro Lys Asp Val Leu
        115                 120                 125
Thr Ile Thr Leu Thr Pro Lys Val Thr Cys Val Val Val Asp Ile Ser
    130                 135                 140
Lys Asp Asp Pro Glu Val Gln Phe Ser Trp Phe Val Asp Asp Val Glu
145                 150                 155                 160
Val His Thr Ala Gln Thr Gln Pro Arg Glu Glu Gln Phe Asn Ser Thr
                165                 170                 175
Phe Arg Ser Val Ser Glu Leu Pro Ile Met His Gln Asp Trp Leu Asn
            180                 185                 190
Gly Lys Glu Phe Lys Cys Arg Val Asn Ser Ala Ala Phe Pro Ala Pro
        195                 200                 205
Ile Glu Lys Thr Ile Ser Lys Thr Lys Gly Arg Pro Lys Ala Pro Gln
    210                 215                 220
Val Tyr Thr Ile Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                245                 250                 255
Glu Trp Gln Trp Asn Gly Gln Pro Ala Glu Asn Tyr Lys Asn Thr Gln
            260                 265                 270
Pro Ile Met Asn Thr Asn Gly Ser Tyr Phe Val Tyr Ser Lys Leu Asn
        275                 280                 285
Val Gln Lys Ser Asn Trp Glu Ala Gly Asn Thr Phe Thr Cys Ser Val
    290                 295                 300
Leu His Glu Gly Leu His Asn His His Thr Glu Lys Ser Leu Ser His
305                 310                 315                 320
Ser Pro Gly Lys

<210> SEQ ID NO 83
```

```
<211> LENGTH: 326
<212> TYPE: PRT
<213> ORGANISM: Homo sapiens

<400> SEQUENCE: 83
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Cys | Ser | Arg |
| 1 | | | | 5 | | | | | 10 | | | | | 15 | |
| Ser | Thr | Ser | Glu | Ser | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | | 35 | | | | | 40 | | | | | 45 | | |
| Gly | Val | His | Thr | Phe | Pro | Ala | Val | Leu | Gln | Ser | Ser | Gly | Leu | Tyr | Ser |
| | | | 50 | | | | | 55 | | | | | 60 | | |
| Leu | Ser | Ser | Val | Val | Thr | Val | Pro | Ser | Ser | Asn | Phe | Gly | Thr | Gln | Thr |
| 65 | | | | | 70 | | | | | 75 | | | | | 80 |
| Tyr | Thr | Cys | Asn | Val | Asp | His | Lys | Pro | Ser | Asn | Thr | Lys | Val | Asp | Lys |
| | | | | 85 | | | | | 90 | | | | | 95 | |
| Thr | Val | Glu | Arg | Lys | Cys | Cys | Val | Glu | Cys | Pro | Pro | Cys | Pro | Ala | Pro |
| | | | 100 | | | | | 105 | | | | | 110 | | |
| Pro | Val | Ala | Gly | Pro | Ser | Val | Phe | Leu | Phe | Pro | Pro | Lys | Pro | Lys | Asp |
| | | | 115 | | | | | 120 | | | | | 125 | | |
| Thr | Leu | Met | Ile | Ser | Arg | Thr | Pro | Glu | Val | Thr | Cys | Val | Val | Val | Asp |
| | 130 | | | | | 135 | | | | | 140 | | | | |
| Val | Ser | His | Glu | Asp | Pro | Glu | Val | Gln | Phe | Asn | Trp | Tyr | Val | Asp | Gly |
| 145 | | | | | 150 | | | | | 155 | | | | | 160 |
| Val | Glu | Val | His | Asn | Ala | Lys | Thr | Lys | Pro | Arg | Glu | Glu | Gln | Phe | Asn |
| | | | | 165 | | | | | 170 | | | | | 175 | |
| Ser | Thr | Phe | Arg | Val | Val | Ser | Val | Leu | Thr | Val | Val | His | Gln | Asp | Trp |
| | | | 180 | | | | | 185 | | | | | 190 | | |
| Leu | Asn | Gly | Lys | Glu | Tyr | Lys | Cys | Lys | Val | Ser | Asn | Lys | Gly | Leu | Pro |
| | | | 195 | | | | | 200 | | | | | 205 | | |
| Ala | Pro | Ile | Glu | Lys | Thr | Ile | Ser | Lys | Thr | Lys | Gly | Gln | Pro | Arg | Glu |
| | 210 | | | | | 215 | | | | | 220 | | | | |
| Pro | Gln | Val | Tyr | Thr | Leu | Pro | Pro | Ser | Arg | Glu | Glu | Met | Thr | Lys | Asn |
| 225 | | | | | 230 | | | | | 235 | | | | | 240 |
| Gln | Val | Ser | Leu | Thr | Cys | Leu | Val | Lys | Gly | Phe | Tyr | Pro | Ser | Asp | Ile |
| | | | | 245 | | | | | 250 | | | | | 255 | |
| Ala | Val | Glu | Trp | Glu | Ser | Asn | Gly | Gln | Pro | Glu | Asn | Asn | Tyr | Lys | Thr |
| | | | 260 | | | | | 265 | | | | | 270 | | |
| Thr | Pro | Pro | Met | Leu | Asp | Ser | Asp | Gly | Ser | Phe | Phe | Leu | Tyr | Ser | Lys |
| | | | 275 | | | | | 280 | | | | | 285 | | |
| Leu | Thr | Val | Asp | Lys | Ser | Arg | Trp | Gln | Gln | Gly | Asn | Val | Phe | Ser | Cys |
| | 290 | | | | | 295 | | | | | 300 | | | | |
| Ser | Val | Met | His | Glu | Ala | Leu | His | Asn | His | Tyr | Thr | Gln | Lys | Ser | Leu |
| 305 | | | | | 310 | | | | | 315 | | | | | 320 |
| Ser | Leu | Ser | Pro | Gly | Lys | | | | | | | | | | |
| | | | | 325 | | | | | | | | | | | |

```
<210> SEQ ID NO 84
<211> LENGTH: 327
<212> TYPE: PRT
<213> ORGANISM: Homo sapiens

<400> SEQUENCE: 84
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Cys | Ser | Arg |
| 1 | | | | 5 | | | | | 10 | | | | | 15 | |

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 85
<211> LENGTH: 318
<212> TYPE: DNA
<213> ORGANISM: Mus musculus

<400> SEQUENCE: 85
gctgatgctg caccaactgt atccatcttc ccaccatcca gtgagcagtt aacatctgga    60
ggtgcctcag tcgtgtgctt cttgaacaac ttctacccca agacatcaa tgtcaagtgg    120 aagattgatg gcagtgaacg acaaaatggc gtcctgaaca gttggactga tcaggacagc    180
aaagacagca cctacagcat gagcagcacc ctcacgttga ccaaggacga gtatgaacga    240
cataacagct atacctgtga ggccactcac aagacatcaa cttcacccat tgtcaagagc    300
```
ttcaacagga atgagtgt                                                         318

<210> SEQ ID NO 86
<211> LENGTH: 318
<212> TYPE: DNA
<213> ORGANISM: Homo sapiens

<400> SEQUENCE: 86
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgt                                                 318

<210> SEQ ID NO 87
<211> LENGTH: 318
<212> TYPE: DNA
<213> ORGANISM: Homo sapiens

<400> SEQUENCE: 87
ggacagccaa aggcagcacc atctgtgacc ctgttcccac ctagctccga ggagctgcag    60
gccaacaagg ccaccctggt gtgcctgatc tccgactttt acccaggagc agtgacagtg   120
gcatggaagg ccgattctag ccctgtgaag gccggcgtgg agaccacaac cccatctaag   180
cagagcaaca ataagtacgc cgcctcctct tatctgtccc tgaccccga gcagtggaag   240
tctcaccgga gctattcctg ccaggtgaca cacgagggca gcacagtgga agaccgtg   300
gcccctacag agtgttcc                                                 318

<210> SEQ ID NO 88
<211> LENGTH: 972
<212> TYPE: DNA
<213> ORGANISM: Mus musculus

<400> SEQUENCE: 88
gccaaaacga caccccatc tgtctatcca ctggcccctg gatctgctgc ccaaactaac    60
tccatggtga ccctgggatg cctggtcaag ggctatttcc ctgagccagt gacagtgacc   120
tggaactctg gatccctgtc cagcggtgtg cacaccttcc cagctgtcct gcagtctgac   180
ctctacactc tgagcagctc agtgactgtc ccctccagcc caggcccag cgagaccgtc   240
acctgcaacg ttgcccaccc ggccagcagc accaaggtgg acaagaaaat tgtgcccagg   300
gattgtggtt gtaagccttg catatgtaca gtcccagaag tatcatctgt cttcatcttc   360
cccccaaagc ccaaggatgt gctcaccatt actctgactc ctaaggtcac gtgtgttgtg   420
gtagacatca gcaaggatga tcccgaggtc cagttcagct ggtttgtaga tgatgtggag   480
gtgcacacag ctcagacgca accccgggag gagcagttca acagcacttt ccgctcagtc   540
agtgaacttc ccatcatgca ccaggactgg ctcaatggca aggagttcaa atgcagggtc   600
aacagtgcag ctttccctgc ccccatcgag aaaaccatct ccaaaaccaa aggcagaccg   660
aaggctccac aggtgtacac cattccacct cccaaggagc agatggccaa ggataaagtc   720
agtctgacct gcatgataac agacttcttc cctgaagaca ttactgtgga gtggcagtgg   780
aatgggcagc cagcggagaa ctacaagaac actcagccca tcatgaacac aaatggctct   840
tacttcgtct acagcaagct caatgtgcag aagagcaact gggaggcagg aaatactttc   900

```
acctgctctg tgttacatga gggcctgcac aaccaccata ctgagaagag cctctcccac    960
tctcctggta aa                                                       972

<210> SEQ ID NO 89
<211> LENGTH: 978
<212> TYPE: DNA
<213> ORGANISM: Homo sapiens

<400> SEQUENCE: 89
gcctccacca agggcccatc ggtcttcccc ctggcgccct gctccaggag cacctccgag     60
agcacagcgg ccctgggctg cctggtcaag gactacttcc ccgaaccggt gacggtgtcg    120
tggaactcag gcgctctgac cagcggcgtg cacaccttcc cagctgtcct acagtcctca    180
ggactctact ccctcagcag cgtggtgacc gtgccctcca gcaacttcgg cacccagacc    240
tacacctgca acgtagatca caagcccagc aacaccaagg tggacaagac agttgagcgc    300
aaatgttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt tgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacac tcccatgctg gactccgac     840 ggctccttct tcctctacag caagctcacc gtggacaaga gcaggtggca gcagggaac     900 gtcttctcat gctccgtgat gcatgaggct ctgcacaacc actacacgca gaagagcctc    960
tccctgtctc cgggtaaa                                                 978

<210> SEQ ID NO 90
<211> LENGTH: 981
<212> TYPE: DNA
<213> ORGANISM: Homo sapiens

<400> SEQUENCE: 90
gcttccacca agggcccatc cgtcttcccc ctggcgccct gctccaggag cacctccgag     60
agcacagccg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc cccatgccc atcatgccca gcacctgagt tcctgggggg accatcagtc    360
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
ggtcagcccc gagagccaca ggtgtacacc ctgcccccat cccaggagga gatgaccaag    720
```

```
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaggcta accgtggaca agagcaggtg gcaggagggg    900
aatgtcttct catgctccgt gatgcatgag gctctgcaca accactacac acagaagagc    960 ctctcccctgt ctctgggtaa a                                            981
```

<210> SEQ ID NO 91
<211> LENGTH: 32
<212> TYPE: PRT
<213> ORGANISM: Homo sapiens

<400> SEQUENCE: 91

Gln Arg Pro Val Asn Leu Thr Met Arg Arg Lys Leu Arg Lys His Asn
1               5                   10                  15

Cys Leu Gln Arg Arg Cys Met Pro Leu His Ser Arg Val Pro Phe Pro
                20                  25                  30

<210> SEQ ID NO 92
<211> LENGTH: 21
<212> TYPE: PRT
<213> ORGANISM: Homo sapiens

<400> SEQUENCE: 92

Leu Arg Lys His Asn Cys Leu Gln Arg Arg Cys Met Pro Leu His Ser
1               5                   10                  15

Arg Val Pro Phe Pro
                20

<210> SEQ ID NO 93
<211> LENGTH: 11
<212> TYPE: PRT
<213> ORGANISM: Homo sapiens

<400> SEQUENCE: 93

Cys Met Pro Leu His Ser Arg Val Pro Phe Pro
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Synthetic construct

<400> SEQUENCE: 94

Gln Arg Arg Cys Met Pro Leu His Ser Arg Val Pro Ala Pro
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Synthetic construct

<400> SEQUENCE: 95

Gln Arg Pro Arg Leu Ser His Lys Arg Val Pro Phe Pro
1               5                   10

<210> SEQ ID NO 96
<211> LENGTH: 13
<212> TYPE: PRT

<213> ORGANISM: Homo sapiens

<400> SEQUENCE: 96

Gln Arg Pro Arg Leu Ser His Lys Arg Val Pro Ala Pro
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Synthetic construct

<400> SEQUENCE: 97

Gln Arg Arg Cys Met Pro Leu His Ser Gly Pro Met Pro Phe
1               5                   10

<210> SEQ ID NO 98
<211> LENGTH: 17
<212> TYPE: PRT
<213> ORGANISM: Artificial Sequence
<220> FEATURE:
<223> OTHER INFORMATION: Synthetic construct

<400> SEQUENCE: 98

Asn Cys Leu Gln Arg Arg Cys Met Pro Leu His Ser Gly Pro Met Pro
1               5                   10                  15

Phe

<210> SEQ ID NO 99
<211> LENGTH: 13
<212> TYPE: PRT
<213> ORGANISM: Artificial Sequence
<220> FEATURE:
<223> OTHER INFORMATION: Synthetic construct

<400> SEQUENCE: 99

Gln Arg Pro Arg Leu Ser His Lys Gly Val Pro Phe Pro
1               5                   10

<210> SEQ ID NO 100
<211> LENGTH: 13
<212> TYPE: PRT
<213> ORGANISM: Homo sapiens

<400> SEQUENCE: 100

Gln Arg Pro Arg Leu Ser His Lys Gly Val Pro Ala Pro
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetic construct

<400> SEQUENCE: 101

Gln Arg Arg Cys Met Pro Leu His Ser Arg Pro Met Pro Phe
1               5                   10

<210> SEQ ID NO 102
<211> LENGTH: 17
<212> TYPE: PRT
<213> ORGANISM: Artificial Sequence
<220> FEATURE:
<223> OTHER INFORMATION: Synthetic construct

<400> SEQUENCE: 102

Asn Cys Leu Gln Arg Arg Cys Met Pro Leu His Ser Arg Pro Met Pro
1               5                   10                  15

Phe

<210> SEQ ID NO 103
<211> LENGTH: 12
<212> TYPE: PRT
<213> ORGANISM: Artificial Sequence
<220> FEATURE:
<223> OTHER INFORMATION: Synthetic construct

<400> SEQUENCE: 103

Gln Arg Pro Arg Leu His Ser Arg Val Pro Phe Pro
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic construct

<400> SEQUENCE: 104

Gln Arg Pro Arg Leu His Ser Arg Val Pro Ala Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic construct

<400> SEQUENCE: 105

Gln Arg Arg Cys Met Pro Leu Ser His Lys Gly Pro Met Pro Phe
1               5                   10                  15

<210> SEQ ID NO 106
<211> LENGTH: 18
<212> TYPE: PRT
<213> ORGANISM: Artificial Sequence
<220> FEATURE:
<223> OTHER INFORMATION: Synthetic construct

<400> SEQUENCE: 106

Asn Cys Leu Gln Arg Arg Cys Met Pro Leu Ser His Lys Gly Pro Met
1               5                   10                  15

Pro Phe

<210> SEQ ID NO 107
<211> LENGTH: 12
<212> TYPE: PRT
<213> ORGANISM: Artificial Sequence
<220> FEATURE:
<223> OTHER INFORMATION: Synthetic construct

<400> SEQUENCE: 107

Gln Arg Pro Arg Leu Ser His Lys Gly Pro Phe Pro
1               5                   10

<210> SEQ ID NO 108
<211> LENGTH: 12
<212> TYPE: PRT

```
<213> ORGANISM: Artificial Sequence
<220> FEATURE:
<223> OTHER INFORMATION: Synthetic construct

<400> SEQUENCE: 108

Gln Arg Pro Arg Leu Ser His Lys Gly Pro Ala Pro
1               5                   10

<210> SEQ ID NO 109
<211> LENGTH: 15
<212> TYPE: PRT
<213> ORGANISM: Artificial Sequence
<220> FEATURE:
<223> OTHER INFORMATION: Synthetic construct

<400> SEQUENCE: 109

Gln Arg Arg Cys Met Pro Leu His Ser Arg Val Pro Met Pro Phe
1               5                   10                  15

<210> SEQ ID NO 110
<211> LENGTH: 18
<212> TYPE: PRT
<213> ORGANISM: Artificial Sequence
<220> FEATURE:
<223> OTHER INFORMATION: synthetic construst

<400> SEQUENCE: 110

Asn Cys Leu Gln Arg Arg Cys Met Pro Leu His Ser Arg Val Pro Met
1               5                   10                  15

Pro Phe

<210> SEQ ID NO 111
<211> LENGTH: 12
<212> TYPE: PRT
<213> ORGANISM: Artificial Sequence
<220> FEATURE:
<223> OTHER INFORMATION: synthetic construct

<400> SEQUENCE: 111

Gln Arg Pro Arg Leu Ser His Arg Val Pro Phe Pro
1               5                   10

<210> SEQ ID NO 112
<211> LENGTH: 12
<212> TYPE: PRT
<213> ORGANISM: Artificial Sequence
<220> FEATURE:
<223> OTHER INFORMATION: synthetic construct

<400> SEQUENCE: 112

Gln Arg Pro Arg Leu Ser His Arg Val Pro Ala Pro
1               5                   10

<210> SEQ ID NO 113
<211> LENGTH: 15
<212> TYPE: PRT
<213> ORGANISM: Artificial Sequence
<220> FEATURE:
<223> OTHER INFORMATION: synthetic construct

<400> SEQUENCE: 113

Gln Arg Arg Cys Met Pro Leu His Ser Lys Gly Pro Met Pro Phe
1               5                   10                  15

<210> SEQ ID NO 114
<211> LENGTH: 18
```

```
<212> TYPE: PRT
<213> ORGANISM: Artificial Sequence
<220> FEATURE:
<223> OTHER INFORMATION: synthetic construct

<400> SEQUENCE: 114

Asn Cys Leu Gln Arg Arg Cys Met Pro Leu His Ser Lys Gly Pro Met
1               5                   10                  15

Pro Phe

<210> SEQ ID NO 115
<211> LENGTH: 15
<212> TYPE: PRT
<213> ORGANISM: Artificial Sequence
<220> FEATURE:
<223> OTHER INFORMATION: synthetic construct

<400> SEQUENCE: 115

Asn Cys Leu Gln Arg Arg Cys Leu Ser His Lys Gly Pro Phe Pro
1               5                   10                  15

<210> SEQ ID NO 116
<211> LENGTH: 13
<212> TYPE: PRT
<213> ORGANISM: Artificial Sequence
<220> FEATURE:
<223> OTHER INFORMATION: synthetic construct

<400> SEQUENCE: 116

Gln Arg Arg Cys Leu Ser His Lys Gly Pro Met Pro Phe
1               5                   10

<210> SEQ ID NO 117
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: Xaa at position 6 is Ser or His
<220> FEATURE:
<221> NAME/KEY: MISC_FEATURE
<222> LOCATION: (7)..(7)
<223> OTHER INFORMATION: Xaa at position 7 is Ser or His
<220> FEATURE:
<221> NAME/KEY: MISC_FEATURE
<222> LOCATION: (9)..(9)
<223> OTHER INFORMATION: Xaa at position 9 is Arg or Gly
<220> FEATURE:
<221> NAME/KEY: MISC_FEATURE
<222> LOCATION: (12)..(12)
<223> OTHER INFORMATION: Xaa at position 12 is Phe or Ala

<400> SEQUENCE: 117

Gln Arg Pro Arg Leu Xaa Xaa Lys Xaa Val Pro Xaa Pro
1               5                   10

<210> SEQ ID NO 118
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: Xaa at position 6 is Ser or His
<220> FEATURE:
```

```
<221> NAME/KEY: MISC_FEATURE
<222> LOCATION: (7)..(7)
<223> OTHER INFORMATION: Xaa at position 7 is Ser or His
<220> FEATURE:
<221> NAME/KEY: MISC_FEATURE
<222> LOCATION: (8)..(8)
<223> OTHER INFORMATION: Xaa at position 8 is Arg or Lys
<220> FEATURE:
<221> NAME/KEY: MISC_FEATURE
<222> LOCATION: (9)..(9)
<223> OTHER INFORMATION: Xaa at position 9 is Val or Gly
<220> FEATURE:
<221> NAME/KEY: MISC_FEATURE
<222> LOCATION: (11)..(11)
<223> OTHER INFORMATION: Xaa at position 11 is Phe or Ala

<400> SEQUENCE: 118

Gln Arg Pro Arg Leu Xaa Xaa Xaa Xaa Pro Xaa Pro
1               5                   10

<210> SEQ ID NO 119
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (11)..(11)
<223> OTHER INFORMATION: Xaa at position 11 is Ser or His
<220> FEATURE:
<221> NAME/KEY: MISC_FEATURE
<222> LOCATION: (12)..(12)
<223> OTHER INFORMATION: Xaa at position 12 is Ser or His
<220> FEATURE:
<221> NAME/KEY: MISC_FEATURE
<222> LOCATION: (13)..(13)
<223> OTHER INFORMATION: Xaa at position 13 is Arg or Gly

<400> SEQUENCE: 119

Asn Cys Leu Gln Arg Arg Cys Met Pro Leu Xaa Xaa Xaa Pro Met Pro
1               5                   10                  15

Phe

<210> SEQ ID NO 120
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (11)..(11)
<223> OTHER INFORMATION: Xaa at position 11 is Ser or His
<220> FEATURE:
<221> NAME/KEY: MISC_FEATURE
<222> LOCATION: (12)..(12)
<223> OTHER INFORMATION: Xaa at position 12 is Ser or His
<220> FEATURE:
<221> NAME/KEY: MISC_FEATURE
<222> LOCATION: (13)..(13)
<223> OTHER INFORMATION: Xaa at position 13 is Arg or Lys
<220> FEATURE:
<221> NAME/KEY: MISC_FEATURE
<222> LOCATION: (14)..(14)
<223> OTHER INFORMATION: Xaa at position 14 is Val or Gly

<400> SEQUENCE: 120

Asn Cys Leu Gln Arg Arg Cys Met Pro Leu Xaa Xaa Xaa Xaa Pro Met
1               5                   10                  15

Pro Phe
```

```
<210> SEQ ID NO 121
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: Xaa at position 6 is Ser or His
<220> FEATURE:
<221> NAME/KEY: MISC_FEATURE
<222> LOCATION: (7)..(7)
<223> OTHER INFORMATION: Xaa at position 7 is Ser or His
<220> FEATURE:
<221> NAME/KEY: MISC_FEATURE
<222> LOCATION: (8)..(8)
<223> OTHER INFORMATION: Xaa at position 8 is Arg or Lys
<220> FEATURE:
<221> NAME/KEY: MISC_FEATURE
<222> LOCATION: (9)..(9)
<223> OTHER INFORMATION: Xaa at position 9 is Val or Gly

<400> SEQUENCE: 121

Gln Arg Arg Cys Leu Xaa Xaa Xaa Xaa Pro Met Pro Phe
1               5                   10

<210> SEQ ID NO 122
<211> LENGTH: 5
<212> TYPE: PRT
<213> ORGANISM: Artificial Sequence
<220> FEATURE:
<223> OTHER INFORMATION: synthetic construct

<400> SEQUENCE: 122

Gly Gly Gly Gly Ser
1               5

<210> SEQ ID NO 123
<211> LENGTH: 10
<212> TYPE: PRT
<213> ORGANISM: Artificial Sequence
<220> FEATURE:
<223> OTHER INFORMATION: Synthetic construct

<400> SEQUENCE: 123

Gly Gly Gly Gly Ser Gly Gly Gly Gly Ser
1               5                   10

<210> SEQ ID NO 124
<211> LENGTH: 15
<212> TYPE: PRT
<213> ORGANISM: Artificial Sequence
<220> FEATURE:
<223> OTHER INFORMATION: Synthetic construct

<400> SEQUENCE: 124

Gly Gly Gly Gly Ser Gly Gly Gly Gly Ser Gly Gly Gly Gly Ser
1               5                   10                  15

<210> SEQ ID NO 125
<211> LENGTH: 32
<212> TYPE: PRT
<213> ORGANISM: Artificial Sequence
<220> FEATURE:
<223> OTHER INFORMATION: Synthetic construct

<400> SEQUENCE: 125

Pro Phe Pro Val Arg Ser His Leu Pro Met Cys Arg Arg Gln Leu Cys
```

```
1               5                   10                  15
Asn His Lys Arg Leu Lys Arg Arg Met Thr Leu Asn Val Pro Arg Gln
            20                  25                  30

<210> SEQ ID NO 126
<211> LENGTH: 21
<212> TYPE: PRT
<213> ORGANISM: Artificial Sequence
<220> FEATURE:
<223> OTHER INFORMATION: Synthetic construct

<400> SEQUENCE: 126

Pro Phe Pro Val Arg Ser His Leu Pro Met Cys Arg Arg Gln Leu Cys
1               5                   10                  15

Asn His Lys Arg Leu
            20

<210> SEQ ID NO 127
<211> LENGTH: 11
<212> TYPE: PRT
<213> ORGANISM: Artificial Sequence
<220> FEATURE:
<223> OTHER INFORMATION: Synthetic construct

<400> SEQUENCE: 127

Pro Phe Pro Val Arg Ser His Leu Pro Met Cys
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Synthetic construct

<400> SEQUENCE: 128

Pro Ala Pro Val Arg Ser His Leu Pro Met Cys Arg Arg Gln
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Synthetic construct

<400> SEQUENCE: 129

Pro Phe Pro Val Arg Lys His Ser Leu Arg Pro Arg Gln
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Synthetic construct

<400> SEQUENCE: 130

Pro Ala Pro Val Arg Lys His Ser Leu Arg Pro Arg Gln
1               5                   10

<210> SEQ ID NO 131
<211> LENGTH: 14
<212> TYPE: PRT
<213> ORGANISM: Artificial Sequence
<220> FEATURE:
```

<223> OTHER INFORMATION: Synthetic construct

<400> SEQUENCE: 131

Phe Pro Met Pro Gly Ser His Leu Pro Met Cys Arg Arg Gln
1               5                   10

<210> SEQ ID NO 132
<211> LENGTH: 17
<212> TYPE: PRT
<213> ORGANISM: Artificial Sequence
<220> FEATURE:
<223> OTHER INFORMATION: Synthetic construct

<400> SEQUENCE: 132

Phe Pro Met Pro Gly Ser His Leu Pro Met Cys Arg Arg Gln Leu Cys
1               5                   10                  15

Asn

<210> SEQ ID NO 133
<211> LENGTH: 13
<212> TYPE: PRT
<213> ORGANISM: Artificial Sequence
<220> FEATURE:
<223> OTHER INFORMATION: Synthetic construct

<400> SEQUENCE: 133

Pro Phe Pro Val Gly Lys His Ser Leu Arg Pro Arg Gln
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Synthetic construct

<400> SEQUENCE: 134

Pro Ala Pro Val Gly Lys His Ser Leu Arg Pro Arg Gln
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Synthetic construct

<400> SEQUENCE: 135

Phe Pro Met Pro Arg Ser His Leu Pro Met Cys Arg Arg Gln
1               5                   10

<210> SEQ ID NO 136
<211> LENGTH: 17
<212> TYPE: PRT
<213> ORGANISM: Artificial Sequence
<220> FEATURE:
<223> OTHER INFORMATION: Synthetic construct

<400> SEQUENCE: 136

Phe Pro Met Pro Arg Ser His Leu Pro Met Cys Arg Arg Gln Leu Cys
1               5                   10                  15

Asn

<210> SEQ ID NO 137
<211> LENGTH: 12

```
<212> TYPE: PRT
<213> ORGANISM: Artificial Sequence
<220> FEATURE:
<223> OTHER INFORMATION: Synthetic construct

<400> SEQUENCE: 137

Pro Phe Pro Val Arg Ser His Leu Arg Pro Arg Gln
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic construct

<400> SEQUENCE: 138

Pro Ala Pro Val Arg Ser His Leu Arg Pro Arg Gln
1               5                   10

<210> SEQ ID NO 139
<211> LENGTH: 15
<212> TYPE: PRT
<213> ORGANISM: Artificial Sequence
<220> FEATURE:
<223> OTHER INFORMATION: Synthetic construct

<400> SEQUENCE: 139

Phe Pro Met Pro Gly Lys His Ser Leu Pro Met Cys Arg Arg Gln
1               5                   10                  15

<210> SEQ ID NO 140
<211> LENGTH: 18
<212> TYPE: PRT
<213> ORGANISM: Artificial Sequence
<220> FEATURE:
<223> OTHER INFORMATION: Synthetic construct

<400> SEQUENCE: 140

Phe Pro Met Pro Gly Lys His Ser Leu Pro Met Cys Arg Arg Gln Leu
1               5                   10                  15

Cys Asn

<210> SEQ ID NO 141
<211> LENGTH: 12
<212> TYPE: PRT
<213> ORGANISM: Artificial Sequence
<220> FEATURE:
<223> OTHER INFORMATION: Synthetic construct

<400> SEQUENCE: 141

Pro Phe Pro Gly Lys His Ser Leu Arg Pro Arg Gln
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic construct

<400> SEQUENCE: 142

Pro Ala Pro Gly Lys His Ser Leu Arg Pro Arg Gln
1               5                   10

<210> SEQ ID NO 143
```

```
<211> LENGTH: 15
<212> TYPE: PRT
<213> ORGANISM: Artificial Sequence
<220> FEATURE:
<223> OTHER INFORMATION: Synthetic construct

<400> SEQUENCE: 143

Phe Pro Met Pro Val Arg Ser His Leu Pro Met Cys Arg Arg Gln
1               5                   10                  15

<210> SEQ ID NO 144
<211> LENGTH: 18
<212> TYPE: PRT
<213> ORGANISM: Artificial Sequence
<220> FEATURE:
<223> OTHER INFORMATION: Synthetic construct

<400> SEQUENCE: 144

Phe Pro Met Pro Val Arg Ser His Leu Pro Met Cys Arg Arg Gln Leu
1               5                   10                  15

Cys Asn

<210> SEQ ID NO 145
<211> LENGTH: 12
<212> TYPE: PRT
<213> ORGANISM: Artificial Sequence
<220> FEATURE:
<223> OTHER INFORMATION: Synthetic construct

<400> SEQUENCE: 145

Pro Phe Pro Val Arg His Ser Leu Arg Pro Arg Gln
1               5                   10

<210> SEQ ID NO 146
<211> LENGTH: 12
<212> TYPE: PRT
<213> ORGANISM: Artificial Sequence
<220> FEATURE:
<223> OTHER INFORMATION: Synthetic construct

<400> SEQUENCE: 146

Pro Ala Pro Val Arg His Ser Leu Arg Pro Arg Gln
1               5                   10

<210> SEQ ID NO 147
<211> LENGTH: 15
<212> TYPE: PRT
<213> ORGANISM: Artificial Sequence
<220> FEATURE:
<223> OTHER INFORMATION: Synthetic construct

<400> SEQUENCE: 147

Phe Pro Met Pro Gly Lys Ser His Leu Pro Met Cys Arg Arg Gln
1               5                   10                  15

<210> SEQ ID NO 148
<211> LENGTH: 18
<212> TYPE: PRT
<213> ORGANISM: Artificial Sequence
<220> FEATURE:
<223> OTHER INFORMATION: Synthetic construct

<400> SEQUENCE: 148

Phe Pro Met Pro Gly Lys Ser His Leu Pro Met Cys Arg Arg Gln Leu
1               5                   10                  15

Cys Asn
```

<210> SEQ ID NO 149
<211> LENGTH: 15
<212> TYPE: PRT
<213> ORGANISM: Artificial Sequence
<220> FEATURE:
<223> OTHER INFORMATION: Synthetic construct

<400> SEQUENCE: 149

Pro Phe Pro Gly Lys His Ser Leu Cys Arg Arg Gln Leu Cys Asn
1               5                   10                  15

<210> SEQ ID NO 150
<211> LENGTH: 13
<212> TYPE: PRT
<213> ORGANISM: Artificial Sequence
<220> FEATURE:
<223> OTHER INFORMATION: Synthetic construct

<400> SEQUENCE: 150

Phe Pro Met Pro Gly Lys His Ser Leu Cys Arg Arg Gln
1               5                   10

<210> SEQ ID NO 151
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is Phe or Ala
<220> FEATURE:
<221> NAME/KEY: MISC_FEATURE
<222> LOCATION: (5)..(5)
<223> OTHER INFORMATION: Xaa at position 5 is Arg or Gly
<220> FEATURE:
<221> NAME/KEY: MISC_FEATURE
<222> LOCATION: (7)..(7)
<223> OTHER INFORMATION: Xaa at position 7 is Ser or His
<220> FEATURE:
<221> NAME/KEY: MISC_FEATURE
<222> LOCATION: (8)..(8)
<223> OTHER INFORMATION: Xaa at position 8 is Ser or His

<400> SEQUENCE: 151

Pro Xaa Pro Val Xaa Lys Xaa Xaa Leu Arg Pro Arg Gln
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is Phe or Ala
<220> FEATURE:
<221> NAME/KEY: MISC_FEATURE
<222> LOCATION: (4)..(4)
<223> OTHER INFORMATION: Xaa at position 4 is Val or Gly
<220> FEATURE:
<221> NAME/KEY: MISC_FEATURE
<222> LOCATION: (5)..(5)
<223> OTHER INFORMATION: Xaa at position 5 is Arg or Lys
<220> FEATURE:
<221> NAME/KEY: MISC_FEATURE
<222> LOCATION: (6)..(6)
<223> OTHER INFORMATION: Xaa at position 6 is Ser or His

```
<220> FEATURE:
<221> NAME/KEY: MISC_FEATURE
<222> LOCATION: (7)..(7)
<223> OTHER INFORMATION: Xaa at position 7 is Ser or His

<400> SEQUENCE: 152

Pro Xaa Pro Xaa Xaa Xaa Xaa Leu Arg Pro Arg Gln
1               5                   10

<210> SEQ ID NO 153
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa at position 5 is Arg or Gly
<220> FEATURE:
<221> NAME/KEY: MISC_FEATURE
<222> LOCATION: (6)..(6)
<223> OTHER INFORMATION: Xaa at position 6 is Ser or His
<220> FEATURE:
<221> NAME/KEY: MISC_FEATURE
<222> LOCATION: (7)..(7)
<223> OTHER INFORMATION: Xaa at position 7 is Ser or His

<400> SEQUENCE: 153

Phe Pro Met Pro Xaa Xaa Xaa Leu Pro Met Cys Arg Arg Gln Leu Cys
1               5                   10                  15

Asn

<210> SEQ ID NO 154
<211> LENGTH: 18
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa at position 5 is Val or Gly
<220> FEATURE:
<221> NAME/KEY: MISC_FEATURE
<222> LOCATION: (6)..(6)
<223> OTHER INFORMATION: Xaa at position 6 is Arg or Lys
<220> FEATURE:
<221> NAME/KEY: MISC_FEATURE
<222> LOCATION: (7)..(7)
<223> OTHER INFORMATION: Xaa at position 7 is Ser or His
<220> FEATURE:
<221> NAME/KEY: MISC_FEATURE
<222> LOCATION: (8)..(8)
<223> OTHER INFORMATION: Xaa at position 8 is Ser or His

<400> SEQUENCE: 154

Phe Pro Met Pro Xaa Xaa Xaa Xaa Leu Pro Met Cys Arg Arg Gln Leu
1               5                   10                  15

Cys Asn

<210> SEQ ID NO 155
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa at position 5 is Val or Gly
```

```
<220> FEATURE:
<221> NAME/KEY: MISC_FEATURE
<222> LOCATION: (6)..(6)
<223> OTHER INFORMATION: Xaa at position 6 is Arg or Lys
<220> FEATURE:
<221> NAME/KEY: MISC_FEATURE
<222> LOCATION: (7)..(7)
<223> OTHER INFORMATION: Xaa at position 7 is Ser or His
<220> FEATURE:
<221> NAME/KEY: MISC_FEATURE
<222> LOCATION: (8)..(8)
<223> OTHER INFORMATION: Xaa at position 8 is Ser or His

<400> SEQUENCE: 155

Phe Pro Met Pro Xaa Xaa Xaa Xaa Leu Cys Arg Arg Gln
1               5                   10

<210> SEQ ID NO 156
<211> LENGTH: 468
<212> TYPE: PRT
<213> ORGANISM: Homo sapiens

<400> SEQUENCE: 156

Glu Ile Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Ile Tyr Leu Pro Asp Ser Leu Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Thr
                85                  90                  95

Arg Gly Arg Gly Asn Ser Ser Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285
```

```
Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Gly Gly Gly
            435                 440                 445

Gly Ser Gly Gly Gly Ser Gln Arg Pro Arg Leu Ser His Lys Gly
        450                 455                 460

Pro Met Pro Phe
465

<210> SEQ ID NO 157
<211> LENGTH: 446
<212> TYPE: PRT
<213> ORGANISM: Homo sapiens

<400> SEQUENCE: 157

Glu Ile Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Ile Tyr Leu Pro Asp Ser Leu Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Thr
                85                  90                  95

Arg Gly Arg Gly Asn Ser Ser Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180                 185                 190
Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 158
<211> LENGTH: 219
<212> TYPE: PRT
<213> ORGANISM: Homo sapiens

<400> SEQUENCE: 158

Asp Val Leu Met Thr Gln Ser Pro Leu Ser Leu Pro Val Thr Leu Gly
1               5                   10                  15

Gln Pro Ala Ser Ile Ser Cys Arg Ser Asp Gln Ser Leu Val His Arg
            20                  25                  30

Thr Gly Asn Thr His Leu Asp Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Ile Pro Phe Thr Phe Gly Gln Gly Thr Lys Val Glu Ile Lys
            100                 105                 110
```

```
Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 159
<211> LENGTH: 476
<212> TYPE: PRT
<213> ORGANISM: Homo sapiens

<400> SEQUENCE: 159

Glu Ile Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Ile Tyr Leu Pro Asp Ser Leu Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Thr
            85                  90                  95

Arg Gly Arg Gly Asn Ser Ser Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

-continued

```
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Gln Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
                420                 425                 430
Asn His Tyr Thr Gln Lys Ser Leu Ser Leu Ser Leu Gly Gly Gly Gly
            435                 440                 445
Gly Ser Gly Gly Gly Ser Leu Arg Lys His Asn Cys Leu Gln Arg
450                 455                 460
Arg Cys Met Pro Leu His Ser Arg Val Pro Phe Pro
465                 470                 475

<210> SEQ ID NO 160
<211> LENGTH: 466
<212> TYPE: PRT
<213> ORGANISM: Homo sapiens

<400> SEQUENCE: 160

Glu Ile Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ala Ser Ile Ser Ser Gly Gly Ser Ile Tyr Leu Pro Asp Ser Leu Lys
    50                  55                  60
Gly Arg Phe Thr Ile Ser Arg Asp Asn Ala Lys Asn Ser Leu Tyr Leu
65                  70                  75                  80
Gln Met Asn Ser Leu Arg Ala Glu Asp Thr Ala Val Tyr Tyr Cys Thr
                85                  90                  95
Arg Gly Arg Gly Asn Ser Ser Ala Trp Phe Ala Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
```

```
                165                 170                 175
Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Gly Gly Gly
        435                 440                 445

Gly Ser Gly Gly Gly Ser Cys Met Pro Leu His Ser Arg Val Pro
    450                 455                 460

Phe Pro
465

<210> SEQ ID NO 161
<211> LENGTH: 467
<212> TYPE: PRT
<213> ORGANISM: Homo sapiens

<400> SEQUENCE: 161

Glu Ile Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Ile Tyr Leu Pro Asp Ser Leu Lys
    50                  55                  60
```

-continued

```
Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Thr
                 85                  90                  95

Arg Gly Arg Gly Asn Ser Ser Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Gly Gly Gly
        435                 440                 445

Gly Ser Gly Gly Gly Gly Ser Gln Arg Pro Arg Leu His Ser Arg Val
    450                 455                 460

Pro Phe Pro
465
```

```
<210> SEQ ID NO 162
<211> LENGTH: 467
<212> TYPE: PRT
<213> ORGANISM: Homo sapiens

<400> SEQUENCE: 162

Glu Ile Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Ile Tyr Leu Pro Asp Ser Leu Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Thr
                85                  90                  95

Arg Gly Arg Gly Asn Ser Ser Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380
```

Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Gly Gly
            435                 440                 445

Gly Ser Gly Gly Gly Ser Gln Arg Pro Arg Leu Ser His Lys Gly
            450                 455                 460

Pro Phe Pro
465

<210> SEQ ID NO 163
<211> LENGTH: 470
<212> TYPE: PRT
<213> ORGANISM: Homo sapiens

<400> SEQUENCE: 163

Glu Ile Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Ile Tyr Leu Pro Asp Ser Leu Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Thr
                85                  90                  95

Arg Gly Arg Gly Asn Ser Ser Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

```
Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Gly Gly Gly
                435                 440                 445

Gly Ser Gly Gly Gly Gly Ser Gln Arg Arg Ser Met Pro Leu His Ser
450                 455                 460

Arg Val Pro Met Pro Phe
465                 470

<210> SEQ ID NO 164
<211> LENGTH: 468
<212> TYPE: PRT
<213> ORGANISM: Homo sapiens

<400> SEQUENCE: 164

Glu Ile Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Ile Tyr Leu Pro Asp Ser Leu Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Thr
                85                  90                  95

Arg Gly Arg Gly Asn Ser Ser Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
                180                 185                 190
Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Gly Gly Gly
        435                 440                 445

Gly Ser Gly Gly Gly Ser Gln Arg Arg Cys Leu Ser His Lys Gly
    450                 455                 460

Pro Met Pro Phe
465

<210> SEQ ID NO 165
<211> LENGTH: 470
<212> TYPE: PRT
<213> ORGANISM: Homo sapiens

<400> SEQUENCE: 165

Glu Ile Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Ser Ile Tyr Leu Pro Asp Ser Leu Lys
    50                  55                  60

Gly Arg Phe Thr Ile Ser Arg Asp Asn Ala Lys Asn Ser Leu Tyr Leu
65                  70                  75                  80
```

```
Gln Met Asn Ser Leu Arg Ala Glu Asp Thr Ala Val Tyr Tyr Cys Thr
            85                  90                  95
Arg Gly Arg Gly Asn Ser Ser Ala Trp Phe Ala Tyr Trp Gly Gln Gly
            100                 105                 110
Thr Leu Val Thr Val Ser Ser Ala Ser Thr Lys Gly Pro Ser Val Phe
            115                 120                 125
Pro Leu Ala Pro Cys Ser Arg Ser Thr Ser Glu Ser Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Lys Thr Tyr Thr Cys Asn Val Asp His Lys Pro
                195                 200                 205
Ser Asn Thr Lys Val Asp Lys Arg Val Glu Ser Lys Tyr Gly Pro Pro
            210                 215                 220
Cys Pro Pro Cys Pro Ala Pro Glu Ala Ala Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
                260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Gln Glu Glu Met Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Gly Gly Gly
            435                 440                 445
Gly Ser Gly Gly Gly Gly Ser Asn Cys Leu Gln Arg Arg Cys Leu Ser
450                 455                 460
His Lys Gly Pro Phe Pro
465                 470

<210> SEQ ID NO 166
<211> LENGTH: 13
<212> TYPE: PRT
```

<213> ORGANISM: Artificial Sequence
<220> FEATURE:
<223> OTHER INFORMATION: Synthetic construct

<400> SEQUENCE: 166

Gln Arg Pro Arg Leu Ser His Lys Gly Pro Met Pro Phe
1               5                   10

<210> SEQ ID NO 167
<211> LENGTH: 15
<212> TYPE: PRT
<213> ORGANISM: Artificial Sequence
<220> FEATURE:
<223> OTHER INFORMATION: Synthetic construct

<400> SEQUENCE: 167

Gln Arg Arg Ser Met Pro Leu His Ser Arg Val Pro Met Pro Phe
1               5                   10                  15

<210> SEQ ID NO 168
<211> LENGTH: 20
<212> TYPE: DNA
<213> ORGANISM: Artificial Sequence
<220> FEATURE:
<223> OTHER INFORMATION: Synthetic construct

<400> SEQUENCE: 168
tttggrggga agatgaagac                                                  20

<210> SEQ ID NO 169
<211> LENGTH: 21
<212> TYPE: DNA
<213> ORGANISM: Artificial Sequence
<220> FEATURE:
<223> OTHER INFORMATION: Synthetic construct

<400> SEQUENCE: 169
ttaacactct cccctgttga a                                                21

<210> SEQ ID NO 170
<211> LENGTH: 21
<212> TYPE: DNA
<213> ORGANISM: Artificial Sequence
<220> FEATURE:
<223> OTHER INFORMATION: Synthetic construct

<400> SEQUENCE: 170
ttaacactca ttcctgttga a                                                21

<210> SEQ ID NO 171
<211> LENGTH: 21
<212> TYPE: DNA
<213> ORGANISM: Artificial Sequence
<220> FEATURE:
<223> OTHER INFORMATION: Synthetic construct

<400> SEQUENCE: 171
tggacaggga tccagagttc c                                                21

<210> SEQ ID NO 172
<211> LENGTH: 21
<212> TYPE: DNA
<213> ORGANISM: Artificial Sequence
<220> FEATURE:
<223> OTHER INFORMATION: Synthetic construct

<400> SEQUENCE: 172

```
tggacagggc tccatagttc c                                              21

<210> SEQ ID NO 173
<211> LENGTH: 20
<212> TYPE: DNA
<213> ORGANISM: Artificial Sequence
<220> FEATURE:
<223> OTHER INFORMATION: Synthetic construct

<400> SEQUENCE: 173
actcgtcctt ggtcaacgtg                                                20
```

APJ ANTIBODY, FUSION PROTEIN THEREOF WITH ELABELA, AND PHARMACEUTICAL COMPOSITIONS AND USE THEREOFUS01

CROSS-REFERENCE TO RELATED APPLICATIONS

This application is a U.S. national stage of International Patent Application No. PCT/CN2019/091090, filed Jun. 13, 2019, which claims the priority to Chinese Patent Application No. 201810606914.0, filed Jun. 13, 2018, the disclosure of each of which is incorporated by reference herein in its entirety.

SEQUENCE LISTING

This application incorporates by reference in its entirety the Computer Readable Form of a Sequence Listing in ASCII text format submitted via EFS-Web. The Sequence Listing text file submitted via EFS-Web entitled "087222-8002US01-SL_ST25", was created on Jul. 29, 2024 and is 120,072 bytes in size.

FIELD

Provided herein are an apelin receptor (APJ) antibody and its fusion protein with Elabela. Also provided herein is a pharmaceutical composition of a fusion protein with APJ antibody and Elabela, and use thereof in treating, preventing, or alleviating one or more symptoms of pulmonary arterial hypertension, pulmonary hypertension or one or more symptoms of heart failure.

BACKGROUND

APJ contains 7 transmembrane units and 308 amino acids and belongs to the family of G protein coupled receptors (GPCRs). The vasoactive peptide Apelin is the earliest discovered endogenous ligand of the APJ receptor. Apelin and APJ are widely distributed in the human central nervous system and various peripheral tissues such as the lung, heart, breast, etc (Kawamata et al., 2001, *Biochem. Biophys. Acta.* 1538: 162-71; Medhurst et al., 2003, *J. Neurochem.* 84: 1162-72), especially in cardiovascular endothelial cells and cardiac tissue (Kleiz et al., 2005, *Regul. Pept.* 126: 233-40). A number of studies have shown that the Apelin/APJ signaling system can enhance myocardial contractility, lower blood pressure, promote neovascularization, regulate the immune response and release of pituitary related hormones, regulate insulin secretion, etc, and participate in the pathophysiological events of diabetic vascular disease, cardiac insufficiency, atrial fibrillation and ischemia-reperfusion injury.

Elabela is another endogenous ligand of the APJ receptor that has been discovered in recent years and has attracted great attention (Chng et al., 2013, *Dev. Cell* 27: 672-680; Pauli et al., 2014, *Science* 343: 1248636). Elabela is encoded by three exons on human chromosome 4 and was previously considered to be non-coding RNA. However, studies have found that Elabela contains a conservative ORF that encodes a protein of 54 amino acids, with its mature body consisting of only 32 amino acids. The Elabela/APJ signaling pathway has been shown to play a critical role in the development of the embryo's heart and vasculature. Studies have confirmed that Elabela and Elabela mutants can activate the Gail and β-arrestin2 signal transduction pathways of APJ receptors. Further, mutations in the C-terminus of Elabela polypeptides can trigger a preference for APJ receptor signal transduction pathways (Murza et al., 2016, *J Med. Chem.* 59: 2962-72). The preference of receptor signal transduction pathways provides an important direction for new drug development (Bologna et al., 2017, *Biomol. Ther.* 25: 12-25). By using the separated perfusion heart and in vivo hemodynamics and echocardiography measurements, it was found that Elabela or Elabela mutants can reduce arterial pressure and exert positive inotropic effects on the heart (Yang et al., 2017, *Circulation* 135: 1160-1173; Murza et al., 2016, *J. Med. Chem.* 59: 2962-72). Other studies also found that Elabela content in patients with diabetic nephropathy is negatively correlated with urine microalbumin creatinine ratio (ACR) (Zhang et al., 2018, *Cell Physiol Biochem.* 48: 1347-1354).

The fusion of Elabela and APJ antibody can significantly prolong the half-life of Elabela to retain the biological activity of Elabela molecules. At the same time, the fusion protein of APJ antibody and Elabela has the molecular targeting provided by the antibody, and it helps to improve the druggability of Elabela fusion protein to play a role in the treatment of one or more diseases of pulmonary arterial hypertension (PAH), pulmonary hypertension (PH), type 2 diabetes (T2D) and its related metabolic syndrome, and heart failure.

SUMMARY

Provided herein is an antibody specifically binding to APJ.

Provided herein is an antibody specifically binding to APJ, wherein the antibody comprises 1, 2, 3, 4, 5, or 6 amino acid sequences, wherein each amino acid sequence is independently selected from the amino acid sequences listed below:
  a. light chain CDR1 amino acid sequences: SEQ ID NO: 1, SEQ ID NO: 4, SEQ ID NO: 7, and SEQ ID NO: 10;
  b. light chain CDR2 amino acid sequences: SEQ ID NO: 2, SEQ ID NO: 5, and SEQ ID NO: 8;
  c. light chain CDR3 amino acid sequences: SEQ ID NO: 3, SEQ ID NO: 6, SEQ ID NO: 9, and SEQ ID NO: 11;
  d. heavy chain CDR1 amino acid sequences: SEQ ID NO: 12, SEQ ID NO: 15, and SEQ ID NO: 18;
  e. heavy chain CDR2 amino acid sequences: SEQ ID NO: 13, SEQ ID NO: 16, SEQ ID NO: 19, and SEQ ID NO: 21; and
  f. heavy chain CDR3 amino acid sequences: SEQ ID NO: 14, SEQ ID NO: 17, SEQ ID NO: 20, and SEQ ID NO: 22.

Provided herein is an Elabela fusion protein, comprising an antibody specifically binding to APJ, and 1, 2, 3, 4, 5, 6, 7 or 8 Elabela fragment peptide linker sequences (Linker); the fusion protein, through a peptide linker sequence (Linker), connects the N-terminus of an Elabela fragment with the C-terminus of a heavy or light chain of APJ antibody, wherein each Elabela fragment is independently a forward Elabela fragment or its mutant; or the fusion protein, through a peptide linker sequence (Linker), connects the C-terminus of an Elabela fragment with the N-terminus of a heavy or light chain of APJ antibody, wherein each Elabela fragment is independently a reverse Elabela fragment or its mutant.

Provided herein is an Elabela fusion protein, comprising an APJ antibody and two Elabela fragments and two peptide linker sequences (Linker); the fusion protein, through a peptide linker sequence (Linker), connects the N-terminus of an Elabela fragment with the C-terminus of a light chain of APJ antibody: N'—R-Linker-Elabela-C'; or through a peptide linker sequence (Linker), connects the N-terminus of an Elabela fragment with the C-terminus of a heavy chain of APJ antibody: N'—R-Linker-Elabela-C'; wherein, N' represents the N-terminus of the fusion protein polypeptide, C' represents the C-terminus of the fusion protein polypeptide, Elabela represents the forward Elabela fragment or its mutant, R represents the amino acid sequence of the light or heavy chain of APJ antibody, and Linker represents the peptide linker sequence.

Provided herein is a polynucleotide encoding an Elabela fusion protein described herein.

Provided herein is a vector, comprising a polynucleotide encoding an Elabela fusion protein described herein.

Provided herein is a host cell line, comprising one vector described herein.

Provided herein is a pharmaceutical composition, comprising an APJ antibody or an Elabela fusion protein, and a pharmaceutically acceptable carrier described herein.

Provided herein is the use of an APJ antibody or an Elabela fusion protein described herein in the preparation of a medicament for treating, preventing or ameliorating PAH and PAH related diseases.

Provided herein is the use of an APJ antibody or an Elabela fusion protein described herein in the preparation of a medicament for treating, preventing or ameliorating PH and PH related diseases.

Provided herein is the use of an APJ antibody or an Elabela fusion protein described herein in the preparation of a medicament for treating, preventing or ameliorating heart failure and hear failure related diseases.

Provided herein is the use of an APJ antibody or an Elabela fusion protein described herein in the preparation of a medicament for treating, preventing or ameliorating type 2 diabetes and related metabolic syndrome.

Provided herein is the use of an APJ antibody or an Elabela fusion protein described herein in the preparation of a medicament for simultaneously treating, preventing or ameliorating two and more than two diseases of PAH, PH, type 2 diabetes and related metabolic syndrome or heart failure.

Provided herein is a method to treat, prevent, or improve one or more symptoms of PAH, comprising giving subjects a therapeutically effective dose of an APJ antibody or an Elabela fusion protein described herein.

Provided herein is a method to treat, prevent, or improve one or more symptoms of PH, comprising giving subjects a therapeutically effective dose of an APJ antibody or an Elabela fusion protein described herein.

Provided herein is a method to treat, prevent, or improve one or more symptoms of heart failure, comprising giving subjects a therapeutically effective dose of an APJ antibody or an Elabela fusion protein described herein.

Provided herein is a method to treat, prevent, or improve one or more symptoms of type 2 diabetes and related metabolic syndrome, comprising giving subjects a therapeutically effective dose of an APJ antibody or an Elabela fusion protein described herein.

DETAILED DESCRIPTION

Definitions

Figure 1A:
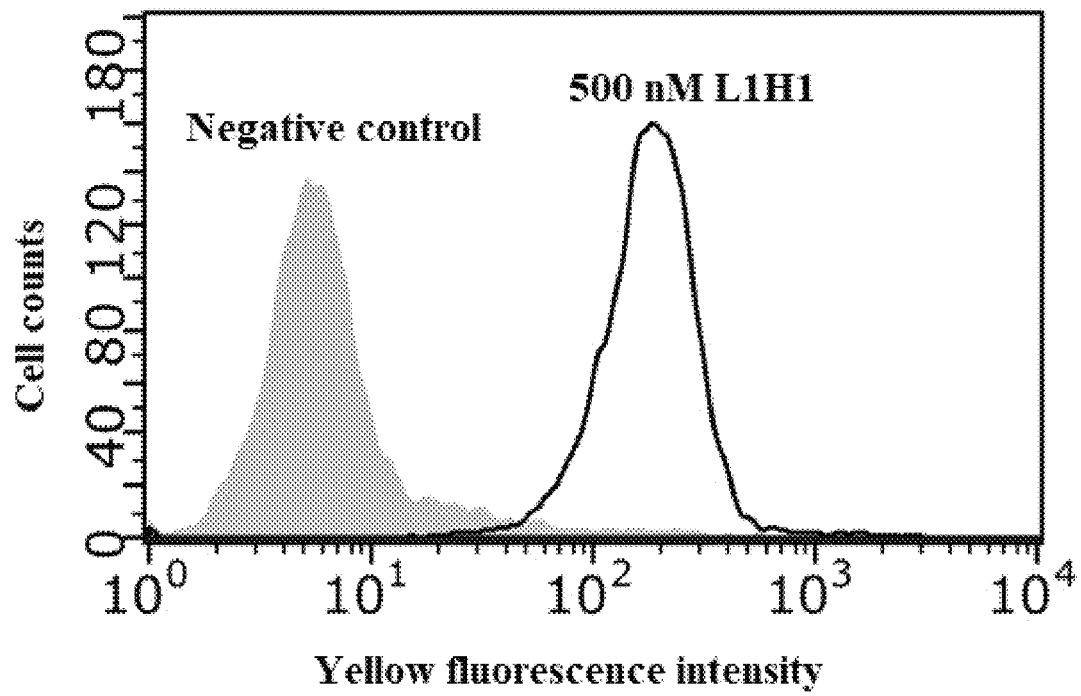
FIGS. 1A, 1B, 1C and 1D show the results of FACS test of the specific binding of recombinant hAPJ antibodies L1H1 (comprising SEQ ID NO: 59 and SEQ ID NO: 64) and L4H4 (comprising SEQ ID NO: 62 and SEQ ID NO: 67) to hAPJ (at antibody concentration of 500 nM or 4 nM). The gray peaks are negative controls, representing the binding curves of L1H1 or L4H4 to CHO-DHFR—. The solid line peaks represent the binding curves of L1H1 (FIGS. 1A and 1B) or L4H4 (FIGS. 1C and 1D) to CHO-DHFR-hAPJ.

Unless defined otherwise herein, scientific and technical terms described herein shall have the meanings understood by ordinary technicians in the field. Generally, nomenclatures and techniques related to pharmacology, biology, biochemistry, cell and tissue culture, molecular biology, immunology, microbiology, genetics and protein nucleic acid chemistry as well as hybridization are well-known and commonly used in the field.

Standard single-letter or three-letter abbreviations are used in this application to indicate polynucleotide and polypeptide sequences. When the polypeptide sequence is written, the first amino acid residue (N') with the amino group is at the far left and the last amino acid residue (C') with the carboxyl group is at the far right, for example, the Elabela fragment and its mutant sequence involved in this invention: SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, and SEQ ID NO: 121. Reverse polypeptide sequence refers to a polypeptide sequence wherein amino acids arranged in a reversed order as to the original, for example, the reverse Elabela fragment and its mutant sequences converted from the above Elabela fragment and its mutant sequences: SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO:

149, SEQ ID NO: 150, SEQ ID NO: 151, SEQ ID NO: 152, SEQ ID NO: 153, SEQ ID NO: 154, and SEQ ID NO: 155. The 5' ends of the upstream chains of single-stranded and double-stranded nucleic acid sequences are on the left and their 3' ends are on the right. The specific portion of a polypeptide can be represented by an amino acid residue number, such as amino acids 67 to 134, or represented by the actual residue of the site, such as Lys67 to Lys134. The specific polypeptide or polynucleotide sequence can also be described by explaining its difference from the reference sequence.

The term "individual" refers to animals, including but not limited to primates (e.g., human), cattle, pig, sheep, goat, horse, dog, cat, rabbit, rat, or mouse. The terms "individual" and "patient" are used interchangeably, for example, to refer to a mammalian individual, such as a human individual, and in one embodiment, referring to a human.

The meaning of the term "treatment" includes reducing or eliminating the disorder, disease or condition, or one or more symptoms associated with the disorder, disease or condition; or reducing or eliminating the focus of the disorder, disease or condition.

The meaning of the term "prevention" includes delaying and/or relieving the onset of the disorder, disease or condition and/or its accompanying symptoms; preventing the individual from acquiring the disorder, disease or condition; or reducing the risk of the individual acquiring the disorder, disease or condition.

The term "control" refers to preventing or slowing the progression, spread, or worsening of a disease, disorder or condition, or one or more symptoms (e.g., pain). Sometimes, individuals benefit from the beneficial effects of preventive or therapeutic agents that do not lead to the cure of the condition, disorder or disease. In one embodiment, the term "control" refers to preventing or slowing the progression, spread, or worsening of osteolytic pain.

The meaning of the terms "therapeutically effective amount" and "effective amount" refer to an amount of the compound or combination of compounds that when administered is sufficient to prevent the development of or alleviate one or more symptoms of the disorder, disease or condition. The term "therapeutically effective amount" or "effective amount" also refers to an amount of compound that is sufficient to cause biological or medical response in a biomolecule (e.g., protein, enzyme, RNA, or DNA), cell, tissue, system, animal or human, which are sought for by researchers, veterinarians, doctors, or clinicians.

The terms "pharmaceutically acceptable carrier," "pharmaceutically acceptable excipient," "physiologically acceptable carrier" or "physiologically acceptable excipient" refer to pharmaceutically acceptable materials, compositions or carriers, such as liquid or solid fillers, diluents, solvents or packaging materials. In one embodiment, each component of "pharmaceutically acceptable" is compatible with other components of the pharmaceutical formulation and is suitable for contact with human or animal tissues or organs without excessive toxicity, irritation, allergy reactions, immunogenicity or other problems or complications, which is equivalent to a reasonable benefit/risk ratio.

The term "about" or "approximately" refers to an acceptable error determined by those skilled in the field, which partially depends on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7% 6%, 5% 4%, 3%, 2%, 1%, 0.5%, or 0.05% of a given value or range.

The terms "peptide," "polypeptide," and "protein" refer to a molecule containing two or more amino acids that are interlinked by a peptide bond. These terms cover, for example, natural and artificial proteins and peptide analogues of protein sequences (such as mutant proteins, variants and fusion proteins) and proteins that are post-transcriptional or otherwise covalent or non-covalent modified. A peptide, polypeptide, or protein can be a monomer or a polymer.

The term "polypeptide fragment" refers to a polypeptide that has an amino terminus and/or a carboxyl terminus missing from the corresponding full-length protein. For example, the fragment length can be at least 5, 6, 7, 8, 9, 10, 11, 12, 13, 14, 15, 20, 50, 70, 80, 90, 100, 150 or 200 amino acids in length. The fragment length can be, for example, up to 1,000, 750, 500, 250, 200, 175, 150, 125, 100, 90, 80, 70, 60, 50, 40, 30, 20, 15, 14, 13, 12, 11, or 10 amino acids. The fragment may further contain one or more additional amino acids at one end or both, such as amino acid sequences from different natural proteins (e.g., Fc or leucine zipper domains) or artificial amino acid sequences (e.g., artificial joint sequences).

Polypeptides in this invention include polypeptides modified for any reason or by any means, for example, by: (1) decreasing proteolysis sensitivity, (2) decreasing oxidation sensitivity, (3) altering the affinity for forming protein complexes, (4) altering binding affinity, and (5) conferring or modifying other physicochemical or functional properties. Analogue contains a mutant protein of a polypeptide. For example, single or multiple amino acid substitutions (e.g., conservative amino acid substitutions) can be made in the naturally occurring sequence (e.g., outside the domain of the polypeptide that forms intramolecular contact). The "conservative amino acid substitution" is one that does not significantly change the structural characteristics of the parent sequence (e.g., the substitution of amino acids shall not destroy the helices present in the parent sequence or interfere with other secondary structural types necessary to give the parent sequence its properties or function).

A "mutant" of a polypeptide comprises an amino acid sequence containing the insertion, deletion, and/or replacement of one or more residues in an amino acid sequence relative to another polypeptide sequence. The variants in this invention included fusion proteins.

A "derivative" of a polypeptide is a chemically modified polypeptide, for example, by binding to other chemical components such as polyethylene glycol, albumin (such as human serum albumin), phosphorylation, and glycosylation.

Unless otherwise indicated, the term "antibody" includes antibodies with two full-length heavy chains and two full-length light chains, as well as their derivatives, variants, fragments, and mutated proteins, instances are listed below.

The term "antibody" is a protein that contains the antigen-binding portion and optionally the scaffold or framework portion that allows the antigen-binding portion to adopt a conformation that promotes the binding of the antibody to the antigen. Examples of antibodies include complete antibodies, antibody fragments (such as the antigen-binding portion of an antibody), antibody derivatives, and antibody analogues. For example, the antibody may contain alternative protein scaffolds or artificial scaffolds with transplanted CDRs or derivatives of CDRs. The scaffold includes, but not limited to an antibody-derived scaffold that is introduced, such as one that stabilizes the three-dimensional structure of the antibody, and such as a fully synthetic scaffold for biocompatible polymer. See for example, Korndorfer et al., 2003, *Proteins* 53:121-129; Roque et al., 2004, *Biotechnol. Prog.* 20:639-654. In addition, the antibody may be either a mock peptide antibody ("PAMs") or a scaffold containing mock antibodies, therein use of fibrin ligands as scaffolds.

Antibodies may have structures such as innate immunoglobulin. "Immunoglobulin" is a tetramer molecule. In natural immunoglobulin, each tetramer consists of two identical polypeptide chain pairs, each pair having a "light" chain (approx. 25 k Da) and a "heavy" chain (approx. 50-70 kDa). The amino terminus of each chain includes a variable domain of about 100 to 110 amino acids, which is mainly related to antigen recognition. The carboxyl terminus of each chain determines the constant region mainly associated with the effect of the effectors. The human antibody light chain is divided into κ and λ light chains. The heavy chains were divided into μ, δ, α, or ε, and determined the same type of antigen, such as IgM, IgD, IgG, IgA, and IgE. In light and heavy chains, the variable and constant regions are connected by the "J" region of about 12 or more amino acids, and the heavy chain also includes the "D" region of about 10 more amino acids. Refer to Fundamental Immunology ch. 7 (edited by Paul, $2^{nd}$ edition, Raven Press, 1989). Variable regions of each light/heavy chain pair form antibody binding sites, in this way a complete immunoglobulin has two binding sites.

The innate immunoglobulin chains exhibit the same basic structure of a relatively conservative skeletal region (FR) connected by three highly variable regions, also known as the complementary decision region or CDRs. From the N end to the C end, the light and heavy chains contain the structural domains FR1, CDR1, FR2, CDR2, FR3, CDR3, and FR4. The distribution of amino acids in all structural domains was consistent with Kabat et al. in Sequences of Proteins of Immunological Interest, $5^{th}$ edition, U.S. Dept. Of Health and Human Services, PHS, NIH, NIH Publication No. 91-3242, 1991.

Unless otherwise specified, "antibody" means either the intact immunoglobulin or the antigen-binding portion of that can compete specifically binding to intact antibody. Antigen-binding portion can be produced by recombinant DNA techniques, and enzymatic or chemical cleavage of intact antibodies. Antigen-binding portion includes, in particular, Fab, Fab', F(ab)$_2$, Fv, structural domain antibodies (dAbs) contain complementary decision area (CDRs), single-chain antibody (scFv), chimeric antibody, double chains antibody (diabodies), three chains antibodies (triabodies), four chains (tetrabodies) and a polypeptide that contains at least a portion of the immunoglobulin that binds to a polypeptide-specific antigen.

The Fab fragment is a univalent fragment with $V_L$, $V_H$, $C_L$, and $C_H1$ domains; The F(ab')$_2$ fragment is a divalent fragment have two Fab fragments connected by a disulfide bond in the hinge region; Fv fragments have $V_H$ and $V_L$ domains; dAb fragments have $V_H$ domain, $V_L$ domain, or antigen binding fragments of $V_H$ or $V_L$ domain (U.S. Pat. Nos. 6,846,634 and 6,696,245; US patent application public numbers US 2005/0202512, US 2004/0202995, US 2004/0038291, US 2004/0009507, and US 2003/0039958; Ward et al., 1989, *Nature* 341:544-546).

Single-chain antibody (scFv) is a fusion protein in which the $V_L$ and $V_H$ regions are joined by a connector (for example, a synthetic sequence of amino acid residues) to form a continuous protein antibody, therein the connector is long enough to allow the protein chain to fold back to itself and to form a univalent antigen binding site (See, for example, Bird et al., 1988, *Science* 242:423-26; and Huston et al., 1988, *Proc. Natl. Acad. Sci. U.S.A.* 85:5879-83).

A double-chain antibody is a divalent antibody contain two polypeptide chains, each of which contains the $V_H$ and $V_L$ regions connected by a joint that is so short that it does not allow pairing of the two domains on the same chain. Therefore, each domain is allowed to pair with a complementary domain on another polypeptide chain (See, for example, Holliger et al., 1993, *Proc. Natl. Acad. Sci. U.S.A.* 90:6444-48; Poljak et al., 1994, *Structure* 2:1121-23). If the two polypeptide chains of the double-stranded antibody are identical, the double-stranded antibody result from their pairing has the same antigen-binding site. Polypeptide chains with different sequences can be used to prepare double-stranded antibodies with different antigen binding sites. Similarly, three-chain and four-chain antibodies are the antibody that contain three and four polypeptide chains and form three and four antigen binding sites, which may be the same or different.

This article used the method that Kabat et al. described in Sequences of Proteins of Immunological Interest, $5^{th}$ edition, U.S. Dept. Of Health and Human Services, PHS, NIH, NIH Publication No. 91-3242, 1991 to identify the complementary decision region (CDRs) and framework region (FR) of a given antibody. One or more CDRs can be incorporated into a molecule either covalently or noncovalently to make it an antibody. The antibody can incorporate a larger polypeptide chain into the CDR(s). CDR(s) can be covalently attached to another polypeptide chain, or can be non-covalently incorporated. CDRs allows antibodies specifically binding to specific associated antigens.

Antibodies can have one or more binding sites. If there is more than one binding site, the binding site can be the same or different from another. For example, natural human immunoglobulin usually has two identical binding sites, while "bi-specific" or "bifunctional" antibodies have two different binding sites.

The term "murine antibody" includes antibodies having one or more variable and constant regions derived from mouse immunoglobulin sequences.

The term "humanized antibody" is an antibody made by transplanting the sequence of complementary decision regions of mouse antibody molecules into the framework of human antibody variable regions.

The terms "antigen-binding domain," "antigen-binding region," or "antigen-binding site" are the parts of an antibody that contain amino acid residues that interact with an antigen and contribute to its specificity and affinity for the antigen. For antibodies that bind specifically to their antigens, these terms include at least a part of at least one of its CDR domains.

The term "epitope" is the part of a molecule that binds to (for example, by an antibody) the antibody. An epitope may contain a discontinuous part of a molecule (for example, in a polypeptide, the amino acid residues that are discontinuous in the first order of the polypeptide are close enough to each other in the tertiary and quaternary structures of the polypeptide to be bound by an antibody).

The "same percentage" of two polynucleotides or two polypeptide sequences is determined using the GAP computer program's (GCG Wisconsin Package; a part of version 10.3 (Accelrys, San Diego, CA)) default parameters comparison sequence.

The terms "polynucleotide," "oligonucleotide" and "nucleic acid" can be used alternatively throughout the full text and include DNA molecules (e.g., cDNA or genomic DNA), RNA molecules (e.g., mRNA), DNA or RNA analogues and their hybrids produced using nucleotide analogues (e.g., peptide nucleic acids and non-natural nucleotide analogues). Nucleic acid molecules can be single or double stranded. In one embodiment, the nucleic acid molecules contained in this invention contain the continuous open reading frames encoding the antibody or its fragments, derivatives, mutant proteins, or variants.

If their sequences can be reversed and parallel, two single-stranded nucleotides are "complementary" to each other, so that each nucleotide in one polynucleotide is opposite to the complementary nucleotide in the other, no gaps are introduced and no unpaired nucleotides are found at the 5' or 3' ends of each sequence. If two polynucleotides can interbreed under moderately strict conditions, one polynucleotide is "complementary" to the other. Thus, one polynucleotide may be complementary to another polynucleotide, but not its complementary sequence.

The term "carrier" is a nucleic acid that can be used to introduce another nucleic acid connected to it into a cell. One type of carrier is a "plasmid" referring to a linear or circular double-stranded DNA molecule that can be attached to an additional nucleic acid segment. Another type of carrier is a viral vector (e.g., replication-defective retroviruses, adenoviruses, and adenoviral companion viruses) in which additional DNA segments can be introduced into the viral genome. Some carriers can replicate autonomously in the host cells into which they are introduced (For example, bacterial carriers containing the origin of bacterial replication and the free-type mammalian carriers). Other carriers (for example, non-free-type mammalian carriers) are integrated into the host cell genome when introduced into the host cell and thus replicate with the host genome. "Expression carrier" is the type of carrier that can guide the expression of selected polynucleotides.

If the regulatory sequence affects the expression of a nucleotide sequence (for example, expression level, time, or site), then the nucleotide sequence is "operationally linked" to the regulatory sequence. The "regulatory sequence" is the nucleic acid that affects the expression (for example, expression level, time, or site) of the nucleic acid with which it is operationally linked. Regulatory genes, for example, act directly on regulated nucleic acids or through one or more other molecules (e.g., polynucleotides that bind to regulatory sequences and/or nucleic acids). Examples of regulatory sequences include promoters, enhancers, and other expression control elements (e.g., polyadenylation signals). Further examples of regulatory sequences can be described such as Goeddel, 1990, *Gene Expression Technology: Methods in Enzymology*, Volume 185, Academic Press, San Diego, CA; And Baron et al., 1995, *Nucleic Acids Res.* 23:3605-06.

The term "host cell" refers to a cell used to express a nucleic acid such as that provided this article. The host cell may be prokaryotes, such as *E. coli*, or it can be eukaryotes, such as unicellular eukaryotes (yeast or other fungi, for example), plant cells (such as tobacco or tomato plant cells), animal cells (for example, cells of human, monkey, hamster, rat, mouse or insect) or hybridoma. Usually, the host cell is a culture cell that can be transformed or transfected with a peptide encoding nucleic acid, which can then be expressed in the host cell. The phrase "recombinant host cell" can be used to describe a host cell transformed or transfected with an expected expression of nucleic acid. The host cell may also be a cell that contains the nucleic acid but does not express it at the desired level, unless regulatory sequences are introduced to the host cell so that it is operationally linked to the nucleic acid. It should be understood that the term "host cell" refers to not only the specific subject cell but also to the progeny or possible progeny of that cell. Due to certain modifications occurring in subsequent generations, such as mutations or environmental influences, the progeny may in fact be different from the parent cell but still fall within the scope of the terminology used in this invention.

APJ Receptor

APJ is a G protein coupled receptor with 7 transmembrane units, consisting of 377 amino acids (O'Dowd, et al., 1993, *Gene*. 136:355-60). Up to now, studies show that APJ is widely distributed in the human central nervous system and various peripheral tissues such as the lung, heart, breast, etc. (Kawamata et al., 2001, *Biochem. Biophys. Acta.* 1538: 162-71; Medhurst et al., 2003, *J. Neurochem.* 84: 1162-72), especially in cardiovascular endothelial cells and cardiac tissue (Kleiz et al., 2005, *Regul. Pept.* 126: 233-40). APJ is mainly involved in the regulation of the cardiovascular system, and has also been reported to have important significance in the regulation of insulin and the regulation mechanisms of diabetes and obesity-related diseases (Boucher et al., 2005, *Endocrinology* 146:1764-71; Yue et al., 2010, *Am. J. Physiol. Endocrinol. Metab.* 298:E59-67). As used herein, "human APJ" and "hAPJ" both refer to human-derived APJ and can be used interchangeably. As used herein, "murine APJ" and "mAPJ" both refer to murine-derived APJ, and can also be used interchangeably.

In one embodiment, the antibody presented here is an antibody specifically binding to the human APJ. In one embodiment, the fusion protein presented here is a Elabela fusion protein specifically binding to APJ on cell membrane, where the fusion protein can active Elabela/APJ signal transduction in these cells. In a further embodiment, the fusion protein presented here is an Elabela fusion protein binding to human APJ, where the fusion protein can bind to APJ of other species (such as monkey and mice) and activate Elabela/APJ signal transduction in these species.

In one embodiment, the amino acid and polynucleotide sequences of APJ are listed below, with sequence data from the Gene-Bank database of the US national center for biotechnology information and the Uniprot database of the European institute for biological information:

Human (*Homo sapiens*) polynucleotide (SEQ ID NO: 55); accession number: X89271.

Human (*Homo sapiens*) amino acid (SEQ ID NO: 23); accession number: CAA61546.

Monkey (*Rhesus macaque*) polynucleotide (SEQ ID NO: 56); accession number: AF100206.

Monkey (*Rhesus macaque*) amino acid (SEQ ID NO: 24); accession number: AAC72404.

Rat (*Rattus norvegicus*) polynucleotide (SEQ ID NO: 57); accession number: AB033170.

Rat (*Rattus norvegicus*) amino acid (SEQ ID NO: 25); accession number: BAA95002.

Mouse (*Mus musculus*) polynucleotide (SEQ ID NO: 58); accession number: AJ007612; and mouse (*Mus musculus*) amino acid (SEQ ID NO: 26); accession number: CAB50696.

Antibody of Vasoactive Peptide Receptor (APJ Antibody)

In one embodiment, provided herein is the APJ antibody. In another embodiment, the APJ antibody provided herein is the complete APJ antibody. In another embodiment, the APJ antibody provided herein is the APJ antibody fragment. In another embodiment, the APJ antibody provided herein is a derivative of APJ antibody. In another embodiment, the APJ antibody provided herein is the APJ antibody mutant protein. In another embodiment, the APJ antibody provided herein is the variant of APJ antibody.

In one embodiment, the APJ antibody provided herein comprises 1, 2, 3, 4, 5, or 6 amino acid sequences, each of which is independently selected from the amino acid sequences listed below:
a. Light chain CDR1 amino acid sequences: SEQ ID NO: 1, SEQ ID NO: 4, SEQ ID NO: 7, and SEQ ID NO: 10;
b. Light chain CDR2 amino acid sequences: SEQ ID NO: 2, SEQ ID NO: 5, and SEQ ID NO: 8;
c. Light chain CDR3 amino acid sequences: SEQ TD NO: 3, SEQ ID NO: 6, SEQ ID NO: 9, and SEQ ID NO: 11;
d. Heavy chain CDR1 amino acid sequences: SEQ ID NO: 12, SEQ TD NO: 15, and SEQ ID NO: 18;
e. Heavy chain CDR2 amino acid sequences: SEQ ID NO: 13, SEQ ID NO: 16, SEQ ID NO: 19, and SEQ TD NO: 21; and
f. Heavy chain CDR3 amino acid sequences: SEQ ID NO: 14, SEQ ID NO: 17, SEQ ID NO: 20, and SEQ TD NO: 22.

Table 1 lists the amino acid sequences of the light chain CDRs of the APJ antibody provided herein, as well as the corresponding polynucleotide coding sequences. Table 2 lists the amino acid sequences of the heavy chain CDRs of the APJ antibody provided herein, as well as the corresponding polynucleotide coding sequences.

TABLE 1 light chain CDR amino acid sequences and polynucleotide coding sequences

|   | CDR1 | CDR2 | CDR3 |
|---|------|------|------|
| A-1 nucleotide | catgccagtcagaacattcat gtttggttaagc (SEQ ID NO: 27) | aaggcttccaacttgcacaca (SEQ ID NO: 28) | caacagggtcacagttatcctct gacg (SEQ ID NO: 29) |
| A-1 Amino Acid | HASQNIHVWLS (SEQ ID NO: 1) | KASNLHT (SEQ ID NO: 2) | QQGHSYPLT (SEQ ID NO: 3) |
| A-2 nucleotide | agatctagtcagagccttatat acactaatggaaacacctattt acat (SEQ ID NO: 30) | aaagtttccaaccgatttct (SEQ ID NO: 31) | tctcaaaatacacatgttcctctc acg (SEQ ID NO: 32) |
| A-2 Amino Acid | RSSQSLIYINGNTY LH (SEQ ID NO: 4) | KVSNRFS (SEQ ID NO: 5) | SQNTHVPLT (SEQ ID NO: 6) |
| A-3 nucleotide | agatctagtcagaatcttgttca tagtagtggaaacaccccattta gat (SEQ ID NO: 33) | aaagtttccgaccgactttct (SEQ ID NO: 34) | tttcaagcttctcatgttccactca cg (SEQ ID NO: 35) |
| A-3 Amino Acid | RSSQNLVHSSGNTH LD (SEQ ID NO: 7) | KVSDRLS (SEQ ID NO: 8) | FQASHVPLT (SEQ ID NO: 9) |
| A-4 nucleotide | agatctgatcagagtcttgtac atagaactggaaatacccattt agac (SEQ ID NO: 36) | aaagtttccaaccgatttct (SEQ ID NO: 31) | tttcaagcttcacatattccattca ca (SEQ ID NO: 37) |
| A-4 Amino Acid | RSDQSLVHRTGNT HLD (SEQ ID NO: 10) | KVSNRFS (SEQ ID NO: 5) | FQASHIPFT (SEQ ID NO: 11) |
| A-5 nucleotide | cggtccgaccagtctctggtg cacaggaccggcaacacaca cctggat (SEQ ID NO: 38) | aaggtgagcaataggttctcc (SEQ ID NO: 39) | tttcaggccagccacatcccatt cacc (SEQ ID NO: 40) |
| A-5 Amino Acid | RSDQSLVHRTGNT HLD (SEQ ID NO: 10) | KVSNRFS (SEQ ID NO: 5) | FQASHIPFT (SEQ ID NO: 11) |

TABLE 2 heavy chain CDR amino acid sequences and polynucleotide coding sequences

|  | CDR1 | CDR2 | CDR3 |
|---|---|---|---|
| A-1 nucleotide | ggattcccttcaatatcaatg ccatgaac (SEQ ID NO: 41) | cgcataagaagtaaaagtaataatt acgcaacatattataccgattcagt gaaagac (SEQ ID NO: 42) | ggcccatatttatatgctatggact ac (SEQ ID NO: 43) |
| A-1 Amino Acid | GFPFNINAMN (SEQ ID NO: 12) | RIRSKSNNYATYYADS VKD (SEQ ID NO: 13) | GPYLYAMDY (SEQ ID NO: 14) |
| A-2 nucleotide | gggttctcattgaccaactatg gtgtgacc (SEQ ID NO: 44) | gtggtatggggtgacgggaccac aagttctcattcaactctcatgtcc (SEQ ID NO: 45) | tccaactgggggtcatttacttat (SEQ ID NO: 46) |
| A-2 Amino Acid | GFSLTNYGVT (SEQ ID NO: 15) | VVWGDGTTSSHSTLM S (SEQ ID NO: 16) | SNWGSFTY (SEQ ID NO: 17) |
| A-3 nucleotide | ggattcactttcagtagctatg ccatgtct (SEQ ID NO: 47) | tccattagtagtggtggaagtatct actatccagagagtgtgaagggc (SEQ ID NO: 48) | ggccggggggcagccaggc ctggtttgcttac (SEQ ID NO: 49) |
| A-3 Amino Acid | GFTFSSYAMS (SEQ ID NO: 18) | SISSGGSIYYPESVKG (SEQ ID NO: 19) | GRGGSQAWFAY (SEQ ID NO: 20) |
| A-4 nucleotide | ggattcactttcagtagctatg ccatgtct (SEQ ID NO: 47) | tctattagtagtggtggtagtatcta ccttccagacagtttgaagggc (SEQ ID NO: 50) | ggccggggaaatagctccgcct ggtttgcttac (SEQ ID NO: 51) |
| A-4 Amino Acid | GFTFSSYAMS (SEQ ID NO: 18) | SISSGGSIYLPDSLKG (SEQ ID NO: 21) | GRGNSSAWFAY (SEQ ID NO: 22) |
| A-5 nucleotide | ggcttcacctttagctcctacg ccatgagc (SEQ ID NO: 52) | tctatctctagcggcggcagcatct acctgcctgactccctgaagggc (SEQ ID NO: 53) | ggcagaggcaattcctctgcctg gtttgcctat (SEQ ID NO: 54) |
| A-5 Amino Acid | GFTFSSYAMS (SEQ ID NO: 18) | SISSGGSIYLPDSLKG (SEQ ID NO: 21) | GRGNSSAWFAY (SEQ ID NO: 22) |

In one embodiment, the antibody provided herein comprises a sequence different from one of the CDR amino acid sequences listed in Tables 1 and 2 by five, four, three, two or one single amino acid addition, replacement, and/or deletion. In another embodiment, the antibody provided herein contains a sequence different from one of the CDR amino acid sequences listed in Tables 1 and 2 by four, three, two or one single amino acid addition, replacement, and/or deletion.

In another embodiment, the antibody provided herein contains a sequence different from one of the CDR amino acid sequences listed in Tables 1 and 2 by three, two or one single amino acid addition, replacement, and/or deletion.

In another embodiment, the antibody provided herein contains a sequence different from one of the CDR amino acid sequences listed in Tables 1 and 2 by two or one single amino acid addition, replacement, and/or deletion.

In further embodiments, the antibody provided herein contains a sequence that differs from one of the CDR amino acid sequences listed in Tables 1 and 2 by a single amino acid addition, replacement, and/or deletion.

In one embodiment, the APJ antibody provided herein comprises 1 or 2 amino acid sequences, wherein each amino acid sequence is independently selected from the amino acid sequences listed below:
  a. Light chain CDR1 amino acid sequences: SEQ ID NO: 1, SEQ ID NO: 4, SEQ ID NO: 7, and SEQ ID NO: 10;
  b. Heavy chain CDR1 amino acid sequences: SEQ ID NO: 12, SEQ ID NO: 15, and SEQ ID NO: 18.

In another embodiment, the APJ antibody provided herein comprises 1 or 2 amino acid sequences, wherein each amino acid sequence is independently selected from the amino acid sequences listed below:
  a. Light chain CDR2 amino acid sequences: SEQ ID NO: 2, SEQ ID NO: 5, and SEQ ID NO: 8;
  b. Heavy chain CDR2 amino acid sequences: SEQ ID NO: 13, SEQ ID NO: 16, SEQ ID NO: 19, and SEQ ID NO: 21.

In another embodiment, the APJ antibody provided herein comprises 1 or 2 amino acid sequences, wherein each amino acid sequence is independently selected from the amino acid sequences listed below:
  a. Light chain CDR3 amino acid sequences: SEQ ID NO: 3, SEQ ID NO: 6, SEQ ID NO: 9, and SEQ ID NO: 11;
  b. Heavy chain CDR3 amino acid sequences: SEQ ID NO: 14, SEQ ID NO: 17, SEQ ID NO: 20, and SEQ ID NO: 22.

In another embodiment, the APJ antibody provided herein comprises 1, 2, 3 or 4 amino acid sequences, wherein each amino acid sequence is independently selected from the amino acid sequences listed below:
  a. Light chain CDR1 amino acid sequences: SEQ ID NO: 1, SEQ ID NO: 4, SEQ ID NO: 7, and SEQ ID NO: 10;
  b. Heavy chain CDR1 amino acid sequences: SEQ ID NO: 12, SEQ ID NO: 15, and SEQ ID NO: 18;
  c. Light chain CDR2 amino acid sequences: SEQ ID NO: 2, SEQ ID NO: 5, and SEQ ID NO: 8;

d. Heavy chain CDR2 amino acid sequences: SEQ ID NO: 13, SEQ ID NO: 16, SEQ ID NO: 19, and SEQ ID NO: 21.

In another embodiment, the APJ antibody provided herein comprises 1, 2, 3 or 4 amino acid sequences, wherein each amino acid sequence is independently selected from the amino acid sequences listed below:
  a. Light chain CDR1 amino acid sequences: SEQ ID NO: 1, SEQ ID NO: 4, SEQ ID NO: 7, and SEQ ID NO: 10;
  b. Heavy chain CDR1 amino acid sequences: SEQ ID NO: 12, SEQ ID NO: 15, and SEQ ID NO: 18;
  c. Light chain CDR3 amino acid sequences: SEQ ID NO: 3, SEQ ID NO: 6, SEQ ID NO: 9, and SEQ ID NO: 11;
  d. Heavy chain CDR3 amino acid sequences: SEQ ID NO: 14, SEQ ID NO: 17, SEQ ID NO: 20, and SEQ ID NO: 22.

In further embodiments, the APJ antibody provided herein comprises 1, 2, 3 or 4 amino acid sequences, wherein each amino acid sequence is independently selected from the amino acid sequences listed below:
  a. Light chain CDR2 amino acid sequences: SEQ ID NO: 2, SEQ ID NO: 5, and SEQ ID NO: 8;
  b. Heavy chain CDR2 amino acid sequences: SEQ ID NO: 13, SEQ ID NO: 16, SEQ ID NO: 19, and SEQ ID NO: 21;
  c. Light chain CDR3 amino acid sequences: SEQ ID NO: 3, SEQ ID NO: 6, SEQ ID NO: 9, and SEQ ID NO: 11;
  d. Heavy chain CDR3 amino acid sequences: SEQ ID NO: 14, SEQ ID NO: 17, SEQ ID NO: 20, and SEQ ID NO: 22.

In one embodiment, the APJ antibody provided herein comprises 1, 2 or 3 amino acid sequences, wherein each amino acid sequence is independently selected from the amino acid sequences listed below: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

In another embodiment, the APJ antibody provided herein comprises 1, 2 or 3 amino acid sequences, wherein each amino acid sequence is independently selected from the amino acid sequences listed below: SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22.

In one embodiment, the APJ antibody provided herein comprises a combination of light chain and heavy chain CDR1 amino acid sequences independently selected from the list below: SEQ ID NO: 1 and SEQ ID NO: 12, SEQ ID NO: 4 and SEQ ID NO: 15, SEQ ID NO: 7 and SEQ ID NO: 18, and SEQ ID NO: 10 and SEQ ID NO: 18.

In another embodiment, the APJ antibody provided herein comprises a combination of light chain and heavy chain CDR2 amino acid sequences independently selected from the list below: SEQ ID NO: 2 and SEQ ID NO: 13, SEQ ID NO: 5 and SEQ ID NO: 16, SEQ ID NO: 8 and SEQ ID NO: 19, and SEQ ID NO: 5 and SEQ ID NO: 21.

In further embodiments, the APJ antibody provided herein comprises a combination of light chain and heavy chain CDR3 amino acid sequences independently selected from the list below: SEQ ID NO: 3 and SEQ ID NO: 14, SEQ ID NO: 6 and SEQ ID NO: 17, SEQ ID NO: 9 and SEQ ID NO: 20, and SEQ ID NO: 11 and SEQ ID NO: 22.

In one embodiment, the APJ antibody provided herein comprises:
  a. A combination of light and heavy chain CDR1 amino acid sequences independently selected from the list below: SEQ ID NO: 1 and SEQ ID NO: 12, SEQ ID NO: 4 and SEQ ID NO: 15, SEQ ID NO: 7 and SEQ ID NO: 18, and SEQ ID NO: 10 and SEQ ID NO: 18; and
  b. A combination of light and heavy chain CDR2 amino acid sequences independently selected from the list below: SEQ ID NO: 2 and SEQ ID NO: 13, SEQ ID NO: 5 and SEQ ID NO: 16, SEQ ID NO: 8 and SEQ ID NO: 19, and SEQ ID NO: 5 and SEQ ID NO: 21.

In one embodiment, the APJ antibody provided herein comprises:
  a. A combination of light and heavy chain CDR1 amino acid sequences independently selected from the list below: SEQ ID NO: 1 and SEQ ID NO: 12, SEQ ID NO: 4 and SEQ ID NO: 15, SEQ ID NO: 7 and SEQ ID NO: 18, and SEQ ID NO: 10 and SEQ ID NO: 18; and
  b. A combination of light and heavy chain CDR3 amino acid sequences independently selected from the list below: SEQ ID NO: 3 and SEQ ID NO: 14, SEQ ID NO: 6 and SEQ ID NO: 17, SEQ ID NO: 9 and SEQ ID NO: 20, and SEQ ID NO: 11 and SEQ ID NO: 22.

In one embodiment, the APJ antibody provided herein comprises:
  a. A combination of light and heavy chain CDR2 amino acid sequences independently selected from the list below: SEQ ID NO: 2 and SEQ ID NO: 13, SEQ ID NO: 5 and SEQ ID NO: 16, SEQ ID NO: 8 and SEQ ID NO: 19, and SEQ ID NO: 5 and SEQ ID NO: 21;
  b. A combination of light and heavy chain CDR3 amino acid sequences independently selected from the list below: SEQ ID NO: 3 and SEQ ID NO: 14, SEQ ID NO: 6 and SEQ ID NO: 17, SEQ ID NO: 9 and SEQ ID NO: 20, and SEQ ID NO: 11 and SEQ ID NO: 22.

In further embodiments, the APJ antibody provided herein comprises:
  a. A combination of light and heavy chain CDR1 amino acid sequences independently selected from the list below: SEQ ID NO: 1 and SEQ ID NO: 12, SEQ ID NO: 4 and SEQ ID NO: 15, SEQ ID NO: 7 and SEQ ID NO: 18, and SEQ ID NO: 10 and SEQ ID NO: 18;
  b. A combination of light and heavy chain CDR2 amino acid sequences independently selected from the list below: SEQ ID NO: 2 and SEQ ID NO: 13, SEQ ID NO: 5 and SEQ ID NO: 16, SEQ ID NO: 8 and SEQ ID NO: 19, and SEQ ID NO: 5 and SEQ ID NO: 21; and
  c. A combination of light and heavy chain CDR3 amino acid sequences independently selected from the list below: SEQ ID NO: 3 and SEQ ID NO: 14, SEQ ID NO: 6 and SEQ ID NO: 17, SEQ ID NO: 9 and SEQ ID NO: 20, and SEQ ID NO: 11 and SEQ ID NO: 22.

In one embodiment, the antibody provided herein comprises:
  (a) Light chain CDR1 amino acid sequence: SEQ ID NO: 1;
  Light chain CDR2 amino acid sequence: SEQ ID NO: 2;
  Light chain CDR3 amino acid sequence: SEQ ID NO: 3;
  Heavy chain CDR1 amino acid sequence: SEQ ID NO: 12;
  Heavy chain CDR2 amino acid sequence: SEQ ID NO: 13; and
  Heavy chain CDR3 amino acid sequence: SEQ ID NO: 14;
  (b) Light chain CDR1 amino acid sequence: SEQ ID NO: 4;
  Light chain CDR2 amino acid sequence: SEQ ID NO: 5;
  Light chain CDR3 amino acid sequence: SEQ ID NO: 6;

Heavy chain CDR1 amino acid sequence: SEQ ID NO: 15;
Heavy chain CDR2 amino acid sequence: SEQ ID NO: 16; and
Heavy chain CDR3 amino acid sequence: SEQ ID NO: 17;
(c) Light chain CDR1 amino acid sequence: SEQ ID NO: 7;
Light chain CDR2 amino acid sequence: SEQ ID NO: 8;
Light chain CDR3 amino acid sequence: SEQ ID NO: 9;
Heavy chain CDR1 amino acid sequence: SEQ ID NO: 18;
Heavy chain CDR2 amino acid sequence: SEQ ID NO: 19; and
Heavy chain CDR3 amino acid sequence: SEQ ID NO: 20;
(d) Light chain CDR1 amino acid sequences: SEQ ID NO: 10;
Light chain CDR2 amino acid sequences: SEQ ID NO: 5;
Light chain CDR3 amino acid sequences: SEQ ID NO: 11;
Heavy chain CDR1 amino acid sequence: SEQ ID NO: 18;
Heavy chain CDR2 amino acid sequence: SEQ ID NO: 21; and
Heavy chain CDR3 amino acid sequence: SEQ ID NO: 22;

In another embodiment, the antibodies provided herein comprises:
Light chain CDR1 amino acid sequence: SEQ ID NO: 10;
Light chain CDR2 amino acid sequence: SEQ ID NO: 5;
Light chain CDR3 amino acid sequence: SEQ ID NO: 11;
Heavy chain CDR1 amino acid sequence: SEQ ID NO: 18;
Heavy chain CDR2 amino acid sequence: SEQ ID NO: 21; and
Heavy chain CDR3 amino acid sequence: SEQ ID NO: 22;

In one embodiment, the APJ antibody provided herein comprises one or two amino acid sequences, wherein each amino acid sequence is independently selected from the list below:
a. Light chain variable domain amino acid sequences: SEQ ID NO: 59 (L1), SEQ ID NO: 60 (L2), SEQ ID NO: 61 (L3), SEQ ID NO: 62 (L4), and SEQ ID NO: 63 (L5); and an amino acid sequence that is at least 80%, at least 85%, at least 90%, or at least 95% identical to any above sequence; and
b. Heavy chain variable domain amino acid sequence: SEQ ID NO: 64 (H1), SEQ ID NO: 65 (H2), SEQ ID NO: 66 (H3), SEQ ID NO: 67 (H4), and SEQ ID NO: 68 (H5); and an amino acid sequence that is at least 80%, at least 85%, at least 90%, or at least 95% identical to any above sequence.

In another embodiment, the polynucleotide coding sequence for the APJ antibody provided herein comprises one or two polynucleotide coding sequences, wherein each polynucleotide coding sequence is independently selected from the polynucleotide sequences listed below:
a. Light chain variable domain polynucleotide coding sequences: SEQ ID NO: 69, SEQ ID NO: 70, SEQ ID NO: 71, SEQ ID NO: 72, and SEQ ID NO: 73; and a polynucleotide sequence that is at least 80%, at least 85%, at least 90%, or at least 95% identical to any above sequence; and
b. Heavy chain variable domain polynucleotide coding sequences: SEQ ID NO: 74, SEQ ID NO: 75, SEQ ID NO: 76, SEQ ID NO: 77, and SEQ ID NO: 78; and a polynucleotide sequence that is at least 80%, at least 85%, at least 90%, or at least 95% identical to any above sequence.

In one embodiment, the APJ antibody provided herein comprises an amino acid sequence independently selected from the list below: SEQ ID NO: 59, SEQ ID NO: 60, SEQ ID NO: 61, SEQ ID NO: 62, and SEQ ID NO: 63.

In another embodiment, the APJ antibody provided herein comprises an amino acid sequence independently selected from the list below: SEQ ID NO: 64, SEQ ID NO: 65, SEQ ID NO: 66, SEQ ID NO: 67, and SEQ ID NO: 68.

In one embodiment, the APJ antibody provided herein comprises a combination of amino acid sequences independently selected from the light chain and heavy chain variable domain amino acid sequences listed below: SEQ ID NO: 59 and SEQ ID NO: 64 (L1H1), SEQ ID NO: 60 and SEQ ID NO: 65 (L2H2), SEQ ID NO: 61 and SEQ ID NO: 66 (L3H3), SEQ ID NO: 62 and SEQ ID NO: 67 (L4H4), and SEQ ID NO: 63 and SEQ ID NO: 68 (L5H5).

The symbol "LxHy" can also be used herein to refer to the APJ antibody provided herein, wherein "x" corresponds to the light chain variable region sequence code and "y" corresponds to the heavy chain variable region sequence code. For example, L2H2 is a complete antibody with a light chain variable region comprising the SEQ ID NO: 60 (L2) amino acid sequence and a heavy chain variable region comprising the SEQ ID NO: 65 (H2) amino acid sequence.

In one embodiment, the APJ antibody provided herein comprises 1 or 2 amino acid sequences, wherein each amino acid sequence is independently selected from the amino acid sequences listed below:
a. Light chain constant domain amino acid sequences: SEQ ID NO: 79, SEQ ID NO: 80 and SEQ ID NO: 81; and
b. Heavy chain constant domain amino acid sequences: SEQ ID NO: 82, SEQ ID NO: 83 and SEQ ID NO: 84.

In another embodiment, the APJ antibody provided herein comprises a combination of amino acid sequences independently selected from the light chain and heavy chain constant domain amino acid sequences listed below: SEQ ID NO: 79 and SEQ ID NO: 82, SEQ ID NO: 80 and SEQ ID NO: 83, SEQ ID NO: 80 and SEQ ID NO: 84, SEQ ID NO: 81 and SEQ ID NO: 83, and SEQ ID NO: 81 and SEQ ID NO: 84.

In one embodiment, the APJ antibody provided herein comprise the light and heavy chain CDRs listed herein, and the amino acid sequences of the FRs (framework). The amino acid sequences of FRs are contained in the light chain or the heavy chain variable domain and are not separately displayed. In one embodiment, the antibody comprises a light chain CDR1 sequence listed herein. In another embodiment, the antibody comprises a light chain CDR2 sequence listed herein. In another embodiment, the antibody comprises a light chain CDR3 sequence listed herein. In another embodiment, the antibody comprises a heavy chain CDR1 sequence listed herein. In another embodiment, the antibody comprises a heavy chain CDR2 sequence listed herein. In another embodiment, the antibody comprises a heavy chain CDR3 sequence listed herein. In another embodiment, the antibody comprises a light chain FR1 sequence herein. In another embodiment, the antibody comprises a light chain FR2 sequence herein. In another embodiment, the antibody comprises a light chain FR3 sequence herein. In another embodiment, the antibody comprises a light chain FR4 sequence herein. In another embodiment, the antibody comprises a heavy chain FR1 sequence herein. In another embodiment, the antibody comprises a heavy chain FR2 sequence herein. In another embodiment, the antibody comprises a heavy chain FR3 sequence herein. In a further embodiment, the antibody comprises a heavy chain FR4 sequence herein.

In one embodiment, a light chain CDR3 sequence of the antibody differs from SEQ ID NO: 11 of the light chain CDR3 amino acid sequence illustrated above by no more than 6, 5, 4, 3, 2 or 1 amino acid addition(s), substitution(s), and/or deletion(s). In another embodiment, a heavy chain CDR sequence of the antibody differs from SEQ ID NO: 22 of the heavy chain CDR3 amino acid sequence illustrated above by no more than 6, 5, 4, 3, 2 or 1 amino acid addition(s), substitution(s), and/or deletion(s). In a further embodiment, a light chain CDR3 sequence of the antibody differs from SEQ ID NO: 11 of the light chain CDR3 amino acid sequence illustrated above by no more than 6, 5, 4, 3, 2 or 1 amino acid addition(s), substitution(s), and/or deletion(s), and a heavy chain CDR3 sequence of the antibody differs from SEQ ID NO: 22 of the heavy chain CDR3 amino acid sequence illustrated above by no more than 6, 5, 4, 3, 2 or 1 amino acid addition(s), substitution(s), and/or deletion(s).

In one embodiment, the APJ antibody provided herein comprises a light chain variable domain amino acid sequence selected from L4 (SEQ ID NO: 62) or L5 (SEQ ID NO: 63) light chain variable domain sequence listed herein. In one embodiment, the amino acid sequence of the light chain variable domain of the APJ antibody differs from the amino acid sequence of one light chain variable domain of L4 (SEQ ID NO: 62) or L5 (SEQ ID NO: 63) by 15, 14, 13, 12, 11, 10, 9, 8, 7, 6, 5, 4, 3, 2, or 1 amino acid difference, wherein the difference in each sequence is independently a deletion, insertion or substitution of an amino acid residue. In another embodiment, the light chain variable domain amino acid sequence of the APJ antibody comprises an amino acid sequence at least 70%, at least 75%, at least 80%, at least 85%, at least 90%, at least 95%, at least 97%, or at least 99% identical to the amino acid sequence of one light chain variable domain of L4 (SEQ ID NO: 62) or L5 (SEQ ID NO: 63). In another embodiment, the polynucleotide coding sequence of the light chain variable domain of the APJ antibody comprises a nucleotide coding sequence at least 70%, at least 75%, at least 80%, at least 85%, at least 90%, at least 95%, at least 97% or at least 99% identical to one polynucleotide coding sequence of L4 (SEQ ID NO: 72) or L5 (SEQ ID NO: 73). In another embodiment, the polynucleotide coding sequence of the light chain variable domain of the APJ antibody comprises a polynucleotide sequence hybridized under moderate conditions with a complementary polynucleotide coding sequence of one light chain variable domain of L4 (SEQ ID NO: 72) or L5 (SEQ ID NO: 73). In a further embodiment, the polynucleotide coding sequence of the light chain variable domain of the APJ antibody comprises a polynucleotide sequence hybridized under stringent conditions with a complementary polynucleotide coding sequence of one light chain variable domain of L4 (SEQ ID NO: 72) or L5 (SEQ ID NO: 73).

In one embodiment, the APJ antibody provided herein comprises a heavy chain variable domain amino acid sequence selected from H4 (SEQ ID NO: 67) or H5 (SEQ ID NO: 68) heavy chain variable domain sequences listed herein. In another embodiment, the heavy chain variable domain amino acid sequence of the APJ antibody differs from one heavy chain variable domain amino acid sequence of H4 (SEQ ID NO: 67) or H5 (SEQ ID NO: 68) by 15, 14, 13, 12, 11, 10, 9, 8, 7, 6, 5, 4, 3, 2, or 1 amino acid difference, wherein the difference in each sequence is independently a deletion, insertion or substitution of one amino acid residue. In another embodiment, the heavy chain variable domain amino acid sequence of the APJ antibody comprises an amino acid sequence at least 70%, at least 75%, at least 80%, at least 85%, at least 90%, at least 95%, at least 97%, or at least 99% identical to one heavy chain variable domain sequence of H4 (SEQ ID NO: 67) or H5 (SEQ ID NO: 68). In another embodiment, the heavy chain variable domain of the APJ antibody comprises a polynucleotide coding sequence at least 70%, at least 75%, at least 80%, at least 85%, at least 90%, at least 95%, at least 97%, or at least 99% identical to one heavy chain variable domain polynucleotide coding sequence of H4 (SEQ ID NO: 77) or H5 (SEQ ID NO: 78). In another embodiment, the polynucleotide coding sequence of the APJ antibody heavy chain variable domain comprises a polynucleotide sequence hybridized to a complementary polynucleotide coding sequence of one heavy chain variable domain of H4 (SEQ ID NO: 77) or H5 (SEQ ID NO: 78) under moderately strict conditions. In one embodiment, the polynucleotide coding sequence of the APJ antibody heavy chain variable domain comprises a polynucleotide sequence hybridized under stringent conditions with a complementary polynucleotide coding sequence of one heavy chain variable domain of H4 (SEQ ID NO: 77) or H5 (SEQ ID NO: 78).

In one embodiment, the antibody provided herein is an antibody comprising a combination of L1H1 (SEQ ID NO: 59 and SEQ ID NO: 64), L2H2 (SEQ ID NO: 60 and SEQ ID NO: 65), L3H3 (SEQ ID NO: 61 and SEQ ID NO: 66), L4H4 (SEQ ID NO: 62 and SEQ ID NO: 67), or L5H5 (SEQ ID NO: 63 and SEQ ID NO: 68), or of a desired phenotype (for example, IgA, IgG1, IgG2a, IgG2b, IgG3, IgM, IgE, or IgD), or a Fab or F(ab')2 fragment thereof.

In one embodiment, the antibody provided herein is an antibody comprising a combination of L4H4 (SEQ ID NO: 62 and SEQ ID NO: 67) or L5H5 (SEQ ID NO: 63 and SEQ ID NO: 68), or of an exchanged isotype thereof (for example, IgA, IgG1, IgG2a, IgG2b, IgG3, IgM, IgE, or IgD), or a Fab or F(ab')2 fragment thereof.

The antibodies provided herein can comprise any of the known constant regions of the field. The light chain constant region can be, for example, κ or λ light chain constant region, such as a mouse κ or λ light chain constant region. The heavy chain constant region can be, for example, an α, δ, ε, γ, or μ heavy chain constant region, such as the mouse α, δ, ε, γ, or heavy chain constant region. In an embodiment, the light or heavy chain constant region is a fragment, derivative, variant, or mutant of the natural constant region.

In one embodiment, the antibody provided herein further comprises a human light chain κ constant domain or fragment thereof. The amino acid sequence of the light chain constant region is as follows:

Human light chain κ constant domain amino acid sequence: (SEQ ID NO: 80); and

Human light chain λ constant domain amino acid sequence: (SEQ ID NO: 81).

In another embodiment, the antibody provided herein further comprises a human heavy chain heavy chain, or a fragment thereof. The heavy chain constant domain amino acid sequences are provided as follows:

Human heavy chain constant domain amino acid sequence (hIgG2): (SEQ ID NO: 83), and Human heavy chain constant domain amino acid sequence (hIgG4): (SEQ ID NO: 84).

In one embodiment, the heavy and light chain amino acid sequences of the APJ antibody provided herein are as follows: SEQ ID NO:157 and SEQ ID NO:158.

In one embodiment, the APJ antibodies provided herein are selected from mouse-derived antibodies, humanized antibodies, chimeric antibodies, monoclonal antibodies, polyclonal antibodies, recombinant antibodies, antigen-binding antibody fragments, single-chain antibodies, double-chain antibodies, triple-chain antibodies, quadruple-chain antibodies, Fab fragments, F(ab')x fragments, structural domain antibodies, IgD antibodies, IgE antibodies, IgM antibodies, IgG1 antibodies, IgG2 antibodies, IgG3 antibodies, or IgG4 antibodies.

In another embodiment, the APJ antibody provided herein is an APJ monoclonal antibody.

In another embodiment, the APJ antibody provided herein is a monoclonal antibody comprising a combination of amino acid sequences selected from the list below: SEQ ID NO: 59 and SEQ ID NO: 64, SEQ ID NO: 60 and SEQ ID NO: 65, SEQ ID NO: 61 and SEQ ID NO: 66, SEQ ID NO: 62 and SEQ ID NO: 67, and SEQ ID NO: 63 and SEQ ID NO: 68.

In one embodiment, the APJ antibody provided herein is a mouse APJ antibody. In another embodiment, the APJ antibody provided herein is a humanized APJ antibody.

In one embodiment, the Kd value of the APJ antibody provided herein is about 1 nM to 200 nM or about 1 nM to 100 nM.

Antibodies and Antibody Fragments

In one embodiment, the antibody provided herein is a full-length antibody (including polyclonal, monoclonal, chimeric, humanized or human antibody with full length heavy and/or light chains). In another embodiment, the antibody provided herein is an antibody fragment, for example, $F(ab')_2$, Fab, Fab', Fv, Fc, or Fd fragment, and can be incorporated into single domain antibodies, single-chain antibodies, maxibodies, minibodies, intrabodies, double-chain antibodies, triple-chain antibodies, tetra-chain antibodies, v-NAR, or bis-scFv (see e.g., Hollinger and Hudson, 2005, *Nature Biotechnology*, 23, 9, 1126-1136). In another embodiment, the antibody provided herein also includes antibody polypeptides such as those disclosed in U.S. Pat. No. 6,703,199, including fibronectin polypeptide monobodies. In another embodiment, the antibody provided herein also includes other antibody polypeptides disclosed in U.S. Patent Publication 2005/0238646, which are single-chain polypeptides.

In one embodiment, the variable regions of the IgG gene expressing a monoclonal antibody of interest in a hybridoma are amplified using nucleotide primers. These primers can be synthesized by one of ordinary skill in the field, or can be purchased from commercially available vendors, which synthesizes primers for mouse and human variable regions including, among others, primers for $V_{Ha}$, $V_{Hb}$, $V_{Hc}$, $V_{Hd}$, $C_{H1}$, $V_L$ and $C_L$ regions. These primers can be used to amplify heavy or light chain variable regions, which can then be inserted into vectors such as IMMUNOZAP™ H or IMMUNOZAP™ L (Stratagene), respectively. These vectors can then be introduced into *E. coli*, yeast, or mammalian-based systems for expression. Large amounts of a single-chain protein containing a fusion of the $V_H$ and $V_L$ regions can be produced using these methods (see Bird el al., 1988, *Science* 242:423-426).

It should be understood by one skilled in the field that certain proteins, such as antibodies, can undergo a variety of post-translational modifications. The types and extents of these modifications often depend on the host cell lines used to express the protein as well as the culture conditions. Such modifications can include variations in glycosylation, methionine oxidation, diketopiperizine formation, aspartate isomerization and asparagine deamidation. The carboxyl-terminal basic residue (such as lysine or arginine) may be lost due to the frequent modification of carboxypeptidases (as described in Harris, R. J., 1995, *Journal of Chromatography* 705:129-134).

A common method for production of a murine monoclonal antibody is by hybridoma cells. Monoclonal antibodies can be isolated and purified by a variety of well-established techniques. Such isolation techniques include affinity chromatography with Protein-A Sepharose, size-exclusion chromatography, and ion-exchange chromatography (see, e.g., Coligan at pages 2.7.1-2.7.12 and pages 2.9.1-2.9.3; Baines et al., "Purification of Immunoglobulin G (IgG)," *Methods in Molecular Biology*, Vol. 10, pages 79-104 (The Humana Press, Inc. 1992)). A monoclonal antibody can be purified by affinity chromatography using an appropriate ligand selected based on particular properties of the antibody (e.g., heavy or light chain isotype, binding specificity, etc.). Examples of suitable ligands immobilized on a solid support include Protein A, Protein G, an anti-constant region (light chain or heavy chain) antibody, an anti-idiotype antibody, and a TGF-β binding protein, or a fragment or variant thereof.

Molecular evolution of the complementarity determining regions (CDRs) in the center of the antibody binding site also has been used to isolate antibodies with increased affinities, for example, antibodies having increased affinities for c-erbB-2, as described by Schier et al., 1996, *J. Mol. Biol.* 263:551-567. Accordingly, such techniques are useful in preparing antibodies against human APJ.

Antibodies against human APJ can be used, for example, in assays to detect the presence of APJ, either in vitro or in vivo.

Antibodies can also be prepared by any of the conventional techniques. For example, they can be purified from cells that naturally express them (e.g., an antibody can be purified from a hybridoma that produces it) or produced in recombinant expression systems using any technique known in the field. For example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988). This is discussed in the nucleic acid section below.

Antibodies can be prepared and screened for desired properties by any known techniques. Some techniques relate to the isolation of nucleic acids encoding polypeptide chains (or portions thereof) of related antibodies (e.g., anti-APJ antibodies) and manipulation of nucleic acid. Nucleic acids can be fused with another relevant nucleic acid or modified by recombinant DNA techniques (e.g., induced mutations or other conventional techniques) to add, delete or replace one or more amino acid residues.

Where it is desired to improve the affinity of antibodies according to the invention containing one or more of the above-mentioned CDRs, such antibodies can be obtained by a number of affinity maturation protocols, including maintaining the CDRs (Yang et al., 1995, *J. Mol. Biol.*, 254:392-403), chain shuffling (Marks et al., 1992, *Bio/Technology*, 10:779-783), use of mutation strains of *E. coli*. (Low et al., 1996, *J. Mol. Biol.*, 250:350-368), DNA shuffling (Patten et al., 1997, *Curr. Opin. Biotechnol.*, 8:724-733), phage display (Thompson et al., 1996, *J. Mol. Biol.*, 256:7-88) and additional PCR techniques (Crameri et al., 1998, *Nature*, 391:288-291). All of these methods of affinity maturation are discussed in Vaughan et al., 1998, *Nature Biotechnology*, 16:535-539.

In one embodiment, fragments of the APJ antibody are provided herein. Such fragments can comprise entirely antibody-derived sequences or additional sequences. Examples of antigen binding fragments include Fab, F(ab')2, single chain antibodies, diabodies, tribodies, tetrabodies, and domain antibodies. Other examples are provided in Lunde et al., 2002, *Biochem. Soc. Trans.* 30:500-06.

Single chain antibodies can be formed by linking heavy and light chain variable domain (Fv region) fragments via an amino acid bridge (short peptide linker), resulting in a single polypeptide chain. Such single-chain Fvs (scFvs) have been prepared by fusion DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, multimeric scFvs that bind to different epitopes can be formed (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879-83; Ward et al., 1989, *Nature* 334:544-6; de Graaf et al., 2002, *Methods Mol. Biol.* 178:379-87. Single chain antibodies derived from antibodies provided herein including, but not limited to, scFvs comprising the variable domain combination L1H1, are encompassed by the present invention Antigen binding fragments derived from an antibody can also be obtained, for example, by proteolytic hydrolysis of the antibody, for example, pepsin or papain digestion of a whole antibody according to conventional methods. By way of example, antibody fragments can be produced by enzymatic cleavage of antibodies with pepsin to provide a SS fragment termed F(ab')2. This fragment can be further cleaved using a thiol reducing agent to produce 3.5 S Fab' monovalent fragments. Optionally, the cleavage reaction can be performed using a blocking group for the sulfhydryl groups that results in cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoffet et al., 1960, *Arch. Biochem. Biophys.* 89:230; Porter, 1959, *Biochem. J.* 73:119; Edelman et al., Methods in Enzymology 1:422 (Academic Press 1967); and by Andrews, S. M. and Titus, J. A. in Current Protocols in Immunology (Coligan J. E., et al., eds, John Wiley & Sons, New York, 2003), pages 2.8.1-2.8.10 and 2.10 A. 1-2.10 A. 5. Other methods for cleaving antibodies, such as separating heavy chains to form monovalent light-heavy chain fragments (Fd), further cleaving of fragments, or other enzymatic, chemical, or genetic techniques can also be used, so long as the fragments bind to the antigen that is recognized by the intact antibody.

Another form of an antibody fragment is a peptide comprising one or more complementarity determining regions (CDRs) of an antibody. CDRs can be obtained by constructing polynucleotides that encode the CDRs. Such polynucleotides are prepared, for example, by using the polymerase chain reaction to synthesize the variable region using mRNA of antibody-producing cells as a template (see, for example, Larrick et al., 1991, *Methods: A Companion to Methods in Enzymology* 2:106; Courtenay-Luck, "Genetic Manipulation of Monoclonal Antibodies," Monoclonal Antibodies: Production, Engineering and Clinical Application, Ritter et al. (eds.), page 166 (*Cambridge University Press* 1995); and Ward el al., "Genetic Manipulation and Expression or Antibodies," in Monoclonal Antibodies: Principles and Applications, Birch et al., (eds.), page 137 (Wiley-Liss, Inc. 1995)). The antibody fragment further can comprise at least one variable region domain of an antibody described herein. Thus, for example, the V region domain can be monomeric and be a $V_H$ or $V_L$ domain, which can bind to APJ with an affinity of $1 \times 10^{-7}$ M or more as described below.

The variable region domain can be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain can be covalently attached at a C-terminal amino acid to at least one other antibody domain or a fragment thereof. Thus, for example, a $V_H$ domain that is present in the variable region domain can be linked to an immunoglobulin $C_{H1}$ domain or a fragment thereof. Similarly, a $V_L$ domain can be linked to a $C_K$ domain or a fragment thereof. In this way, for example, the antibody can be a Fab fragment, wherein the antigen binding domain contains associated $V_H$ and $V_L$ domains covalently linked at their C-termini to a $C_{H1}$ and Cκ domain, respectively. The $C_{H1}$ domain can be extended with further amino acids, for example to provide a hinge region or a portion of a hinge region domain as found in a Fab' fragment, or to provide further domains, such as antibody $C_{H2}$ and $C_{H3}$ domains.

Derivatives and Variants of Antibodies

The nucleotide sequences of L1 and H1 can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, *Gene* 42:133; Bauer et al., 1985, *Gene* 37:73; Craik, 1985, *BioTechniques*, 3:12-19; Smith et al., 1981, *Genetic Engineering: Principles and Methods*, Plenum Press; and U.S. Pat. Nos. 4,518,584 and 4,737,462. These and other methods can be used to make, for example, derivatives of APJ antibodies that have a desired property, for example, an increase in affinity, avidity, or specificity for APJ or in vivo or in vitro stability, or reduced in vivo side-effects as compared to the underivatized antibody.

Other derivatives of anti-APJ receptor antibodies within the scope or this invention include covalent or aggregative conjugates of anti-APJ receptor antibodies or fragments thereof, with other proteins or polypeptides, such as by expression of recombinant fusion proteins comprising heterologous polypeptides fused to the N-terminus or C-terminus or an anti-APJ antibody polypeptide. For example, the conjugated peptide can be a heterologous signal (or leader) polypeptide, e.g., the yeast alpha-factor leader or a peptide such as an epitope tag. An antibody containing fusion proteins can comprise peptides added to facilitate purification or identification of antigen binding protein (e.g., poly-His). An antibody also can be linked to the FLAG peptide as described in Hopp et al., 1988, *Bio Technology* 6:1204, and U.S. Pat. No. 5,011,912. The FLAG peptide is highly antigenic and provides an epitope reversibly bound by a specific monoclonal antibody (mAb), enabling rapid assay and facile purification of an expressed recombinant protein. Reagents useful for preparing fusion proteins in which the FLAG peptide is fused to a given polypeptide are commercially available (Sigma, St. Louis, Mo.). In another embodiment, oligomers that contain one or more antibodies can be employed as APJ receptor antagonists. Oligomers can be in the form of covalently-linked or non-covalently-linked dimers, trimers, or higher oligomers. Oligomers comprising two or more antibodies are contemplated for use, with one example being a homodimer. Other oligomers include heterodimers, homotrimers, heterotrimers, homotetramers, heterotetramers, etc.

One embodiment is directed to oligomers comprising multiple antibodies joined via covalent or non-covalent interactions between peptide moieties fused to the antibodies. Such peptides can be peptide linkers (spacers), or peptides that have the property of promoting oligomerization. Leucine zippers and certain polypeptides derived from antibodies are among the peptides that can promote oligomerization of antibodies attached thereto, as described in more detail below.

In particular embodiments, the oligomers comprise from two to four antibodies. The antibodies of the oligomer can be in any form, such as any of the forms described above, e.g., variants or fragments. Preferably, the oligomers comprise antibodies that have APJ binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *PNAS USA* 88:10535; Byrn et al., 1990, *Nature* 344:677; and Hollenbaugh et al., 1992 "Construction of Immunoglobulin Fusion Proteins," in *Current Protocols in Immunology*, Suppl. 4, pages 10.19.1-10.19.11. One embodiment provided herein is directed to a dimer comprising two fusion proteins created by fusing an Elabela fragment of an anti-APJ antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon inter-chain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. In other embodiments, the variable portion of the heavy and/or light chains of an APJ antibody can be substituted for the variable portion of an antibody heavy and/or light chain.

Alternatively, the oligomer is a fusion protein comprising multiple antibodies, with or without peptide linkers (spacer peptides). Among the suitable peptide linkers are those described in U.S. Pat. Nos. 4,751,180 and 4,935,233.

Another method for preparing oligomeric antibodies involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-78. In one method, recombinant fusion proteins comprising an anti-APJ antibody fragment or derivative fused to a leucine zipper peptide are expressed in suitable host cells, and the soluble oligomeric anti-APJ antibody fragments or derivatives that form are recovered from the culture supernatant.

In another embodiment, the antibody derivatives can comprise at least one of the CDRs disclosed herein. For example, one or more CDR can be incorporated into known antibody framework regions (IgG1, IgG2, etc.), or conjugated to a suitable vehicle to enhance the half-life thereof. Suitable vehicles include, but are not limited to Fc, albumin, transferrin, and the like. These and other suitable vehicles are known in the field. Such conjugated CDR peptides can be in monomeric, dimeric, tetrameric, or other form. In one embodiment, one or more water-soluble polymer is bonded at one or more specific position, for example at the amino terminus, of a binding agent. In an example, an antibody derivative comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

Provided herein is an antibody having at least one amino acid substitution, providing that the antibody retains binding specificity. Therefore, modifications to the antibody structures are encompassed within the scope of the invention. These can include amino acid substitutions, which may be conservative or non-conservative, that do not destroy the human APJ binding capability of an antibody. Conservative amino acid substitutions may encompass non-naturally occurring amino acid residues, which are typically incorporated by chemical peptide synthesis rather than by synthesis in biological systems. This include peptidomimetics and other reversed or inverted forms of amino acid moieties. A conservative amino acid substitution can also involve a substitution of a native amino acid residue with a normative residue such that there is little or no effect on the polarity or charge of the amino acid residue at that position. Non-conservative substitutions can involve the exchange of a member of one class of amino acids or amino acid mimetics for a member from another class with different physical properties (e.g., size, polarity, hydrophobicity, charge).

Moreover, one skilled in the field may generate variants to be tested, which contain a single amino acid substitution at each desired amino acid residue. The variants can then be screened using activity assays known to those skilled in the field. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the field can readily determine the amino acids where further substitutions should be avoided either alone or in combination with other mutations.

In certain embodiments, one skilled in the field is able to determine suitable variants of the polypeptide as set forth herein using well-known techniques. In certain embodiments, one skilled in the field may identify suitable areas of the molecule that may be changed without destroying activity by targeting regions not to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure. Additionally, one skilled in the field can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the field may opt for chemically similar amino acid substitutions for such predicted important amino acid residues.

In certain embodiments, one skilled in the field can also analyze the three-dimensional structure and amino acid sequence in relation to that structure in similar polypeptides. In view of such information, one skilled in the field may predict the alignment of amino acid residues of an antibody with respect to its three-dimensional structure. In certain embodiments, one skilled in the field may choose not to make radical changes to amino acid residues predicted to be on the surface of the protein, since such residues may be involved in important interactions with other molecules. A number of scientific publications have been devoted to the prediction of secondary structure. See Moult, 1996, *Curr. Op. Biotech.* 7:422-427; Chou et al., 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276 and Chou et al., *Biophys. J.* 26:367-384. Moreover, computer programs are currently available to assist with predicting secondary structure. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within the structure of a polypeptide or protein. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction becomes significantly more accurate.

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (see Holm, supra (1999), and Brenner, supra (1997)). In certain embodiments, variants of antibodies include glycosylation variants, wherein the number and/or type of glycosylation sites have been altered compared to the amino acid sequences of a parent polypeptide. In certain embodiments, variants comprise a greater or lesser number of N-linked glycosylation sites than the native protein. Alternatively, elimination of such a sequence by substitutions removes an existing N-linked carbohydrate chain. Also provided is a rearrangement of N-linked carbohydrate chains, wherein one or more N-linked glycosylation sites (typically those that are naturally occurring) are eliminated and one or more new N-linked sites are created. Additional preferred antibody variants include cysteine variants, wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the field at the time such substitutions are desired. In certain embodiments, amino acid substitutions can be used to identify important residues of antibodies to human APJ, or to increase or decrease the affinity of the antibodies to human APJ described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) can be made in the naturally-occurring sequence (in certain embodiments, in the portion of the polypeptide outside the domain(s) forming intermolecular contacts). In certain embodiments, a conservative amino acid substitution typically cannot substantially change the structural characteristics of the parent sequence (e.g., a replacement amino acid should not break a helix that occurs in the parent sequence, or disrupt other types of secondary structure that characterizes the parent sequence). Examples of field-recognized polypeptide secondary and tertiary structures are described in Proteins, Structures and Molecular Principles (Creighton, Ed., W. H. Freeman and Company, New York (1984)); Introduction to Protein Structure (Branden and Tooze, Eds., Garland Publishing, New York, N.Y. (1991)); and Thornton et al., 1991, *Nature* 354:105, each of which is incorporated herein by reference.

In certain embodiments, antibodies of the invention can be chemically bonded with polymers, lipids, or other moieties.

The antigen binding agents can comprise at least one of the CDRs described herein incorporated into a biocompatible framework structure. In one embodiment, the biocompatible framework structure comprises a polypeptide or portion thereof that is sufficient to form a conformationally stable structural support, or framework, or scaffold, which is able to present one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically, the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains can be used (see, e.g., Nygren and Uhlen, 1997, *Current Opinion in Structural Biology* 7:463-469).

Additionally, one skilled in the field recognizes that suitable binding agents include portions of these antibodies, such as one or more of heavy chain CDR1, CDR2, CDR3, light chain CDR1, CDR2 and CDR3 as specifically disclosed herein. At least one of the regions of heavy chain CDR1, CDR2, CDR3, CDR1, CDR2 and CDR3 can have at least one amino acid substitution, provided that the antibody retains the binding specificity of the non-substituted CDR. The non-CDR portion of the antibody can be a non-protein molecule, wherein the binding agent cross-blocks the binding of an antibody disclosed herein to human APJ. The non-CDR portion of the antibody can be a non-protein molecule in which the antibody exhibits a similar binding pattern to human Elabela peptides in a competition binding assay as that exhibited by antibody L4H4. The non-CDR portion of the antibody can be composed of amino acids, wherein the antibody is a recombinant binding protein or a synthetic peptide, and the recombinant binding protein cross-blocks the binding of an antibody disclosed herein to human APJ. The non-CDR portion of the antibody can be composed of amino acids, wherein the antibody is a recombinant antibody, and the recombinant antibody exhibits a similar binding pattern to human APJ peptides in a competition binding assay as exhibited by at least one of the antibodies L4H4.

Fusion Protein of APJ Antibody and Elabela (Elabela Fusion Protein)

In one embodiment, provided herein is an Elabela fusion protein comprising an antibody specifically binding to APJ and an Elabela fragment.

In another embodiment, provided herein is an Elabela fusion protein comprising an antibody specifically binding to APJ, as well as 1, 2, 3, 4, 5, 6, 7 or 8 Elabela fragments and peptide linker (Linker); the fusion protein connects the N-terminus of one Elabela fragment to the C-terminus of the heavy or light chain of one APJ antibody through a peptide linker sequence (Linker), wherein each Elabela fragment is independently a forward Elabela fragment or mutant; or the fusion protein connects the C-terminus of one Elabela fragment with the N-terminus of the heavy or light chain of one APJ antibody, wherein each Elabela fragment is independently a reverse Elabela fragment or mutant.

In another embodiment, provided herein is an Elabela fusion protein comprising an antibody specifically binding to APJ, as well as 1, 2, 3 or 4 Elabela fragments and peptide linker (Linker); the fusion protein connects the N-terminus of one Elabela fragment with the C-terminus of the heavy or light chain of one APJ antibody through a peptide linker sequence (Linker), wherein each Elabela fragment is independently a forward Elabela fragment or mutant.

In another embodiment, provided herein is an Elabela fusion protein comprising an antibody specifically binding to APJ, as well as 1, 2, 3 or 4 Elabela fragments and peptide linker (Linker); the fusion protein connects the C-terminus of one Elabela fragment with the N-terminus of the heavy or light chain of one APJ antibody through a peptide linker sequence (Linker), wherein each Elabela fragment is independently a reverse Elabela fragment or mutant.

In another embodiment, provided herein is an Elabela fusion protein comprising an antibody specifically binding to APJ, as well as two Elabela fragments and peptide linker (Linker); the fusion protein connects the N-terminus of one Elabela fragment with the C-terminus of the heavy or light chain of one APJ antibody through a peptide linker sequence (Linker), wherein each Elabela fragment is independently a forward Elabela fragment or mutant.

In another embodiment, provided herein is an Elabela fusion protein comprising an antibody specifically binding to APJ, as well as two Elabela fragments and peptide linker (Linker); the fusion protein connects the C-terminus of one Elabela fragment with the N-terminus of the heavy or light chain of one APJ antibody through a peptide linker sequence (Linker), wherein each Elabela fragment is independently a reverse Elabela fragment or mutant.

In another embodiment, provided herein is an Elabela fusion protein comprising a APJ antibody and two Elabela fragments and peptide linker (Linker); the fusion protein connects the N-terminus of one Elabela fragment with the C-terminus of one APJ antibody light chain: N'—R-Linker-Elabela-C'; or connects the N-terminus of one Elabela fragment with the C-terminus of one APJ antibody heavy chain: N'—R-Linker-Elebela-C'; wherein: N' represents the N-terminus of the fusion protein polypeptide chain, C' represents the C-terminus of the fusion protein polypeptide chain, Elebela represents a forward Elabela fragment or mutant, R represents the amino acid sequence of a light chain or heavy chain of APJ antibody, and Linker represents a peptide linker sequence.

In another embodiment, provided herein is an Elabela fusion protein comprising a APJ antibody and two Elabela fragments and peptide linker (Linker); the fusion protein connects the C-terminus of one Elabela fragment with the N-terminus of one APJ antibody light chain through a peptide linker (Linker): N'-Elabela-Linker-R—C'; or connects the C-terminus of one Elabela fragment with the N-terminus of one APJ antibody heavy chain: N'-Elabela-Linker-R—C'; wherein: N' represents the N-terminus of the fusion protein polypeptide chain, C' represents the C-terminus of the fusion protein polypeptide chain, Elebela represents a reverse Elabela fragment or mutant, R represents the amino acid sequence of a light chain or heavy chain of APJ antibody, and Linker represents the peptide linker sequence.

In another embodiment, provided herein is an Elabela fusion protein comprising a APJ antibody and two Elabela fragments and peptide linker (Linker); the fusion protein connects the N-terminus of one Elabela fragment with the C-terminus of one APJ antibody light chain through a peptide linker (Linker): N'—R-Linker-Elabela-C'; wherein: N' represents the N-terminus of the fusion protein polypeptide chain, C' represents the C-terminus of the fusion protein polypeptide chain, Elebela represents a forward Elabela fragment or mutant, R represents an APJ antibody light chain amino acid sequence, and Linker represents a peptide linker sequence.

In another embodiment, provided herein is an Elabela fusion protein comprising a APJ antibody and two Elabela fragments and peptide linker (Linker); the fusion protein connects the N-terminus of one Elabela fragment with the C-terminus of one APJ antibody heavy chain through a peptide linker (Linker): N'—R-Linker-Elabela-C'; wherein: N' represents the N-terminus of the fusion protein polypeptide chain, C' represents the C-terminus of the fusion protein polypeptide chain, Elebela represents a forward Elabela fragment or mutant, R represents an APJ antibody heavy chain amino acid sequence, and Linker represents a peptide linker sequence.

In one embodiment, in the Elebela fusion proteins provided herein, the forward Elebela fragment or variant thereof is independently selected from one of the following amino acid sequences: SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 166, and SEQ ID NO: 167.

In one embodiment, in the Elebela fusion proteins provided herein, the forward Elebela fragment is independently selected from one of the following amino acid sequences: SEQ ID NO: 92, SEQ ID NO: 93, SEQ ID NO: 103, SEQ ID NO: 107, SEQ ID NO: 115, SEQ ID NO: 116, SEQ ID NO: 166, and SEQ ID NO: 167.

In one embodiment, in the Elebela fusion proteins provided herein, the reversed Elebela fragment or variant thereof is independently selected from one of the following amino acid sequences: SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, and SEQ ID NO: 155.

In one embodiment, in the Elebela fusion proteins provided herein, wherein the peptide linker (Linker) sequence independently comprises from 1 to 200 amino acid residues, from 2 to 100 amino acid residues, from 5 to 50 amino acid residues, from 6 to 25 amino acid residues, or from 10 to 20 amino acid residues.

In another embodiment, in the Elebela fusion proteins provided herein, wherein the linker (Linker) sequence independently comprises the full length, a part of, or repeated amino acid sequence of one of the following amino acid sequences: SEQ ID NO: 122, SEQ ID NO: 123, and SEQ ID NO: 124.

In another embodiment, in the Elebela fusion proteins provided herein, the Linker sequence is selected independently from amino acid sequences listed below: SEQ ID NO: 122, SEQ ID NO: 123, and SEQ ID NO: 124.

In one embodiment, the light chain amino acid sequence of the Elebela fusion protein provided herein is as follows: SEQ ID NO: 158, and the heavy chain amino acid sequence is one of the following sequences: SEQ ID NO: 156, SEQ ID NO: 159, SEQ ID NO: 160, SEQ ID NO: 161, SEQ ID NO: 162, SEQ ID NO: 163, SEQ ID NO: 164, and SEQ ID NO: 165. In one embodiment, the light and heavy chain amino acid sequence of the Elebela fusion protein provided herein are SEQ ID NO: 158 and SEQ ID NO: 156, respectively. In another embodiment, the light and heavy chain amino acid sequence of the Elebela fusion protein provided herein are SEQ ID NO: 158 and SEQ ID NO: 159, respectively. In another embodiment, the light and heavy chain amino acid sequence of the Elebela fusion protein provided herein are SEQ ID NO: 158 and SEQ ID NO: 160, respectively. In another embodiment, the light and heavy chain amino acid sequence of the Elebela fusion protein provided herein are SEQ ID NO: 158 and SEQ ID NO: 161, respectively. In another embodiment, the light and heavy chain amino acid sequence of the Elebela fusion protein provided herein are SEQ ID NO: 158 and SEQ ID NO: 162, respectively. In another embodiment, the light and heavy chain amino acid sequence of the Elebela fusion protein provided herein are SEQ ID NO: 158 and SEQ ID NO: 163, respectively. In another embodiment, the light and heavy chain amino acid sequence of the Elebela fusion protein provided herein are SEQ ID NO: 158 and SEQ ID NO: 164, respectively. In further embodiment, the light and heavy chain amino acid sequence of the Elebela fusion protein provided herein are SEQ ID NO: 158 and SEQ ID NO: 165, respectively.

Nucleic Acids

In one aspect, the present invention provides isolated nucleic acid molecules. The nucleic acids comprise, for example, polynucleotides that encode all or part of the Elebela fusion protein, for example, one or both chains of the Elebela fusion protein of the invention, or a fragment, derivative, mutein, or variant thereof, polynucleotides sufficient for use as hybridization probes; PCR primers or sequencing primers for identifying, analyzing, mutating or amplifying a polynucleotide encoding a polypeptide; anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) can be isolated from B-cells of mice that have been immunized with APJ antigen. The nucleic acid of the antibody of Elabela fusion protein can be isolated by conventional procedures such as polymerase chain reaction (PCR).

Nucleic acid sequences encoding the variable regions of the heavy and light chain variable regions are shown above. The skilled in the field appreciates that, due to the degeneracy of the genetic code, each of the polypeptide sequences disclosed herein is encoded by a large number of other nucleic acid sequences. The present invention provides each degenerate nucleotide sequence encoding each antibody or Elabela fusion protein of the invention.

The invention further provides nucleic acids that hybridize to other nucleic acids (e.g., nucleic acids comprising a nucleotide sequence of any of Elebela fusion proteins) under particular hybridization conditions. Methods for hybridizing nucleic acids are well-known in the field. See, e.g., Current Protocols in Molecular Biology, John Wiley & Sons, N.Y. (1989), 6.3.1-6.3.6. As defined herein, for example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the field can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., Eds., John Wiley & Sons, Inc., sections 2.10 and 6.3-6.4), and can be readily determined by those having ordinary skill in the field based on, for example, the length and/or base composition of the DNA. Changes can be introduced by mutation into a nucleic acid, thereby leading to changes in the amino acid sequence of a polypeptide (e.g., an antibody) that it encodes. Mutations can be introduced using any technique known in the field. In one embodiment, one or more particular amino acid residues are changed using, for example, a site-directed mutagenesis protocol. In another embodiment, one or more randomly selected residues are changed using, for example, a random mutagenesis protocol. No matter how it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. In one embodiment, nucleotide sequences provided herein for Elebela fusion proteins, or fragments, variants, or derivatives thereof, are mutated such that they encode amino acid sequences provided herein for Elebela fusion proteins, comprising one or more deletions or substitutions of amino acid residues to result in sequences bearing two or more different amino acid residues. In another embodiment, the mutagenesis inserts an amino acid adjacent to one or more amino acid residues shown herein for Elebela fusion proteins to result in sequences with two or more different amino acid residues. Alternatively, one or more mutations can be introduced into a nucleic acid that selectively change the biological activity. (e.g., binding to APJ) of a polypeptide that it encodes. For example, the mutation can quantitatively or qualitatively change the biological activity. Examples of quantitative changes include increasing, reducing or eliminating the activity. Examples of qualitative changes include changing the antigen specificity of Elebela fusion proteins.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a APJ binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the vectors provided herein comprise a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors provided herein can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, *Trends Biochem. Sci.* 11:287, Maniatis et al., 1987, *Science* 236:1237, the disclosure of each of which is incorporated by reference herein in its entirety), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see Id.). Those skilled in the field recognize that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell or eukaryotic cell. Prokaryotic host cells include gram-negative or gram-positive organisms, for example, *E. coli* or bacilli. Higher eukaryotic cells include insect cells, yeast cells, and established cell lines of mammalian origin. Examples of suitable mammalian host cell lines include Chinese hamster ovary (CHO) cells or their derivatives such as Veggie CHO and related cell lines which grow in serum-free media (see Rasmussen et al., 1998, *Cytotechnology* 28:31) or CHO strain DXB-11, which is deficient in DHFR (see Urlaub et al., 1980, *Proc. Natl. Acad. Sci. USA* 77:4216-20). Additional CHO cell lines include CHO-K1 (ATCC #CCL-61), EM9 (ATCC #CRL-1861), and W20 (ATCC #CRL-1862). Additional host cells include the COS-7 line of monkey kidney cells (ATCC #CRL-1651) (see Gluzman et al., 1981, *Cell* 23:175), L cells, C127 cells, 3T3 cells (ATCC CCL-163), AM-1/D cells (described in U.S. Pat. No. 6,210,924), HeLa cells, BHK (ATCC CRL-10) cell lines, the CV1/EBNA cell line derived from the African green monkey kidney cell line CV1 (ATCC CCL-70) (see McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Appropriate cloning and expression vectors for use with bacterial, fungal, yeast, and mammalian cellular hosts are described by Pouwels et al. (Cloning Vectors: A Laboratory Manual, Elsevier, N.Y., 1985).

Vector DNA can be introduced into prokaryotic or eukaryotic cells via conventional transformation or transfection techniques. For stable transfection of mammalian cells, it is known that, depending upon the expression vector and transfection technique used, only a small fraction of cells can integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene survive, while the other cells die), among other methods.

The transformed cells can be cultured under conditions that promote expression of a polypeptide, and the polypeptide recovered by conventional protein purification procedures. One such purification procedure is described in the Examples below. Polypeptides contemplated for use herein include substantially homogeneous recombinant mammalian Elabela fusion protein polypeptides substantially free of contaminating endogenous materials.

Activity of APJ Antibody

The activity of the APJ antibody refers to the effect of the antibody provided herein in binding specifically to APJ. In one embodiment, a mouse or humanized antibody provided herein specifically binds to a human APJ receptor.

In one embodiment, the $K_d$ of the antibody provided herein binding to a human APJ receptor is ranging approximately from 0.01 nM to 1000 nM, from 0.1 nM to 500 nM, from 0.5 nM to 200 nM, from 1 nM to 200 nM, or from 10 nM to 100 nM. In another embodiment, the $K_d$ of the antibody provided herein binding to a human APJ receptor is ranging approximately from 1 nM to 200 nM. In yet another embodiment, the $K_d$ of the antibody provided herein binding to a human APJ receptor is ranging approximately from 1 nM to 100 nM. In yet another embodiment, the $K_d$ of the antibody provided herein binding to a human APJ receptor is approximately 1 nM, 2 nM, 5 nM, 10 nM, 20 nM, 30 nM, 40 nM, 50 nM, 60 nM, 70 nM, 80 nM, 90 nM, or 100 nM.

In one embodiment, the antibody provided herein specifically binds to a human APJ receptor with one or more following properties:
  a. providing the substantially similar or better $K_d$ as comparing to a reference antibody in binding to a human APJ receptor; and
  b. cross-competing binding with a reference antibody to a human APJ receptor.

In one embodiment, the reference antibody comprises a combination of light chain variable domain amino acid sequence SEQ ID NO: 62 and heavy chain variable domain amino acid sequence SEQ ID NO: 67.

As used herein, the term "substantially similar" means comparable to, or approximately 200%, 180%, 160%, 150%, 140%, 120%, 110%, 100%, 99%, 98%, 97% 95%, 90%, 85%, 80%, 75%, 70%, 65%, or 50% of the $K_d$ of a reference antibody. In one embodiment, the reference antibody comprises a combination of light chain SEQ ID NO: 62 and heavy chain SEQ ID NO: 67.

Biological Activity of the Fusion Protein of APJ Antibody and Elabela

The biological activity of the fusion protein of APJ antibody and Elabela comprises the biological activity of Elabela and activity of APJ antibody. The activity of the APJ antibody is as described above. "Elabela biological activity" refers to the biological activity of the Elabela fusion protein that binds in vivo and activates Elabela receptor (e.g., APJ) and causes cellular stress response. The cellular stress response comprises, but not limited to, enhancing myocardial contractility, relaxing blood vessels, lowering blood pressure, diuresis (reducing the release of antidiuretic hormone), regulating immune response and pituitary related hormone release, etc. Combining the biological activity of Elabela and APJ antibodies, the Elabela fusion protein provided herein can be used to treat various diseases and symptoms associated with Elabela and APJ. The fusion protein exerts its biological effect by acting on Elabela and/or APJ, so the Elabela fusion protein treatment provided herein can be used to treat subjects whose disease or symptom benefit from "increasing Elabela stimulation." These subjects are referred to as subjects who "need Elabela stimulation therapy." These subjects include acute heart failure, chronic heart failure, pulmonary hypertension and pulmonary arterial hypertension, and also includes subjects with diabetic vascular disease, cardiac insufficiency, atrial fibrillation, and ischemia-reperfusion injury.

In one embodiment, the biological activity of the Elabela fusion protein is detected using report gene assay measurement approach, quantifying the function of Elabela fusion protein in activating APJ in vitro.

In one embodiment, the $EC_{50}$ of the antibody and Elabela fusion protein provided herein in activating the Elabela/APJ signaling pathway is ranging approximately from 0.1 nM to 100 nM, from 0.5 nM to 20 nM, from 1 nM to 10 nM, or from 1 nM to 5 nM.

Pharmaceutical Compositions

In one embodiment, a pharmaceutical composition provided herein comprises an Elabela fusion protein provided herein and one or more pharmaceutically acceptable carriers.

In one embodiment, a pharmaceutical composition comprises an Elabela fusion protein provided herein and one or more substances selected from the following: buffer solution with pH suitable for Elabela fusion protein, antioxidant (e.g., ascorbic acid), low molecular weight polypeptide (e.g., polypeptide containing less than 10 amino acids), protein, amino acid, sugar example (such as dextrin), complex (e.g., EDTA), glutathione, stabilizer and excipients. In one embodiment, a pharmaceutical composition provided herein can also comprise preservative. In one embodiment, the pharmaceutical composition provided herein can be prepared into a lyophilized powder using an appropriate excipient solution as a diluent. Further examples of components that can be used in drug prescription are given in Remington's Pharmaceutical Sciences, 16$^{th}$ Edition (1980) and 20$^{th}$ edition (2000), Mack publishing company.

Treatment Method

In one embodiment, provided herein is a method of treating, preventing, or ameliorating PAH, comprising administration to a subject a therapeutically effective dosage of the Elabela fusion protein provided herein or a pharmaceutical composition thereof.

In another embodiment, provided herein is a method of treating, preventing, or ameliorating PH, comprising administration to a subject a therapeutically effective dosage of the Elabela fusion protein provided herein or a pharmaceutical composition thereof.

In another embodiment, provided herein is a method of treating, preventing, or ameliorating heart failure, comprising administration to a subject a therapeutically effective dosage of the Elabela fusion protein provided herein or a pharmaceutical composition thereof.

In another embodiment, provided herein is a method of treating, preventing, or ameliorating T2D and its related metabolic syndrome, comprising administration to a subject a therapeutically effective dosage of the Elabela fusion protein provided herein or a pharmaceutical composition thereof.

In another embodiment, provided herein is a method of treating, preventing, or ameliorating two or more diseases of pulmonary hypertension, pulmonary arterial hypertension, type 2 diabetes mellitus and its related metabolic syndrome, or heart failure, comprising administration to a subject a therapeutically effective dosage of the Elabela fusion protein provided herein or a pharmaceutical composition thereof.

In any one of the uses provided herein, the pharmaceutical composition provided herein is for intravenous or subcutaneous injection.

A pharmaceutical composition of an Elabela fusion protein can be administered by any suitable technique, including, but not limited to, parenterally, topically, or by inhalation. If injected, the pharmaceutical composition can be administered by rapid injection or continuous infusion via, for example, intra-articular, intravenous, intramuscular, intralesional, intra-abdominal, or subcutaneous route. It is considered, for example, localized administration at the disease or injury site, such as transdermal administration and sustained release of an implant. Delivery by inhalation includes, for example, nasal or oral inhalation, use of a nebulizer, inhalation of an Elabela fusion protein in aerosol form, and the like. Other alternatives include oral preparations, including pills, syrups, or lozenges.

Dosages and the frequency of administration can vary according to such factors as the route of administration, the particular Elabela fusion protein employed, the nature and severity of the disease to be treated, whether the condition is acute or chronic, and the size and general condition of the subject. Appropriate dosages can be determined by procedures known in the pertinent field, e.g. in clinical trials that can involve dose escalation studies.

The Elabela fusion protein provided herein can be administered, for example, once or more than once, e.g., at regular intervals, over a period of time. In particular embodiments, the Elabela fusion protein is administered once over a period of at least a month or longer, e.g., for one, two, or three months or even indefinitely. For treating chronic conditions, long-term treatment is generally most effective. However, for treating acute conditions, administration for shorter periods, e.g., from one to six weeks, can be sufficient. In general, the Elabela fusion protein is administered until the patient manifests a medically relevant degree of improvement over baseline for the chosen indicator or indicators.

An example of the treatment regimen presented here includes subcutaneous injection of Elabela fusion protein at an appropriate dose once a week or longer to treat symptoms caused by type 2 diabetes and its related metabolic syndrome, acute heart failure, chronic heart failure, pulmonary hypertension or pulmonary arterial hypertension. The Elabela fusion protein can be administered weekly or monthly until desired result is achieved, for example, the patient's symptoms subside. Treatment can be renewed as needed, or, alternatively, a maintenance dose can be given.

The patient's blood BNP or pro-BNP concentration and body weight can be monitored before, during and/or after treatment with Elabela fusion protein to detect any changes in their pressure. For certain conditions, changes in BNP or pro-BNP can vary with factors such as disease progression. The BNP or pro-BNP concentration can be determined using known techniques.

Specific embodiments of the methods and compositions herein involve the use of, for example, an Elabela fusion protein and one or more Elabela agonists, two or more Elabela fusion proteins provided herein, or the Elabela fusion protein provided herein and one or more other Elabela agonists. In a further embodiment, Elabela fusion protein is administered alone or in combination with other agents used to treat symptoms that are painful for the patient. Examples of these agents include protein and non-protein drugs. When multiple drugs are administered in combination, the dosage should be adjusted accordingly as is well known in the field. "Combined administration" combination therapy is not limited to simultaneous administration, but also includes treatment regimens in which the antigen and protein are administered at least once during the course of administration involving the administration of at least one other therapeutic agent to the patient.

On the other hand, provided herein is a method for preparing a medicament for treating heart failure and pulmonary arterial hypertension and related disorders, which comprises a mixture of the Elabela fusion protein provided herein and a pharmaceutically acceptable excipient for the treatment of the related diseases of the above diseases. The pharmaceutical preparation method is as described above.

Further provided herein are compositions, kits, and methods related to Elabela fusion protein that can specifically bind to human APJ. Nucleic acid molecules and derivatives and fragments thereof are also provided, wherein comprising polynucleotides encoding all or part of a polypeptide that binds to APJ, for example, nucleic acid encoding all or part of Elabela fusion proteins or Elabela fusion protein derivatives. Further provided herein are vectors and plasmids containing such nucleic acids and cells and cell lines containing such nucleic acids and/or vectors and plasmids. Methods provided herein comprise, for example, methods for preparing, identifying, or isolating Elabela fusion proteins that bind to human APJ, a method to determine whether the Elabela fusion protein binds to APJ, and a method of administering the Elabela fusion protein that binds to APJ into an animal model.

EXAMPLES

The technical solutions described herein are further illustrated by the following examples.

If not specified, the stating materials and equipment described herein are commercially available or commonly used in the art. The methods in the following examples, unless otherwise specified, are all conventional methods in the art.

1. Preparation of Antigen for Immunization

CHO-DIFR-cells were seeded into a 6-well plate. After 24 h culture, the cells were transfected with pTM15 plasmids which were modified to carry hAPJ gene (see SEQ ID NO: 55 for the nucleotide sequence, and SEQ ID NO: 23 for the amino acid sequence). The transfection was carried out by following the transfection conditions recommended by Invitrogen for Lipofectamine 2000. Forty-eight hours after transfection, the medium was replaced with a complete medium containing 300 μg/mL hygromycin, then the medium was changed every 3 days. The stable clones appeared after about two-weeks culture. After digesting and dispersing the cell colonies, the cells were passaged and further cultured until the cells grew to 100% healing degree. The stable cell lines were detected by FACS using V5 labeled antibody (Life Technologies), and the cell populations after pressurization were identified according to the results of FACS detection. The selected CHO-DHFR-hAPJ cells expressed a large number of hAPJ on cell membrane. Finally, after subcloning and further identification, three APJ cell lines were selected as high expression stable cell lines. These cell lines with high expression of hAPJ can be used as immunogens for antibody preparation (refer to example 2).

In addition, the fusion protein of hAPJ extracellular domain and hIgG FC can also be used as immunogen for antibody preparation. The preparation method is as following: The fusion protein gene sequence of the extracellular domain of hAPJ, hIgG2 FC and linker was subcloned into pTM5 plasmid. The APJ extracellular domain fusion protein was highly and transiently expressed in suspended HEK293 cells. Then the cell supernatant was collected and the APJ extracellular domain fusion protein was purified by affinity chromatography.

2. Preparation of APJ Antibodies

The antigen and aluminum hydroxide adjuvant were mixed and injected subcutaneously into BALB/c mice (6-8 weeks). The mice were boosted once every week. After immunization for 6 times in total, blood samples were collected through clipping tails. Then the serum was collected by centrifugation and serum titer was analyzed by FACS. Once the acceptable antibody titers were achieved, the mice were sacrificed by cervical dislocation, and their spleen cells were harvested under aseptic conditions. Moreover, SP2/0 cells were collected at the logarithmic phase of growth and centrifuged, the cell pellets were resuspended with serum-free culture medium, then centrifuged and resuspended for a second time and counted. Similar number of spleen cells and SP2/0 cells were mixed, followed by 3 rounds of washing-centrifugation. After the cell pellets from the last centrifugation were gently detached, pre-warmed PEG-1500 was added dropwise followed by pipette-mixing, then 30 mL of the pre-warmed serum-free medium was added slowly to terminate the PEG fusion. After centrifugation, the cell pellets were detached followed by addition of fusion culture medium. Spleen cells and feeder layer cells were plated in 96-well plates, and 100 μL culture medium was added into each well. The hybridoma cells after fusion and layer feeder cells were cultured together in 96-well plates followed by HAT (sarcine, amethopterin and thymidine) selection to get rid of the non-fused cells. Ten days later, the supernatants of the hybridoma cells in the culture plates were collected for ELISA analysis.

3. ELISA Screening of APJ Antibodies

CHO-DHFR-hAPJ cells with hAPJ over expression and CHO-DHFR-cells without hAPJ expression were seeded into 96-well plates, respectively. When cells grew to 90% confluence, the supernatant of the culture medium was removed and attached cells were washed twice with PBS, and 100% methanol was added to fix the cells at 4° C., then 100 μL of $H_2O_2$—PBS was added followed by incubation at room temperature for 20 min. Then the cells were washed twice with PBS. After blocking with BSA (dissolved in PBS), the hybridoma supernatant was added and incubated for 90 min at 4° C. After several washes, 100 μL of the diluted secondary antibody goat-anti-mouse Fc-HRP was added into each well and incubated at 37° C. for 30 min. After washing for five times, 100 μL of TMB chromogenic substrate was added into each well and incubated at 37° C. for 15 min, then 50 μL 2M $H_2SO_4$ was added to terminate the reaction, and $OD_{450}$ values were read. After blocking with 1% BSA (dissolved in PBS), the hybridoma supernatant was added and incubated for 90 min at 4° C. Then the ELISA method described above was performed to screen anti-hAPJ monoclonal antibodies. The positive control was the mouse serum after immunization; the negative control was the cell culture supernatant. After initial analysis by ELISA, several positive hybridoma clones secreting anti-hAPJ antibodies were identified. Those hybridoma clones secreting anti-hAPJ antibodies were selected and went through cloning to get the stable cell lines secreting anti-hAPJ antibodies. Lastly, the affinity of ascites antibodies secreted by positive hybridoma was verified and ranked by FACS analysis (refer to example 9).

4. Cloning and Subcloning of APJ Antibody Genes

Hybridoma cells secreting antibodies were collected. Hybridoma mRNA was extracted according to the manufacturer protocol of QIAGEN mRNA extraction kit. Then the extracted mRNA was transcribed reversely into cDNA. The reverse transcription primers were specific primers for the light and heavy chain constant regions of a mouse, with the heavy chain reverse transcription primer being (5'-TTTGGRGGGAAGATGAAGAC-3') (SEQ ID NO: 168), and the light chain reverse transcription primers being (5'-TTAACACTCTCCCCTGTTGAA-3') (SEQ ID NO: 169) and (5'-TTAACACTCATTCCTGTTGAA-3') (SEQ ID NO: 170). RT-PCR reaction conditions were as following: 25° C. for 5 min, 50° C. for 60 min, and 70° C. for 15 min. Reversely transcribed cDNA was diluted with 0.1 mM TE to 500 μL, then added into the ultrafiltration centrifuge tube (Amicon Ultra-0.5) and centrifuged at 2,000 g for 10 min. The filtrate was removed, 500 μL of 0.1 mM TE was added and centrifuged at 2,000 g for 10 min. The filtrate was removed and the preparation tube was placed in inversion to the new centrifugal tube, and centrifuged at 2,000 g for 10 min to obtain the purified cDNA. Purified cDNA (10 μL) was taken as a template, followed by addition of 4 μL 5× tailing buffer (Promega), 4 μL dATP (1 mM) and 10 U terminal transferase (Promega), mixing uniformly, incubation at 37° C. for 5 min and incubation again at 65° C. for 5 min. Then the PolyA tail cDNA was used as a template and PCR was performed to amplify genes of the light and heavy chain variable region of antibodies. Upstream primers were all oligodT, heavy chain downstream primers were (5'-TGGACAGGGATCCAGAGTTCC-3') (SEQ ID NO: 171) and (5'-TGGACAGGGCTCCATAGTTCC-3') (SEQ ID NO: 172), and light chain downstream primer was (5'-ACTCGTCCTTGGTCAACGTG-3') (SEQ ID NO: 173). The PCR reaction conditions were as following: 95° C. for 5 min; 95° C. for 30 s, 56° C. for 30 s, 72° C. for 1 min, 40 cycles; and 72° C. for 7 min. The PCR products were connected to the PMD 18-T vector (Takara Bio) and then sequenced. Then the PCR primers were designed based on the DNA sequences of the antibodies to ligate the complete light chain, heavy chain signal peptides and variable domains and mouse IgG1 constant region into expression vector pTM5.

5. APJ Antibody Humanization, Optimization and Subcloning

The sequences of light and heavy chain variable regions of the screened mouse antibodies were aligned with the homologous antibodies, using NCBI database to search the germline gene sequences of a human antibody (Ig Germline Gene sequence) homologous to variable region sequence of the selected antibodies for humanization, and the human gene sequence with highest homology except CDR sequences was used as a template for CDR grafting to obtain humanized antibody variable region sequences. The genes of humanized antibody light and heavy chains were synthesized and then combined with the human IgG2 or IgG4 constant region sequence to obtain whole recombinant humanized antibody sequences. The expression of the recombinant antibodies was achieved according to example 8, and their affinities to APJ was analyzed by FACS as described in step 10. The humanized antibody candidate retaining best affinity to APJ was selected from the group, and its variable region sequence was further modified by site-specific mutagenesis for improved affinity to APJ.

The optimized heavy chain and light chain variable region sequences of humanized antibody were synthesized by a CRO, and the complete heavy chain variable region sequence was further connected with the expression vector pTM5 which had been loaded with the heavy chain constant region; similarly, the complete light chain variable region sequence was connected with the expression vector pTM5 which had been loaded with the light chain constant region.

6. Construction of the Humanized APJ Antibody and Elabela Fusion Protein

The optimized humanized antibody was fused with the Elabela fragment at the C-terminal of the heavy chain to form the Elabela fusion protein. The two sequences were linked by linker as a bridge. The heavy chain nucleic acid sequence of the humanized APJ antibody was partially linked to the "linker Elabela fragment" by overlapping PCR, and the restriction sites of Nhe1 and Not1 were added at both ends of the primers, so as to connect the complete fusion protein sequence with the expression vector pTM5. After the Elabela fusion protein sequence was connected to the expression vector pTM5, sequencing analysis was carried out to confirm the correctness of the construction.

7. Transient Expression of the APJ Antibody and Elabela Fusion Protein $5 \times 10^5$/mL suspension cells of HEK293 or CHO expression cell line was seeded in a shaker flask. After 24 h rotation at 37° C. and 5% $CO_2$, the cell density reached $1 \times 10^6$/mL and was then used for transfection. Polyethylenimine (PEI) was used as a transfection reagent and mixed with DNA during transfection. A mixture of both was incubated quiescently for 15 min then was added into the cell culture. The cells after treated with the PEI/DNA mixture were rotated for 24 h at 37° C. and 5% $CO_2$, then tryptone was added into the cell culture as a supplement required by expression. After the completion of expression (more than 96 h), the cell supernatant was collected for the antibody purification and separation.

8. Purification and Separation of the APJ Antibody and Elabela Fusion Protein The cell supernatant harvested from example 8 was centrifuged at 8000 rpm to remove cells and cellular debris, then filtered by 0.22 m filter to get clear supernatant for purification. The purification process was done through chromatograph. Firstly, the supernatant was passed through A/G protein coupled affinity chromatography column, and antibodies or fusion proteins were remained in the column after binding to the ligands of the A/G protein coupled affinity chromatography column. The antibodies or fusion proteins were eluted from the chromatography column using an eluent with pH of 3.0 or less. The collected eluent was neutralized immediately with 1M Tris-HCl. The antibody or fusion protein eluent was then dialyzed into a PBS or other buffer.

Figure 1B:
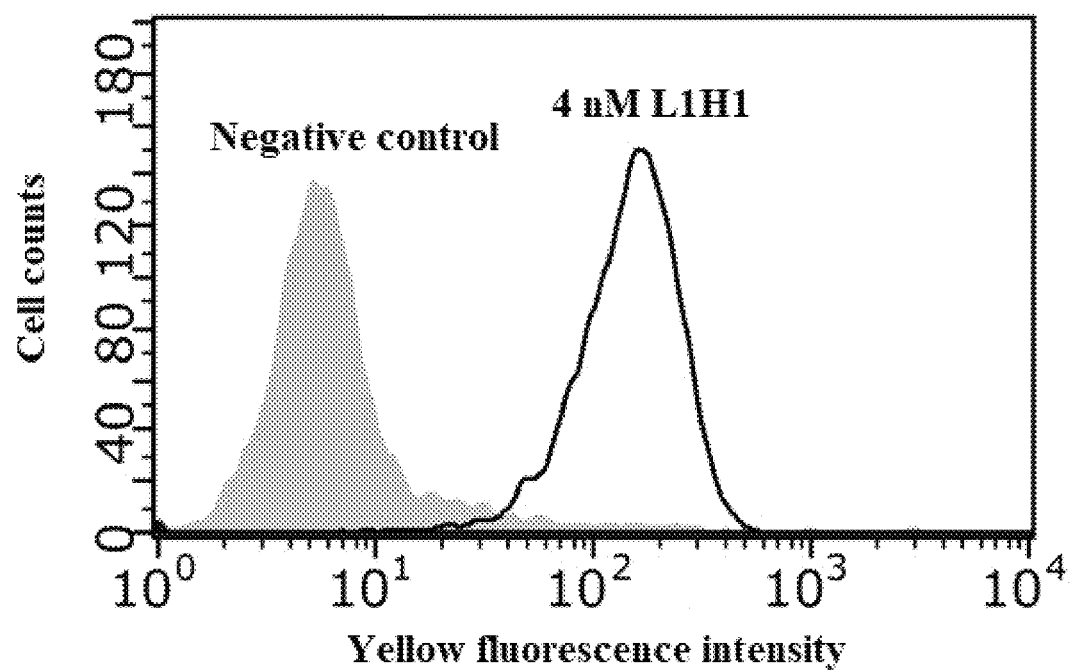
Figure 1C:
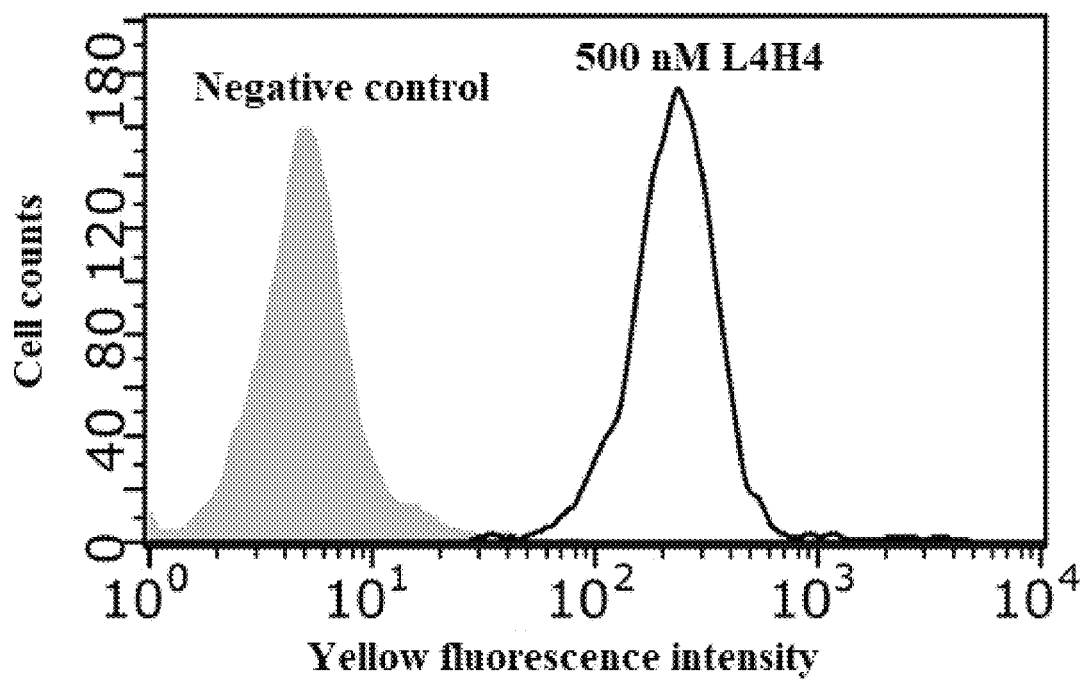
Figure 1D:
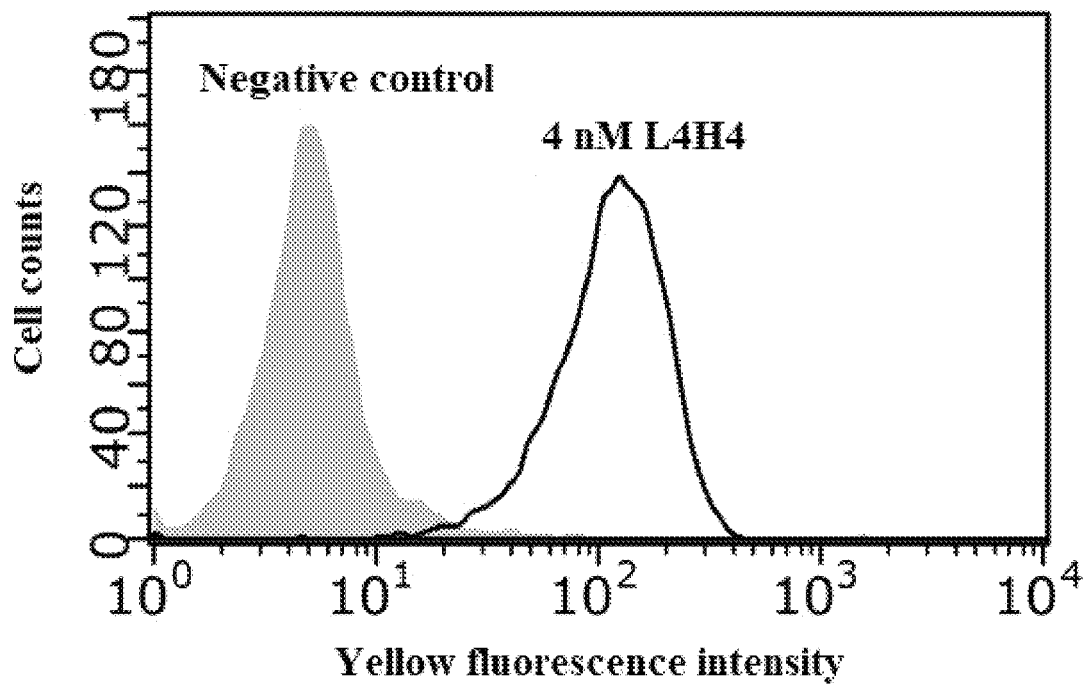

9. Binding Activity Verification of Functional APJ Antibodies Through FACS Analysis PBS containing EDTA was used to detach and collect $10^5$ CHO-DHFR-hAPJ cells into 1.5 mL EP tubes. The supernatant was removed after centrifugation. The negative control sample was resuspended with a FACS loading buffer (PBS, 2% FBS). For the positive control, 200 µL antibody supernatant with certain concentration was added to resuspend cells and then incubated at room temperature; the cells were then centrifuged at 1500 rpm to remove the supernatant, washed with a FACS loading buffer and centrifuged again. The cells were resuspended followed by addition (200 µL/well) of a FITC labeled goat anti-mouse fluorescent secondary antibody at 1:50 dilution and incubated at room temperature for 30 min in the dark. Supernatant was removed after centrifugation, cells were washed with FACS loading buffer, centrifuged again and resuspended with the loading buffer for analysis. In the experimental results shown in FIG. 1A to FIG. 1D, the gray peak on the left side was the negative control of 500 nM mouse ascites antibody L1H1 binding with blank cell CHO-DHFR—, and the solid line peaks were the binding curves of mouse ascites antibody L1H1 at 500 nM (FIG. 1A) and 4 nM (FIG. 1B), respectively, binding with CHO-DHFR-hAPJ, which shifted to the right obviously compared with the negative control of gray peak, and proved the specific binding of L1H1 and hAPJ. The right gray peak was the negative control of 500 nM mouse ascites antibody L4H4 binding with blank cell CHO-DHFR—, and the solid line peaks were the binding curves of mouse ascites antibody L4H4 at 500 nM (FIG. 1 C) and 4 nM (FIG. 1 D), respectively, binding with CHO-DHFR-hAPJ, which shifted to the right obviously compared with the negative control of gray peak, and proved the specific binding of L4H4 and hAPJ.

Figure 2:
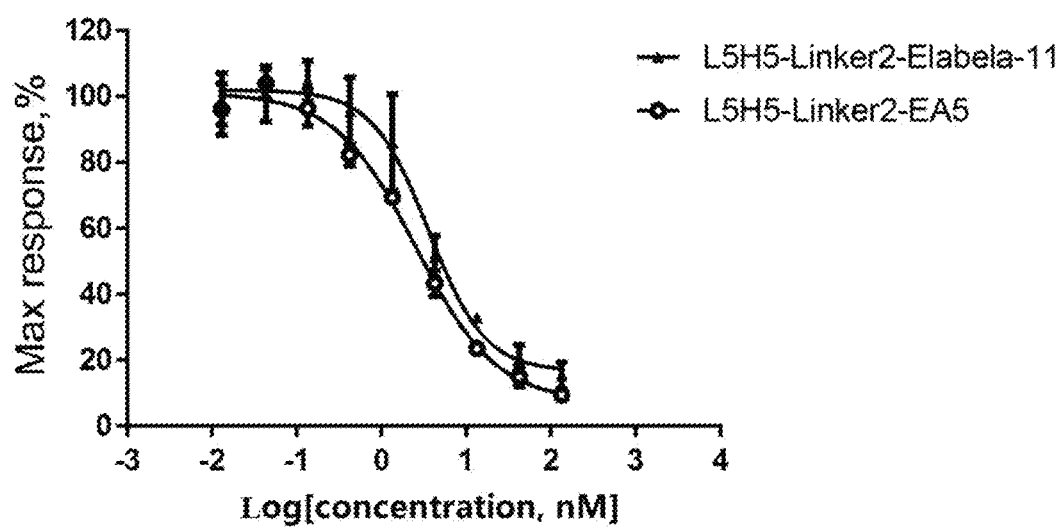
FIG. 2 shows the activation curves of the reporter gene assay test of hAPJ antibody L5H5 (comprising SEQ ID NO: 63 and SEQ ID NO: 68) and Linker2-Elabela-11 (comprising SEQ ID NO: 123 and SEQ ID NO: 93) fusion protein, and L5H5 and Linker2-EA5 (comprising SEQ ID NO: 123 and SEQ ID NO: 94) fusion protein to activate Elabela/APJ signaling pathway, and $EC_{50}$ is: 3.6 nM and 2.6 nM, respectively.
Figure 3:
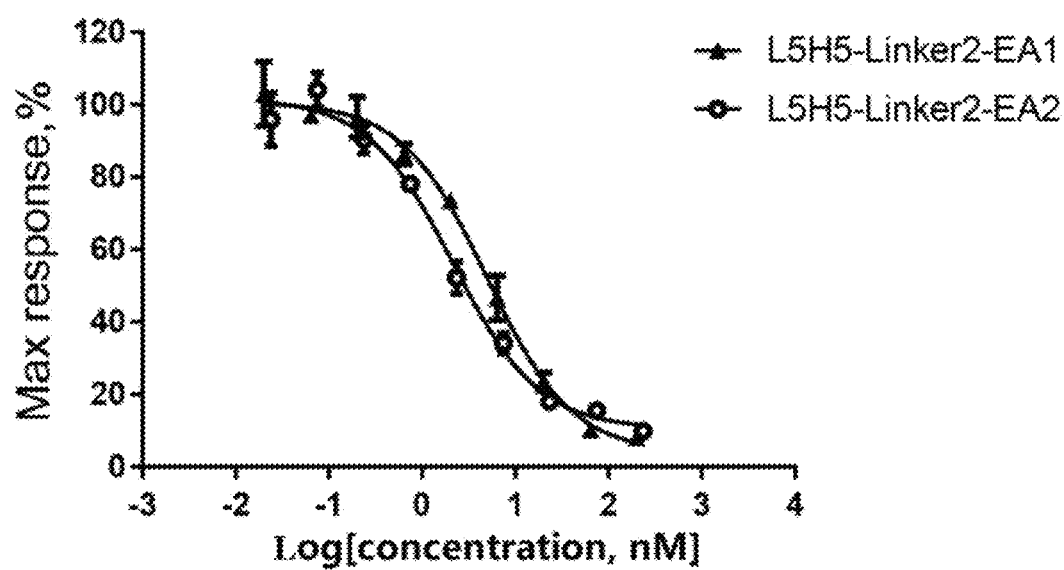
FIG. 3 shows the activation curves of the reporter gene assay test of hAPJ antibody L5H5 and Linker2-EA1 (comprising SEQ ID NO: 123 and SEQ ID NO: 103) fusion protein, and L5H5 and Linker2-EA2 (comprising SEQ ID NO: 123 and SEQ ID NO: 107) fusion protein to activate Elabela/APJ signaling pathway, and $EC_{50}$ is 5.0 nM and 2.2 nM, respectively.
Figure 4:
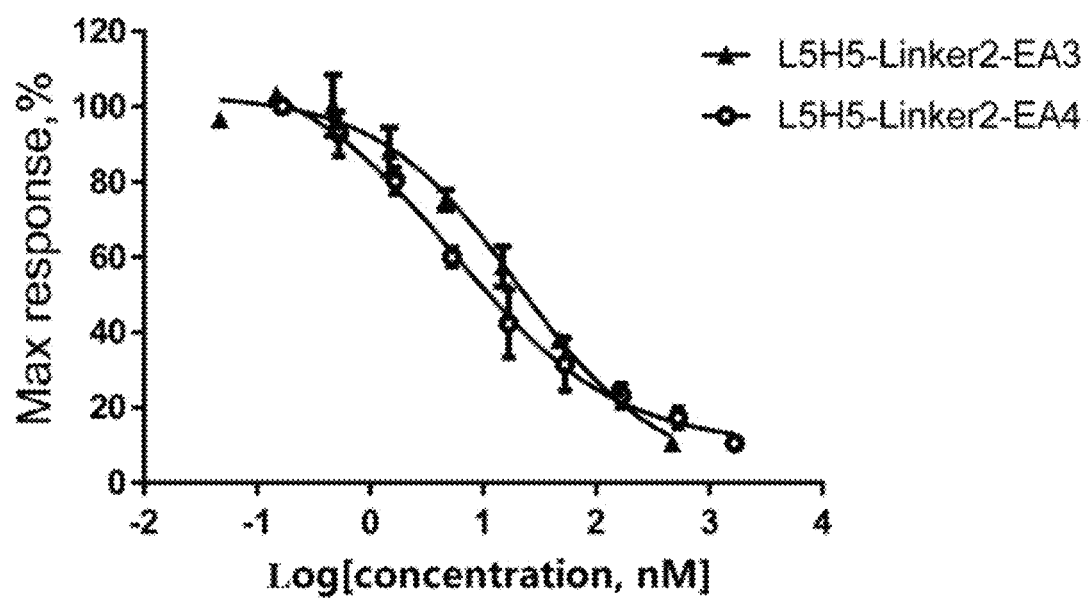
FIG. 4 shows the activation curves of the reporter gene assay test of hAPJ antibody L5H5 and Linker2-EA3 (comprising SEQ ID NO: 123 and SEQ ID NO: 109) fusion protein, and L5H5 and Linker2-EA4 (comprising SEQ ID NO: 123 and SEQ ID NO: 116) fusion protein to activate Elabela/APJ signaling pathway, and $EC_{50}$ is: 20.3 nM and 5.4 nM, respectively.

10. Reporter Gene Assay Measurement of the In Vitro Activation of Elabela/APJ Signaling Pathway by Elabela and Elabela Fusion Protein 35000 hAPJ-CRE-Luciferase expressing CHO-DHFR- cells per well were seeded into 96 well plate, and cultured overnight at 37° C. The culture supernatant was removed the second day, cells were washed twice with serum-free medium, and the residue liquid was aspirated. 50 μL of 0.6 μM forskolin was added in 96 well plate in advance, then 50 μL of Elabela fusion protein or Elabela-11 polypeptide diluted in serum-free medium was added, and incubated at 37° C. for 6 hours. After stimulation, 100 μL Bright Glo chemical luminescence substrate (Promega) was added, then the cell lysate was transferred to white 96 well plate, and the relative intensity of fluorescence was read in the SpectraMax L (Molecular Devices). The data were fitted with prism5.0 and EC50 was calculated. The antibodies of L1H1 and L4H4 did not block or activate APJ receptor. FIG. 2 shows the activation curves of Elabela/APJ signaling pathway activated by the fusion protein of L5H5 and linker2-Elabela-11, and the fusion protein of L5H5 and linker2-EA5 detected by reporter gene experiment, with $EC_{50}$ of 3.61 and 2.55 nM, respectively. FIG. 3 shows the activation curves of Elabela/APJ signaling pathway activated by the fusion protein of L5H5 and linker2-EA1, and fusion protein of L5H5 and linker2-EA2 detected by reporter gene experiment, with $EC_{50}$ of 4.95 and 2.16 nM, respectively. FIG. 4 shows the activation curves of Elabela/APJ signaling pathway activated by the fusion protein of L5H5 and linker2-EA3, and fusion protein of L5H5 and linker2-EA4 detected by reporter gene experiment, with $EC_{50}$ of 20.27 and 5.43 nM, respectively.

The above examples are provided to fully disclose and explain to those of ordinary skill in the art how to manufacture and use the embodiments requiring protection, without limiting the scope of the disclosure herein. The obvious modifications to those skilled in the art are within the scope of the claims herein. All publications, patents, and patent applications cited in this specification are incorporated herein by reference as if each publication, patent or patent application were specifically and individually incorporated herein by reference.

What is claimed is:

1. An antibody specifically binding to human apelin receptor (APJ), wherein the antibody comprises:
   a. light chain CDR1 amino acid sequence: SEQ ID NO: 1; light chain CDR2 amino acid sequence: SEQ ID NO: 2; light chain CDR3 amino acid sequence: SEQ ID NO: 3; heavy chain CDR1 amino acid sequence: SEQ ID NO: 12; heavy chain CDR2 amino acid sequence: SEQ ID NO: 13; and heavy chain CDR3 amino acid sequence: SEQ ID NO: 14;
   b. light chain CDR1 amino acid sequence: SEQ ID NO: 4; light chain CDR2 amino acid sequence: SEQ ID NO: 5; light chain CDR3 amino acid sequence: SEQ ID NO: 6; heavy chain CDR1 amino acid sequence: SEQ ID NO: 15; heavy chain CDR2 amino acid sequence: SEQ ID NO: 16; and heavy chain CDR3 amino acid sequence: SEQ ID NO: 17;
   c. light chain CDR1 amino acid sequence: SEQ ID NO: 7; light chain CDR2 amino acid sequence: SEQ ID NO: 8; light chain CDR3 amino acid sequence: SEQ ID NO: 9; heavy chain CDR1 amino acid sequence: SEQ ID NO: 18; heavy chain CDR2 amino acid sequence: SEQ ID NO: 19; and heavy chain CDR3 amino acid sequence: SEQ ID NO: 20; or
   d. light chain CDR1 amino acid sequence: SEQ ID NO: 10; light chain CDR2 amino acid sequence: SEQ ID NO: 5; light chain CDR3 amino acid sequence: SEQ ID NO: 11; heavy chain CDR1 amino acid sequence: SEQ ID NO: 18; heavy chain CDR2 amino acid sequence: SEQ ID NO: 21; and heavy chain CDR3 amino acid sequence: SEQ ID NO: 22.

2. The antibody of the claim 1, wherein the antibody comprises: light chain CDR1 amino acid sequence: SEQ ID NO: 10; light chain CDR2 amino acid sequence: SEQ ID NO: 5; light chain CDR3 amino acid sequence: SEQ ID NO: 11; heavy chain CDR1 amino acid sequence: SEQ ID NO: 18; heavy chain CDR2 amino acid sequence: SEQ ID NO: 21; and heavy chain CDR3 amino acid sequence: SEQ ID NO: 22.

3. The antibody of claim 1, wherein the antibody comprises 1 or 2 amino acid sequences, wherein each amino acid sequence is independently selected from:
   a. a light chain variable domain amino acid sequence selected from the group consisting of SEQ ID NO: 59, SEQ ID NO: 60, SEQ ID NO: 61, SEQ ID NO: 62, and SEQ ID NO: 63; and an amino acid sequence that is at least 80%, 85%, 90% or 95% identical to one of the amino acid sequences listed above, and
   b. a heavy chain variable domain amino acid sequence selected from the group consisting of: SEQ ID NO: 64, SEQ ID NO: 65, SEQ ID NO: 66, SEQ ID NO: 67, and SEQ ID NO: 68; and an amino acid sequence that is at least 80%, 85%, 90% or 95% identical to one of the amino acid sequences listed above.

4. The antibody of claim 1, wherein the antibody comprises or further comprises an amino acid sequence independently selected from the group consisting of: SEQ ID NO: 59, SEQ ID NO: 60, SEQ ID NO: 61, SEQ ID NO: 62, and SEQ ID NO: 63.

5. The antibody of claim 1, wherein the antibody comprises or further comprises an amino acid sequence independently selected from the group consisting of: SEQ ID NO: 64, SEQ ID NO: 65, SEQ ID NO: 66, SEQ ID NO: 67, and SEQ ID NO: 68.

6. The antibody of claim 1, wherein the antibody comprises a combination of light chain and heavy chain variable domain amino acid sequences independently selected from the group consisting of: SEQ ID NO: 59 and SEQ ID NO: 64; SEQ ID NO: 60 and SEQ ID NO: 65; SEQ ID NO: 61 and SEQ ID NO: 66; SEQ ID NO: 62 and SEQ ID NO: 67; and SEQ ID NO: 63 and SEQ ID NO: 68.

7. The antibody of claim 1, wherein the antibody comprises 1 or 2 amino acid sequences, wherein each amino acid sequence is independently selected from:
   a. a light chain constant region amino acid sequence selected from the group consisting of: SEQ ID NO: 79, SEQ ID NO: 80 and SEQ ID NO: 81; and
   b. a heavy chain constant region amino acid sequence selected from the group consisting of: SEQ ID NO: 82, SEQ ID NO: 83 and SEQ ID NO: 84.

8. The antibody of claim 1, wherein the antibody is selected from murine antibodies, humanized antibodies, chimeric antibodies, monoclonal antibodies, polyclonal antibodies, recombinant antibodies, antigen-binding antibody fragments, single-chain antibodies, double-chain antibodies, triple-chain antibodies, tetra-chain antibodies, Fab fragments, F(ab')x fragments, domain antibodies, IgD antibodies, IgE antibodies, IgM antibodies, IgG1 antibodies, IgG2 antibodies, IgG3 antibodies, and IgG4 antibodies.

9. The antibody of claim 1, wherein the antibody is a murine antibody or humanized antibody.

10. The antibody of claim 1, wherein the antibody is a monoclonal antibody.

11. The antibody of claim 1, wherein the antibody has a $K_d$ that ranges approximately from 1 nM to 200 nM or approximately from 1 nM to 100 nM.

12. A composition comprising the antibody of claim 1, and a pharmaceutically acceptable carrier.

* * * * *